US009403756B2

(12) United States Patent
Attali et al.

(10) Patent No.: US 9,403,756 B2
(45) Date of Patent: Aug. 2, 2016

(54) N-PHENYL ANTHRANILIC ACID DERIVATIVES AND USES THEREOF

(71) Applicant: Ramot at Tel-Aviv University Ltd., Tel-Aviv (IL)

(72) Inventors: Bernard Attali, Rechovot (IL); Asher Peretz, Kfar Saba (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 14/318,774

(22) Filed: Jun. 30, 2014

(65) Prior Publication Data

US 2014/0316008 A1    Oct. 23, 2014

Related U.S. Application Data

(63) Continuation of application No. 12/452,353, filed as application No. PCT/IL2008/001257 on Sep. 18, 2008, now Pat. No. 8,765,815.

(60) Provisional application No. 60/996,398, filed on Nov. 15, 2007, provisional application No. 60/960,215, filed on Sep. 20, 2007.

(51) Int. Cl.
| C07D 207/40 | (2006.01) |
| C07D 213/80 | (2006.01) |
| C07D 303/16 | (2006.01) |
| C07C 237/20 | (2006.01) |
| C07C 229/42 | (2006.01) |
| C07C 229/58 | (2006.01) |
| C07C 233/54 | (2006.01) |
| C07C 237/32 | (2006.01) |
| C07C 291/02 | (2006.01) |

(52) U.S. Cl.
CPC ............ *C07C 237/20* (2013.01); *C07C 229/42* (2013.01); *C07C 229/58* (2013.01); *C07C 233/54* (2013.01); *C07C 237/32* (2013.01); *C07C 291/02* (2013.01); *C07D 207/40* (2013.01); *C07D 213/80* (2013.01); *C07D 303/16* (2013.01)

(58) Field of Classification Search
CPC ... C07D 207/40; C07D 213/80; C07D 303/16
See application file for complete search history.

(56) References Cited

U.S. PATENT DOCUMENTS

| 3,652,762 A | 3/1972 | Sallmann et al. |
| 4,016,166 A | 4/1977 | Noda et al. |
| 4,283,532 A | 8/1981 | Nohara |
| 4,734,434 A | 3/1988 | Procaccini et al. |
| 4,857,645 A | 8/1989 | Makoto et al. |
| 5,017,604 A | 5/1991 | Belliotti et al. |
| 5,384,330 A | 1/1995 | Dieter et al. |
| 5,565,483 A | 10/1996 | Hewawasam et al. |
| 6,117,900 A | 9/2000 | Rundfeldt et al. |
| 6,291,442 B1 | 9/2001 | Yellen |
| 6,291,523 B1 | 9/2001 | Fujimoto et al. |
| 6,326,385 B1 | 12/2001 | Wickenden et al. |
| 6,348,486 B1 | 2/2002 | Argentieri et al. |
| 6,355,666 B1 | 3/2002 | Lai et al. |
| 6,355,680 B1 | 3/2002 | Cohen |
| 6,472,165 B1 | 10/2002 | Rundfeldt et al. |
| 6,589,986 B2 | 7/2003 | Bowlby et al. |
| 6,593,349 B2 | 7/2003 | McNaughton-Smith et al. |
| 7,378,442 B1 | 5/2008 | Majeed et al. |
| 7,632,866 B2 | 12/2009 | Attali et al. |
| 2003/0055095 A1 | 3/2003 | Baragi et al. |
| 2005/0250833 A1 | 11/2005 | Attali et al. |
| 2008/0004245 A1 | 1/2008 | Wallace et al. |
| 2010/0056591 A1 | 3/2010 | Attali et al. |
| 2010/0137296 A1 | 6/2010 | Attali et al. |
| 2012/0178785 A1 | 7/2012 | Attali et al. |

FOREIGN PATENT DOCUMENTS

| EP | 0131790 | 1/1985 |
| EP | 0307599 | 3/1989 |
| EP | 0335164 | 10/1989 |
| EP | 0336147 | 10/1989 |
| EP | 0452179 | 10/1991 |
| EP | 0554543 | 2/1996 |
| FR | 2411825 | 7/1979 |
| FR | 2462420 | 2/1981 |
| JP | 50-032189 | 3/1975 |
| JP | 50-095285 | 7/1975 |
| JP | 63-275549 | 11/1988 |
| JP | 63-275593 | 11/1988 |

(Continued)

OTHER PUBLICATIONS

U.S. Appl. No. 60/419,525, filed Oct. 16, 2002, Attali et al.
Advisory Action Before the Filing of an Appeal Brief Dated Jan. 9, 2012 From the US Patent and Trademark Office Re. U.S. Appl. No. 12/591,090.
Applicant-Initiated Interview Summary Dated Apr. 25, 2013 From the US Patent and Trademark Office Re. U.S. Appl. No. 13/424,553.

(Continued)

*Primary Examiner* — Shawquia Jackson

(57) ABSTRACT

Compounds that can be used as openers or blockers of voltage-dependent potassium channels, and which are useful in the treatment of conditions such as central or peripheral nervous system disorders through the modulation of potassium ion flux through voltage-dependent potassium channels and/or depressing or enhancing cortical and/or peripheral neuron activity, compositions containing same and methods utilizing same are disclosed. Also disclosed are modulators of voltage-dependent potassium channels, which exhibit blocking of a TRPV1 channel, and hence are useful in the treatment of TRPV1-related conditions.

11 Claims, 15 Drawing Sheets
(6 of 15 Drawing Sheet(s) Filed in Color)

(56) References Cited

FOREIGN PATENT DOCUMENTS

| JP | 01-096158 | 4/1989 |
|---|---|---|
| JP | 05-132431 | 5/1993 |
| JP | 2002-509536 | 3/2002 |
| WO | WO 98/20864 | 5/1998 |
| WO | WO 99/01421 | 1/1999 |
| WO | WO 00/34248 | 6/2000 |
| WO | WO 00/61541 | 10/2000 |
| WO | WO 01/05392 | 1/2001 |
| WO | WO 01/09612 | 2/2001 |
| WO | WO 01/19406 | 3/2001 |
| WO | WO 01/47562 | 7/2001 |
| WO | WO 01/78721 | 10/2001 |
| WO | WO 01/93680 | 12/2001 |
| WO | WO 02/00167 | 1/2002 |
| WO | WO 02/36121 | 5/2002 |
| WO | WO 02/065977 | 8/2002 |
| WO | WO 02/074388 | 9/2002 |
| WO | WO 03/103602 | 12/2003 |
| WO | WO 04/000300 | 12/2003 |
| WO | WO 2004/026808 | 4/2004 |
| WO | WO 2004/035037 | 4/2004 |
| WO | WO 2004/052840 | 6/2004 |
| WO | WO 2005/009975 | 2/2005 |
| WO | WO 2006/042387 | 4/2006 |
| WO | WO 2006/117316 | 11/2006 |
| WO | WO 2008/012602 | 1/2008 |
| WO | WO 2008/029199 | 3/2008 |
| WO | WO 2009/007827 | 1/2009 |
| WO | WO 2009/037705 | 3/2009 |
| WO | WO 2009/037707 | 3/2009 |

OTHER PUBLICATIONS

Communication Pursuant to Article 94(3) EPC Dated Jan. 3, 2011 From the European Patent Office Re. Application No. 08808058.5.
Communication Pursuant to Article 94(3) EPC Dated Oct. 5, 2011 From the European Patent Office Re. Application No. 08808058.5.
Communication Pursuant to Article 94(3) EPC Dated Jun. 8, 2011 From the European Patent Office Re. Application No. 08808058.5.
Communication Pursuant to Article 94(3) EPC Dated Nov. 12, 2013 From the European Patent Office Re. Application No. 08808058.5.
Communication Pursuant to Article 94(3) EPC Dated Mar. 13, 2012 From the European Patent Office Re. Application No. 03753909.5.
Communication Pursuant to Article 94(3) EPC Dated Dec. 18, 2012 From the European Patent Office Re. Application No. 08808058.5.
Examination Report Dated Nov. 6, 2013 From the Government of India, Patent Office, Intellectual Property Building Re. Application No. 2531/CHENP/2008.
Examination Report Dated May 30, 2007 From the Government of India, Patent Office Re. Application No. 965/CHENP/2005.
International Preliminary Report on Patentability Dated Apr. 1, 2010 From the International Bureau of WIPO Re. Application No. PCT/IL2008/001255.
International Preliminary Report on Patentability Dated Apr. 1, 2010 From the International Bureau of WIPO Re. Application No. PCT/IL2008/001257.
International Search Report Dated Jun. 2, 2009 From the International Searching Authority Re. Application No. PCT/IL2008/001255.
International Search Report Dated Apr. 5, 2004 From the International Searching Authority Re. Application No. PCT/IL03/00855.
International Search Report Dated Mar. 6, 2009 From the International Searching Authority Re. Application No. PCT/IL2008/001257.
Notice of Allowance Dated Aug. 5, 2013 From the US Patent and Trademark Office Re. U.S. Appl. No. 13/424,553.
Notice of Allowance Dated Feb. 13, 2012 From the US Patent and Trademark Office Re. U.S. Appl. No. 12/591,090.
Notice of Allowance Dated Feb. 18, 2014 From the US Patent and Trademark Office Re. U.S. Appl. No. 12/452,353.
Office Action Dated Aug. 3, 2010 From the Israeli Patent Office Re. Application No. 168217 and Its Translation Into English.
Office Action Dated May 6, 2014 From the State Intellectual Property Office of the People's Republic of China Re. Application No. 200880117585.8 and its Translation into English.
Office Action Dated Jul. 16, 2012 From the State Intellectual Property Office of the People's Republic of China Re. Application No. 200880117585.8 and its Translation into English.
Office Action Dated May 27, 2010 From the Israeli Patent Office Re. Application No. 168217 and Its Translation Into English.
Office Action Dated Dec. 31, 2012 From the Israel Patent Office Re. Application No. 204617 and Its Translation Into English.
Official Action Dated Sep. 1, 2010 From the US Patent and Trademark Office Re. U.S. Appl. No. 12/591,090.
Official Action Dated Aug. 2, 2012 From the US Patent and Trademark Office Re. U.S. Appl. No. 13/424,553.
Official Action Dated Sep. 4, 2013 From the US Patent and Trademark Office Re. U.S. Appl. No. 12/452,353.
Official Action Dated Oct. 6, 2011 From the US Patent and Trademark Office Re. U.S. Appl. No. 12/452,353.
Official Action Dated Sep. 6, 2011 From the US Patent and Trademark Office Re. U.S. Appl. No. 12/591,090.
Official Action Dated Dec. 8, 2008 From the US Patent and Trademark Office Re. U.S. Appl. No. 11/110,669.
Official Action Dated Feb. 11, 2011 From the US Patent and Trademark Office Re. U.S. Appl. No. 12/452,353.
Official Action Dated Mar. 13, 2013 From the US Patent and Trademark Office Re. U.S. Appl. No. 13/424,553.
Official Action Dated Jul. 20, 2010 From the US Patent and Trademark Office Re. U.S. Appl. No. 12/591,090.
Official Action Dated Mar. 21, 2013 From the US Patent and Trademark Office Re. U.S. Appl. No. 12/452,353.
Official Action Dated Mar. 22, 2011 From the US Patent and Trademark Office Re. U.S. Appl. No. 12/591,090.
Official Action Dated Oct. 22, 2007 From the US Patent and Trademark Office Re. U.S. Appl. No. 11/110,669.
Official Action Dated Apr. 23, 2010 From the US Patent and Trademark Office Re. U.S. Appl. No. 12/591,090.
Official Action Dated Feb. 28, 2008 From the US Patent and Trademark Office Re. U.S. Appl. No. 11/110,669.
Official Action Dated Oct. 29, 2010 From the US Patent and Trademark Office Re. U.S. Appl. No. 12/452,353.
Search Report Dated Jul. 5, 2012 From the State Intellectual Property Office of the People's Republic of China Re. Application No. 200880117585.8 and its Translation into English.
Translation of Notice of Reason for Rejection Dated Jun. 8, 2010 From the Japanese Patent Office Re. Application No. 2004-544675.
Written Opinion Dated Jun. 2, 2009 From the International Searching Authority Re. Application No. PCT/IL2008/001255.
Written Opinion Dated Mar. 6, 2009 From the International Searching Authority Re. Application No. PCT/IL2008/001257.
Anonymous "Synthesis of Compounds", Supporting Text S1, XP007908469, p. 1-13, Dec. 26, 2007. Compounds 8, 11, 12, 13, 14, 15, 19, 20.
Baranauskas et al. "Kv3.4 Subunits Enhance the Repolarizing Efficiency of Kv3.1 Channels in Fast-Spiking Neurons", Nature Neuroscience, 6(3): 258-266, 2003.
Beilstein Database Beilstein, Beilstein Institute for Organic Chemistry, XP002516450, Database Accession No. Beilstein Registry No. 3410361, Apr. 2008. Abstract. & Levi et al., Journal of the Chemical Society, p. 1490, 1493, 1933.
Biervert et al. "A Potassium Channel Mutation in Neonatal Human Epilepsy", Science, 279: 403-406, Jan. 16, 1998.
Bonina et al. "Oligoethylene Ester Derivatives of Ketoprofen, Naxoroxen and Diclofenac as Oral Prodrugs: A Pharmacological Evaluation", Die Pharmazie, XP001539451, 57(8): 552-555, Aug. 1, 2002. Abstract, Compounds 3A-E, Table 4.
Butler et al. "Mslo, A Complex Mouse Gene Encoding "Maxi" Calcium-Activated Potassium Channels", Science, 261(5118): 221-225, 1993.
Congiu et al. "New Potential Anticancer Agents Based on the Anthranilic Acid Scaffold. Synthesis and Evaluation of Biological Activity", Journal of Medicinal Chemistry, XP007908449, 48(26): 8245-8252, Jan. 1, 2005. Fig.2, Tables 1-3.

(56) References Cited

OTHER PUBLICATIONS

Du et al. "Development Expression and Functional Characterization of the Potassium-Channel Subunit Kv3.1b in Parvalbumin-Containig Interneurons of the Hippocampus", The Journal of Neuroscience, 16(2): 506-518, 1996.
Fleming et al. "Synthesis of Non-Steroidal Antiinflammatory Drug Analogues for Selective Studies on the COX-II Enzyme", Journal of Labelled Compounds and Radiopharmaceuticals, 38(1): Jan. 13-18, 1996.
Fregnan et al. "Local Anti-Inflammatory Properties of Etoclofene. A New Fenamate Derivative", Pharmacology, XP009116638, 11(4): 213-219, Jan. 1, 1974. Abstract.
Heinemann et al. "Functional Characterization of Kv Channel ?-Subunits From Rat Brain", Journal of Physiology, 493(3): 625-633, 1996.
Jahnel et al. "Dual Expression of Mouse and Rat VRL-1 in the Dorsal Root Ganglion Derived Cell Line F-11 and Biochemical Analysis of VRL-1 After Heterologous Expression", European Journal of Biochemistry, 270: 4264-4271, 2003.
Joiner et al. "Formation of Intermediate-Conductance Calcium-Activated Potassium Channels by Interaction of Slack and Slo Subunits", Nature Neuroscience, 1: 462-469, 1998.
Jurman et al. "Visual Identification of Individual Transfected Cells for Electrophsyiology Uding Antibody-Coated Beads", Biotechniques, 17(5): 876-881, 1994. Abstract.
Kalgutkar et al. "Amide Derivatives of Meclofenamic Acid as Selective Cyclooxygenase-2 Inhibitors", Bioorganic & Medicinal Chemistry Letters, XP002319950, 12: 521-524, Jan. 1, 2002. Table 1, Compounds 1-3.
Kananura et al. "The New Voltage Gated Potassium Channel KCNQ5 and Neonatal Convulsions", Genetics of Nervous System Diseases, 11(9): 2063-2067, 2000.
Kubisch et al. "KCNQ4, A Novel Potassium Channel Expressed in Sensory Outer Hair Cells, is Mutated in Dominant Deafness", Cell, 96: 437-446, 1999.
Legrand et al. "Heterocyclic Sulfur Compounds. 1,2-Dihydro-3,1,2? 5-Benzothiazaphosphinine-2,4-Dihydrothiazoles (or Oxazoles)", Phosphorus and Sulfur and the Related Elements, 26(1): 111-117, 1986. Chemical Abstract, STN on the Web, IT Field [Online], Accession No. 106:32994, 1986.
Leppert et al. "Benign Familial Neonatal Convulsions Linked to Genetic Markers on Chromosome 20", Nature, 337(6208): 647-648, 1989. Abstract.
Liu et al. "Oxidative Stress and Potassium Channel Function", Clinical and Experimental Pharmacology and Physiology, 29(4): 305-311, 2002. Abstract.
Main et al. "Modulation of KCNQ2/3 Potassium Channels by the Novels Anticonvulsant Retigabine", Molecular Pharmacology, 58: 253-262, 2000.
Mayo Clinic Staff "Parkinson's Disease", Mayo Clinic Staff, Mayo Foundation for Medical Education and Research (MFMER), Retrieved From the Internet, 12 P., Feb. 15, 2011.
Meera et al. "Large Conductance Voltage- and Calcium-Dependent K+ Channel, A Distinct Member of Voltage-Dependent Ion Channels With Seven N-Terminal Transmembrane Segments (S0-S6), an Extracellular N Terminus, and an Intracellular (S9-S10) C Terminus", Proc. Natl. Acad. Sci. USA, 94: 14066-14071, 1997.
Passmore et al. "KCNQ/M Currents in Sensory Neurons: Significance for Pain Therapy", The Journal of Neuroscience, 23(18): 7227-7236, 2003.
Patini et al. "Bioisosterism: A Rational Approach in Drug Design", Chemical Reviews, 96: 3147-3176, 1996.
Pedarzani et al. "Control of Electrical Activity in Central Neurons by Modulating the Gating of Small Conductance Ca2+-Activated K+ Channels", The Journal of Biological Chemistry, XP001026430, 276(13): 9762-9769, Mar. 30, 2001. Abstract.
Peretz et al. "A Tale of Switched Functions: From Cyclooxygenase Inhibition to M-Channel Modulation in New Diphenylamine Derivatives", PLoS ONE (Public Library of Science), XP009116544, 2(12/e1332): 1-13, Dec. 26, 2007. Table 1.
Peretz et al. "Meclofenamic Acid and Diclofenac, Novel Templates of KCNQ2/Q3 Potassium Channel Openers, Depress Cortical Neuron Activity and Exhibit Anticonvulsant Properties", Molecular Pharmacology, 67(4): 1-14, 2005.
Riu-Wen et al. "Synthesis and Anti-Inflammatory Activity of Benzenesulfonylfuroxan-Coupled Diclofenac", Acta Pharmaceutica Sinica 36(11): 821-826, 2001. (with an abstract in English).
Robbins "KCNQ Potassium Channels: Physiology, Pathophysiology, and Pharmacology", Pharmacology & Therapeutics, 90(1): Apr. 1-19, 2001.
Sanguinetti et al. "Coassembly of k Sub V LQT1 and MinK (IsK) Proteins to Form Cardiac I Sub Ks Potassium Channel", Nature, 384(6604): 80-83, 1996.
Schreiber et al. "Slo3, A Novel PH-Sensitive K+ Channel From Mammalian Spermatocytes", The Journal of Biological Chemistry, 273(6): 3509-3516, 1998.
Shah et al. "Molecular Correlates of the M-Current in Cultured Rat Hippocampal Neurons", The Journal of Physiology, 544: 29-37, 2002.
Shi et al. "Beta Subunits Promote K+ Channel Surface Expression Through Effects Early in Biosynthesis", Neuron, 16: 843-852, 1996.
Syme et al. "Pharmacological Activation of Cloned Intermediate- and Small-Conductance Ca+-Activated K+ Channels", American Journal of Physiology and Cell Physiology, 278: C570-C581, 2000.
Tatulian et al. "Activation of Expressed KCNQ Potassium Currents and Native Neuronal M-Type Potassium Currents by the Anti-Convulsant Drug Retigabine", The Journal of Neuroscience, 21(15): 5535-5545, 2001.
Trishin et al. "Reaction of Pentafluorophenyl(Diphenyl)Phosphine With Nitrilimines", Russian Journal of General Chemistry, XP002516449, 71(3): 471-475, 2001.
Vercouillie et al. "Synthesis and In Vitro Evaluation of Novel Derivatives of Diphenylsulfide as Serotonin Transporter Ligands", Bioorganic & Medicinal Chemistry Letters, XP025106339, 16(5): 1297-1300, Mar. 1, 2006. p. 1297, Abstract, p. 1298, Scheme 1, Compounds 5a-9a, 5b-9b.
Wang et al. "KCNQ2 and KCNQ3 Potassium Channel Subunits: Molecular Correlates of the M-Channel", Science, 282: 1890-1893, 1998.
Wei et al. "Eight Potassium Channel Families Revealed by the C. Elegans Genome Project", Neuropharmacology, 35(7): 805-829, 1996.
Wickenden et al. "Characterization of KCNQ5/Q3 Potassium Channels Expressed in Mammalian Cells", British Journal of Pharmacology, 132: 381-384, 2001.
Wilson et al. "Hypoxia-Selective Antitumor Agents. 1. Relationships Between Structure, Redox Properties and Hypoxia-Selective Cytotoxicity for 4-Substituted Derivatives of Nitracrine", Journal of Medicinal Chemistry, XP001016258, 32: 23-30, Jan. 1, 1989. p. 24, 'Scheme I', Compounds III, V.
Yang et al. "Functional Expression of Two KvLQT1-Related Potassium Channels Responsible for an Inherited Idiopathic Epilepsy", The Journal of Biological Chemistry, 273(31): 19419-19423, 1998.
Yue et al. "KCNQ/M Channels Control Spike Afterdepolarization and Burst Generation in Hippocampal Neurons", The Journal of Neuroscience, 24(19): 4614-4624, 2004.

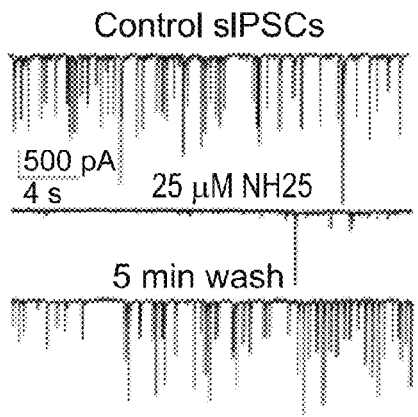
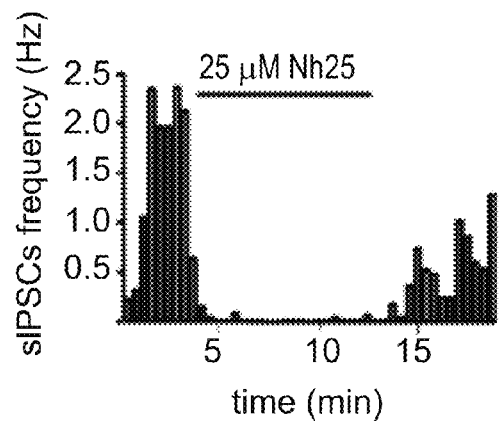
FIG. 6A
FIG. 6B
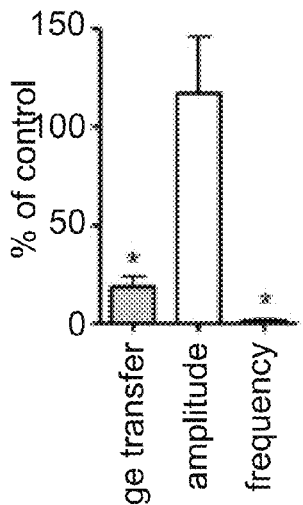
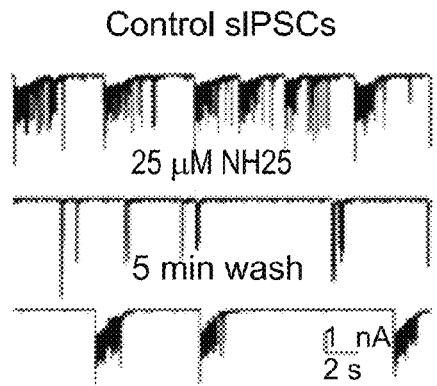
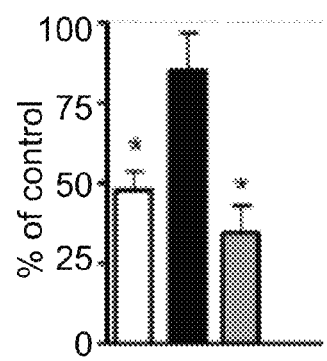
FIG. 6C
FIG. 6D
FIG. 6E
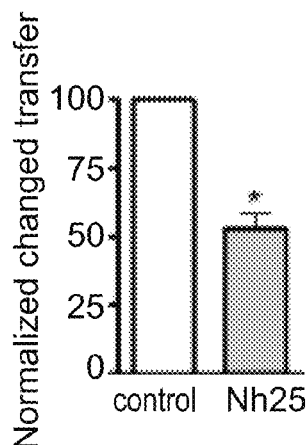
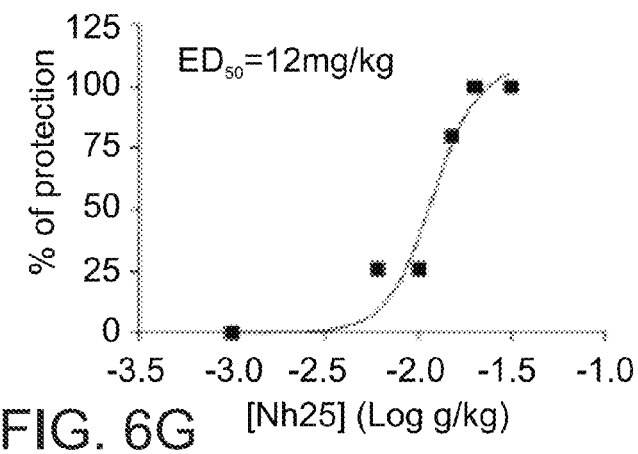
FIG. 6F
FIG. 6G

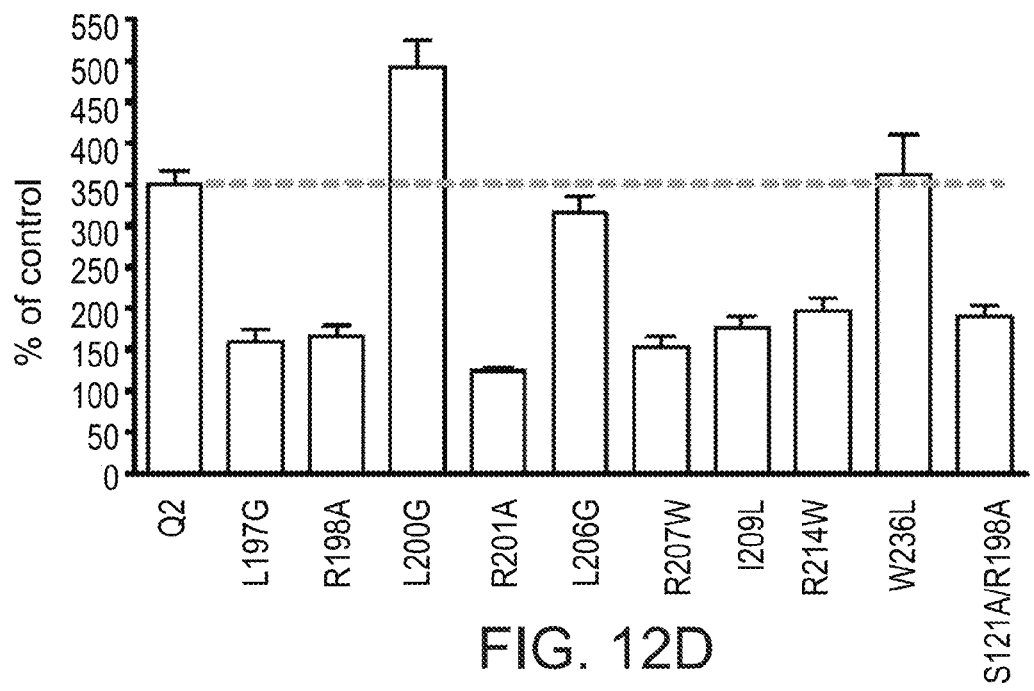
FIG. 12D
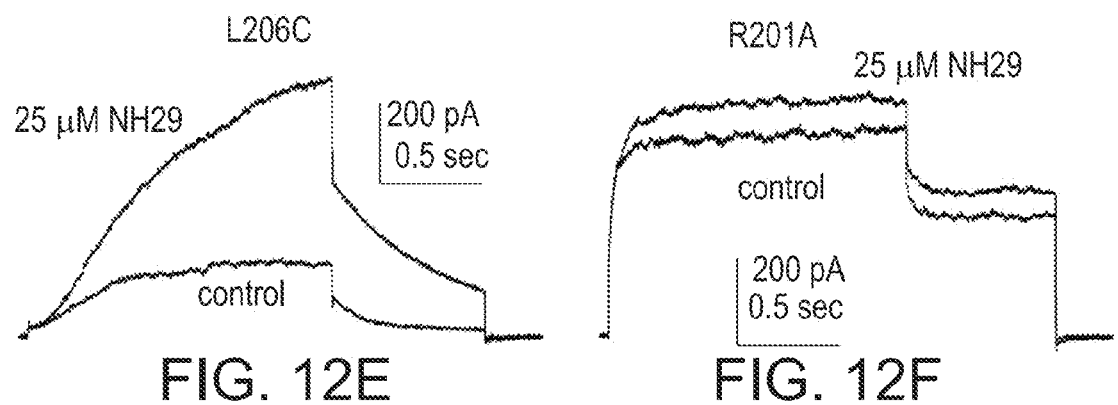
FIG. 12E
FIG. 12F

N-PHENYL ANTHRANILIC ACID DERIVATIVES AND USES THEREOF

RELATED APPLICATIONS

This application is a continuation of U.S. patent application Ser. No. 12/452,353 filed on Dec. 28, 2009, which is a National Phase of PCT Patent Application No. PCT/IL2008/001257 having International filing date of Sep. 18, 2008, which claims the benefit of priority under 35 USC §119(e) of U.S. Provisional Patent Application Nos. 60/996,398 filed on Nov. 15, 2007 and 60/960,215 filed on Sep. 20, 2007. The contents of the above applications are all incorporated herein by reference.

FIELD AND BACKGROUND OF THE INVENTION

The present invention, in some embodiments thereof, relates to novel derivatives of diphenylamine and their use in the treatment of various pathologies, including pathologies related to potassium ion flux through voltage-dependent potassium channels and/or cortical and peripheral neuron activity, and pathologies related to TRPV1.

Ion channels are cellular proteins that regulate the flow of ions, including calcium, potassium, sodium and chloride ions, into and out of cells. Among the ion channels, potassium channels are the most ubiquitous and diverse, being found in a variety of animal cells such as nervous, muscular, glandular, immune, reproductive and epithelial tissue, and affect a variety of fundamental biological processes. Upon opening of potassium channels, the outward flow of potassium ions makes the interior of the cell more negative, counteracting depolarizing voltages applied to the cell. These channels are regulated, e.g., by calcium sensitivity, voltage-gating, second messengers, extracellular ligands and ATP-sensitivity.

The physiologic M-current is a non-inactivating potassium current found in many neuronal cell types. In each cell type, it is dominant in controlling membrane excitability by being the only sustained current in the range of action potential initiation. Modulation of M-current has dramatic effects on neuronal excitability. It can be modulated by a large array of receptor types, and the modulation can occur either by suppression (deactivation, blocking) or enhancement (activation, opening). Channels enabling M-current flow are often referred to herein and in the art as M-channels.

Potassium channels have been associated with a number of physiological processes, including regulation of heartbeat, dilation of arteries, release of insulin, excitability of nerve cells, and regulation of renal electrolyte transport. Modulators of potassium channels are therefore prime pharmaceutical candidates, and the development of new modulators as therapeutic agents is an on-going research effort.

Potassium channels modulators are divided to channel-openers and channel-blockers. A potassium channel opener that has gained much attention is retigabine (N-(2-amino-4-(4-fluorobenzylamino)-phenyl)carbamic acid ethyl ester). Retigabine is highly selective for KCNQ-type potassium channels consisting of the subunits KCNQ2 and KCNQ3, which was first described in 1993 in EP0554543. Use of retigabine for treating neuropathic pain was disclosed in, for example, U.S. Pat. No. 6,117,900 and EP1223927. Compounds related to retigabine have also been proposed for use as potassium channel modulators, see, for example U.S. patent application Ser. No. 10/022,579 and U.S. Pat. No. 6,472,165.

Other KCNQ potassium channel modulators have been described in, for example, U.S. patent application Ser. No. 10/075,521, which teaches 2,4-disubstituted pyrimidine-5-carboxamide derivatives as KCNQ potassium channel modulator; U.S. patent application Ser. No. 10/160,582, which teaches cinamide derivatives as KCNQ potassium channel modulators; U.S. Pat. No. 5,565,483 and U.S. patent application Ser. Nos. 10/312,123, 10/075,703 and 10/075,522, which teach 3-substituted oxindole derivatives as KCNQ potassium channel modulators; U.S. Pat. No. 5,384,330, which teaches 1,2,4-triamino-benzene derivatives as KCNQ potassium channel modulators; and U.S. Pat. No. 6,593,349 which teaches bisarylamines derivatives as KCNQ potassium channel modulators. U.S. Pat. No. 6,291,442 teaches compounds comprising two or three aromatic rings having a free carboxyl or a carboxyl being linked, via an ester bond, to a lower alkyl ester, attached to one of the rings, for the modulation of Shaker class of voltage gated potassium channels.

It has been shown that two chemically-related non-steroidal anti-inflammatory drugs (NSAIDs), diclofenac and meclofenamic acid, exhibit potassium channel modulation activity as openers of Kv7.2/3 (KCNQ2/3) channels [1], and further have been shown to underlie the neuronal M-currents of these so called M-channels. Pharmacological targeting of M-channels is of great clinical importance. While openers of these channels demonstrate a therapeutic potential for the treatment of neuronal hyperexcitability like migraine, epilepsy and neuropathic pain, blockers of these channels are potentially useful for the treatment of memory deficits and Alzheimer's disease[2, 3].

Derivatives of such NSAIDs have been studied as M-channels modulator. WO2004/035037 and U.S. Patent Application No. 20050250833, which are incorporated by reference as if fully set forth herein, teach derivatives of N-phenylanthranilic acid and 2-benzimidazolone as potassium channel openers, especially voltage-dependent potassium channels such as KCNQ2 channel, KCNQ3 channels and KCNQ2/3 channels, as well as neuron activity modulators.

Transient receptor potential vanilloid type 1 (TRPV1) receptor is a ligand-gated non-selective cation channel activated by heat (typically above 43° C.), low pH (<6) and endogenous lipid molecules such as anandamide, N-arachidonoyl-dopamine, N-acyl-dopamines and products of lipoxygenases (e.g., 12- and 15-(S)-HPETE) termed endovanilloids. Apart from peripheral primary afferent neurons and dorsal root ganglia, TRPV1 receptor is expressed throughout the brain. Recent evidence shows that TRPV1 receptor stimulation by endocannabinoids or by capsaicin leads to analgesia and this effect is associated with glutamate increase and the activation of OFF cell population in the rostral ventromedial medulla (RVM).

TRPV1 has also been found to be involved in the regulation of body temperature, anxiety and mediation of long term depression (LTD) in the hippocampus. TRPV1 channels are also located on sensory afferents which innervate the bladder. Inhibition of TRPV1 has been shown to ameliorate urinary incontinence symptoms.

TRPV1 modulators have been described in, for example, WO 2007/054480, which teaches the effect of 2-(benzimidazol-1-yl)-acetamide derivatives in the treatment of TRPV1 related diseases. WO 2008/079683 teaches compounds being a conjugated two ring system of cyclohexyl and phenyl for inhibiting TRPV1 receptor. EP01939173 teaches O-substituted-dibenzyl urea- or thiourea-derivatives as TRPV1 receptor antagonists. WO 2008/076752 teaches benzoimidazole compounds as potent TRPV1 modulators and EP01908753 teaches TRPV1 modulators being heterocyclidene acetamide derivatives.

SUMMARY OF THE INVENTION

The present invention, in some embodiments thereof, relates to compounds that are effective potassium channel modulators, and more specifically, are openers or blockers of voltage-dependent potassium channels such as KCNQ2 channel, KCNQ3 channel and KCNQ2/3 channel, which can be used as pharmaceuticals to treat medical conditions that require opening or blocking these channels. The present invention, in some embodiments thereof, further relates to compounds which are TRPV1 modulators, which can be used as pharmaceuticals to treat medical conditions which require blocking this channel.

The design and activity of the compounds described herein stemmed from a structure-activity relationship (SAR) study which accentuated the chemical and structural determinants for potassium channel binding and modulation as openers and/or blockers. The compounds described herein are structurally based on carboxylic derivatives of diphenylamine, such as 2-(phenylamino)benzoic acid and 2-(2-(phenylamino)phenyl)acetic acid, while the potassium channel openers are particularly based on derivatives having one or more electron-withdrawing substituents on one or both the phenyl rings of the diphenylamine moiety and the potassium channel blockers are derivatized by, for example, replacing functionalities such as hydroxyl groups with other groups. In addition to modulating potassium channels, some of the compounds described herein were found to exhibit modulation (e.g., blocking) of TRPV1 channel.

Thus, according to an aspect of some embodiments of the present invention there is provided a compound having the general Formula I:

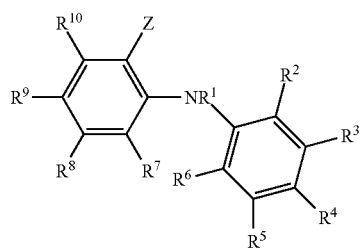

Formula I or a pharmaceutically acceptable salt thereof,
wherein,
Z is an A-G(=K)—X—Y group,
A is alkyl or absent;
G is selected from the group consisting of C, S and PRa;
K is selected from the group consisting of O and S;
X is selected from the group consisting of O, S and NRb, or absent; and
Y is selected from the group consisting of hydrogen, alkyl, hydroxyalkyl, cycloalkyl, aryl and a polyalkylene glycol moiety,
$R^1$ is selected from the group consisting of hydrogen, alkyl, cycloalkyl or aryl;
each of $R^2$, $R^3$, $R^4$, $R^5$, $R^6$, $R^7$, $R^8$, $R^9$ and $R^{10}$ is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$ or, alternatively, at least two of $R^2$, $R^3$, $R^4$, $R^5$ and $R^6$, and/or of $R^7$, $R^8$, $R^9$ and $R^{10}$ form a five- or six-membered aromatic, heteroaromatic, alicyclic or heteroalicyclic ring, and each of Ra and Rb, is independently selected from the group consisting of hydrogen, alkyl, cycloalkyl and aryl, provided that at least one of $R^2$, $R^3$, $R^8$, $R^9$ and $R^{10}$ is an electron-withdrawing group.

According to some embodiments of the invention, at least two of $R^2$, $R^3$, $R^4$, $R^5$, $R^6$, $R^7$, $R^8$, $R^9$ and $R^{10}$ are electron-withdrawing groups.

According to some embodiments of the invention, at least one of $R^7$, $R^8$, $R^9$ and $R^{10}$ is an electron-withdrawing group.

According to some embodiments of the invention, least one of $R^7$, $R^8$, $R^9$ and $R^{10}$ is an electron-withdrawing group and at least one of $R^2$, $R^3$, $R^4$, $R^5$ and $R^6$ is an electron withdrawing group.

According to some embodiments of the invention, $R^9$ is an electron-withdrawing group.

According to some embodiments of the invention, at least one of $R^9$ and $R^7$ is an electron withdrawing group.

According to some embodiments of the invention, at least one $R^9$, $R^7$ and $R^4$ is an electron withdrawing group.

According to some embodiments of the invention, the electron-withdrawing group is nitro.

According to some embodiments of the invention, Y in a compound having the general Formula I is selected from the group consisting of hydroxyalkyl and a polyalkylene glycol moiety.

According to some embodiments of the invention, the polyalkylene glycol moiety has a general formula II:

$$[(CH_2)m\text{-}O]n\text{-}R^{17}$$  Formula II

Wherein each of m and n is independently an integer of 1-10; and $R^{17}$ is hydrogen, alkyl, cycloalkyl or aryl.

According to some embodiments of the invention, G is C, K is O, each of $R^2$, $R^3$, $R^4$, $R^5$ and $R^6$ is independently selected from the group consisting of hydrogen, alkyl, halo and trihaloalkyl; and each of $R^7$, $R^8$, $R^9$ and $R^{10}$ is hydrogen.

According to some embodiments of the invention, the compound presented herein is selected from the group consisting of NH24, NH25, NH28, NH29, NH30 and NH31.

According to another aspect of some embodiments of the present invention there is provided a process of preparing the compounds presented herein, the process is effected by reacting a compound having the general Formula I*,

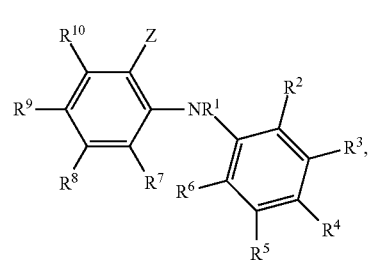

Formula I* wherein,
Z is an A-G(=K)—X—Y group;
A is alkyl or absent;
G is selected from the group consisting of C, S and PRa;
K is selected from the group consisting of O and S;
X is selected from the group consisting of NRb, S or absent; and Y is selected from the group consisting of hydrogen, alkyl, hydroxyalkyl, cycloalkyl, aryl and a polyalkylene glycol moiety, $R^1$ is selected from the group consisting of hydrogen, alkyl, cycloalkyl or aryl;

each of $R^2$, $R^3$, $R^4$, $R^5$, $R^6$, $R^7$, $R^8$, $R^9$ and $R^{10}$, is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$ or, alternatively, at least two of $R^2$, $R^3$, $R^4$, $R^5$ and/or $R^6$, of $R^7$, $R^8$, $R^9$ and $R^{10}$ form a five-membered or six-membered aromatic, heteroaromatic, alicyclic or heteroalicyclic ring; and each of Ra and Rb is independently selected from the group consisting of hydrogen, alkyl, cycloalkyl and aryl;

with an agent capable of substituting one or more of $R^2$, $R^3$, $R^4$, $R^5$, $R^6$, $R^7$, $R^8$, $R^9$ and $R^{10}$ by an electron-withdrawing group, to thereby obtain the compound having the general Formula I.

According to another aspect of some embodiments of the present invention there is provided a method of opening a voltage-dependent potassium channel and/or of depressing cortical and/or peripheral neuron activity; the method is effected by administering to the subject in need thereof a therapeutically effective amount of the compound presented herein, thereby opening the voltage-dependent potassium channel.

According to some embodiments of the invention, the compound forms a part of a pharmaceutical composition which further includes a pharmaceutically acceptable carrier.

According to another aspect of some embodiments of the present invention there is provided a use of the compound presented herein in the manufacture of a medicament for treating of a condition wherein opening a voltage-dependent potassium channel and/or in depressing cortical and/or peripheral neuron activity is beneficial.

According to another aspect of some embodiments of the present invention there is provided a pharmaceutical composition which includes, as an active ingredient, the compound as presented herein and a pharmaceutically acceptable carrier.

According to some embodiments of the invention, the composition is packaged in a packaging material and identified in print, in or on the packaging material, for use in opening a voltage-dependent potassium channel and/or of depressing cortical and/or peripheral neuron activity.

According to some embodiments of the invention, the voltage-dependent potassium channel includes a KCNQ2 channel and/or a KCNQ3 channel and/or a KCNQ2/3 channel.

According to some embodiments of the invention, opening of the voltage-dependent potassium channel is for a treatment of a condition or disorder selected from the group consisting of epilepsy, ischemic stroke, migraine, ataxia, myokymia, neurogenic pain, neuropathic pain, Parkinson's disease, bipolar disorder, trigeminal neuralgia, spasticity, mood disorder, psychotic disorder, schizophrenia, brain tumor, hearing and vision loss, anxiety and a motor neuron disease.

According to some embodiments of the invention, depressing the cortical and/or peripheral neuron activity is for a treatment of a condition or disorder selected from the group consisting of epilepsy, ischemic stroke, migraine, ataxia, myokymia, neurogenic pain, neuropathic pain, Parkinson's disease, bipolar disorder, trigeminal neuralgia, spasticity, mood disorder, psychotic disorder, schizophrenia, brain tumor, hearing and vision loss, anxiety and a motor neuron disease.

According to some embodiments, the compounds presented herein are capable of blocking a TRPV1 channel, and, further according to some embodiments, these compounds do not modulate an activity of TRPV6 channel.

According to another aspect of some embodiments of the present invention there is provided a method of blocking a voltage-dependent potassium channel and/or enhancing a cortical and/or peripheral neuron activity, the method is effected by administering to the subject in need thereof a therapeutically effective amount of a compound having a general Formula III:

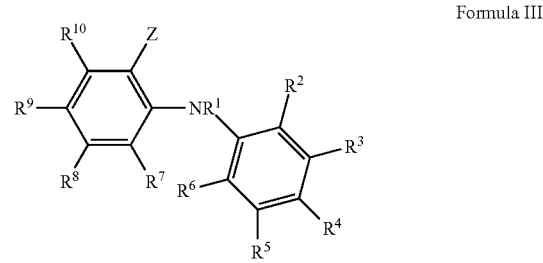

Formula III or a pharmaceutically acceptable salt thereof,
wherein,
Z is an A-G(=K)—X—Y group,
A is alkyl or absent;
G is selected from the group consisting of C, S and PRa;
K is selected from the group consisting of O and S;
X is selected from the group consisting of NRb, S or absent; and
Y is selected from the group consisting of alkyl, aryl, cycloalkyl, heteroalicyclic and a positively charged group, with the proviso that Y does not contain a hydroxy group;

$R^1$ is selected from the group consisting of hydrogen, alkyl, cycloalkyl or aryl;

each of $R^2$, $R^3$, $R^4$, $R^5$, $R^6$, $R^7$, $R^8$, $R^9$ and $R^{10}$, is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$ or, alternatively, at least two of $R^2$, $R^3$, $R^4$, $R^5$ and/or $R^6$, of $R^7$, $R^8$, $R^9$ and $R^{10}$ form a five- or six-membered aromatic, heteroaromatic, alicyclic or heteroalicyclic ring; and each of Ra and Rb is independently selected from the group consisting of hydrogen, alkyl, cycloalkyl and aryl.

According to another aspect of some embodiments of the present invention there is provided a pharmaceutical composition which includes, as an active ingredient, a compound having a general Formula III:

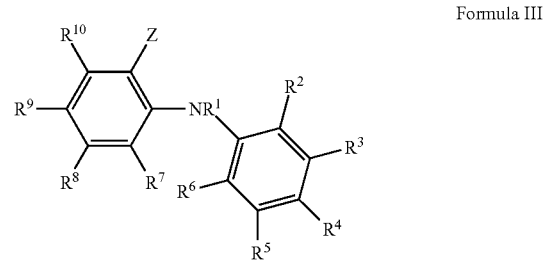

Formula III a pharmaceutically acceptable salt thereof, wherein:

Z is an A-G(=K)—X—Y group,

A is alkyl or absent;

G is selected from the group consisting of C, S and PRa;

K is selected from the group consisting of O and S;

X is selected from the group consisting of NRb, S or absent; and

Y is selected from the group consisting of alkyl, aryl, cycloalkyl, heteroalicyclic and a positively charged group, with the proviso that Y does not contain a hydroxy group;

$R^1$ is selected from the group consisting of hydrogen, alkyl, cycloalkyl or aryl;

each of $R^2$, $R^3$, $R^4$, $R^5$, $R^6$, $R^7$, $R^8$, $R^9$ and $R^{10}$, is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$ or, alternatively, at least two of $R^2$, $R^3$, $R^4$, $R^5$ and/or $R^6$, of $R^7$, $R^8$, $R^9$ and $R^{10}$ form a five- or six-membered aromatic, heteroaromatic, alicyclic or heteroalicyclic ring;

each of Ra and Rb is independently selected from the group consisting of hydrogen, alkyl, cycloalkyl and aryl, and wherein the composition is packaged in a packaging material and identified in print, in or on the packaging material, for use in blocking a voltage-dependent potassium channel.

According to another aspect of some embodiments of the present invention there is provided a use of the compound having the general Formula III as presented herein in the manufacture of a medicament for treating of a condition wherein blocking a voltage-dependent potassium channel is beneficial.

According to some embodiments of the invention, Y in compound having the general Formula III is selected from the group consisting of alkyl, heteroalicyclic and a positively charged group.

According to some embodiments of the invention, the alkyl is isobutyl.

According to some embodiments of the invention, the heteroalicyclic is 2,3-epoxypropyl.

According to some embodiments of the invention, the positively charged group is an ammonium group.

According to some embodiments of the invention, the voltage-dependent potassium channel comprises a KCNQ2 channel and/or a KCNQ3 channel and/or a KCNQ2/3 channel.

According to some embodiments of the invention, blocking of the voltage-dependent potassium channel is for a treatment of a cognitive condition or disorder.

According to some embodiments of the invention, the cognitive condition or disorder is selected from the group consisting of Alzheimer's disease, age-related memory loss, a memory deficit, a memory deficit related to brain injury or a post-stroke event and a learning deficiency.

According to an aspect of some embodiments of the present invention there is provided a method of blocking a voltage-dependent potassium channel, the method is effected by administering to a subject in need thereof a therapeutically effective amount of a compound capable of interacting with a hydrophobic binding pocket in a voltage sensitive domain of the potassium channel, while not interacting with at least one electrophilic binding site in the voltage sensitive domain.

According to some embodiments of the invention, the compound is capable of interacting with an externally accessible surface of the voltage sensitive domain at the groove formed by the interface between an S4 helix and S1-S2 in the voltage sensitive domain, and further of trapping the voltage sensitive domain in an inward resting conformation thereof.

According to an aspect of some embodiments of the present invention there is provided a method of opening a voltage-dependent potassium channel, the method is effected by administering to a subject in need thereof a therapeutically effective amount of a compound capable of interacting with a hydrophobic binding pocket and with at least two electrophilic binding sites in a voltage sensitive domain of the potassium channel.

According to some embodiments of the invention, the compound is capable of interacting with an externally accessible surface of the voltage sensitive domain at the groove formed by an interface between a S4 helix and S1-S2 in the voltage sensitive domain, and further of trapping the voltage sensitive domain in an outward activated conformation thereof.

According to an aspect of some embodiments of the present invention there is provided a method of blocking a transient receptor potential vanilloid 1 (TRPV1) in a subject in need thereof, the method comprising administering to the subject a therapeutically effective amount of a compound having general Formula IV:

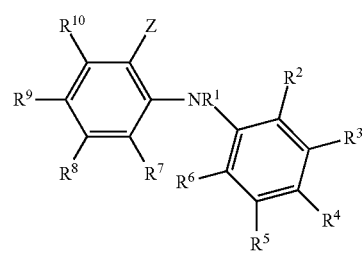

Formula IV wherein:

Z is an A-G(=K)—X—Y group, and wherein:

A is alkyl or absent;

G is selected from the group consisting of C, S and PRa;

K is selected from the group consisting of O and S;

X is selected from the group consisting of NRb, O, S or absent; and

Y is selected from the group consisting of hydrogen, alkyl, hydroxyalkyl, cycloalkyl, heteroalicyclic, aryl and a polyalkylene glycol residue, $R^1$ is selected from the group consisting of hydrogen, alkyl, cycloalkyl or aryl;

each of $R^2$, $R^3$, $R^4$, $R^5$, $R^6$, $R^7$, $R^8$, $R^9$ and $R^{10}$ is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, an electron-withdrawing group, amino and —$NR^{15}R^{16}$, or, alternatively, at least two of $R^2$, $R^3$, $R^4$, $R^5$ and $R^6$, of $R^7$, $R^8$, $R^9$ and $R^{10}$ form a five- or six-membered aromatic, heteroaromatic, alicyclic or heteroalicyclic ring;

$R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring; and each of the Ra and Rb is selected from the group consisting of hydrogen, alkyl, cycloalkyl and aryl.

According to an aspect of some embodiments of the present invention there is provided a use if a compound having general Formula IV, as described herein, in the manufacture of a medicament for blocking Transient receptor potential vanilloid 1 (TRPV1) in a subject in need thereof.

According to an aspect of some embodiments of the present invention there is provided a pharmaceutical composition comprising a compound having general Formula IV, as described herein, and a pharmaceutically acceptable carrier, the composition being packaged and identified in print, in or on the packaging material, for use in blocking Transient receptor potential vanilloid 1 (TRPV1).

According to some embodiments of the invention, Y is selected from the group consisting of hydroxyalkyl and a polyalkylene glycol moiety.

According to some embodiments of the invention, the polyalkylene glycol moiety has a general formula II, as described herein.

According to some embodiments of the invention, G is C; K is O; each of $R^2$, $R^3$, $R^4$, $R^5$ and $R^6$ is independently selected from the group consisting of hydrogen, alkyl, halo and trihaloalkyl; and each of $R^7$, $R^8$, $R^9$ and $R^{10}$ is hydrogen.

According to some embodiments of the invention, at least one of the $R^2$, $R^3$, $R^4$, $R^5$, $R^6$, $R^7$, $R^8$, $R^9$ and $R^{10}$ is an electron-withdrawing group, as described herein.

According to some embodiments of the invention, the compound is NH29.

According to some embodiments of the invention, the compound does not modulate TRPV6.

According to some embodiments of the invention, blocking the TRPV1 is for the treatment of a TRPV1 related disorder selected from the group consisting of epilepsy, pain related conditions such as neurogenic pain, neuropathic pain, allodynia, pain associated with inflammation, bipolar disorder, mood disorder, psychotic disorder, schizophrenia, anxiety and a motor neuron disease, bladder overactivity and urinary incontinence.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
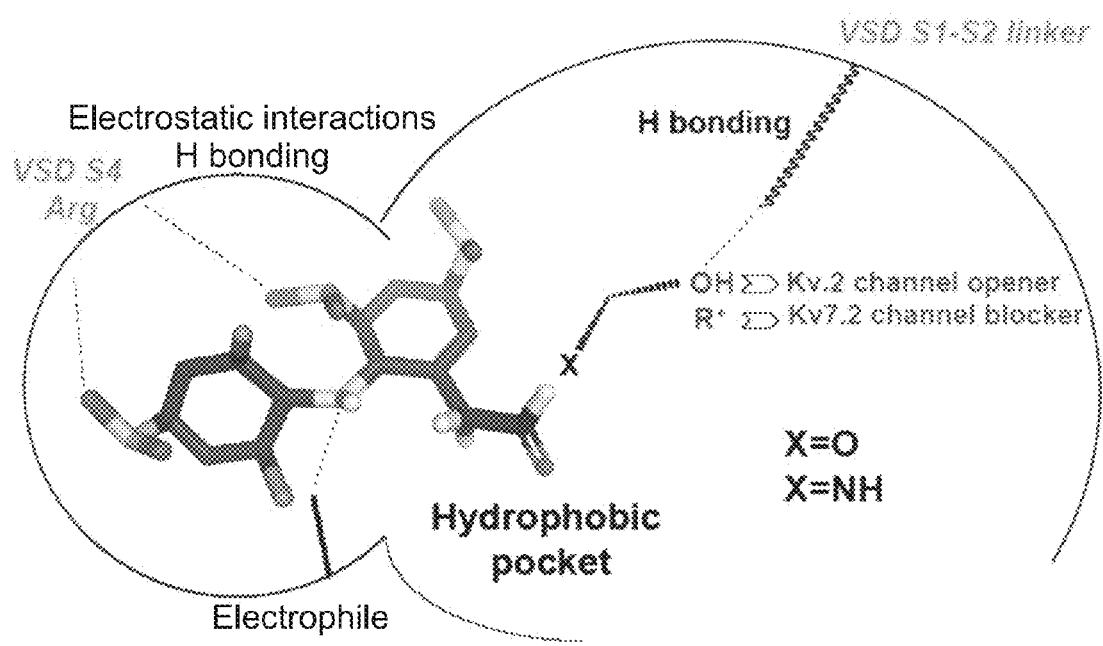
Figure 2A:
Figure 2B:
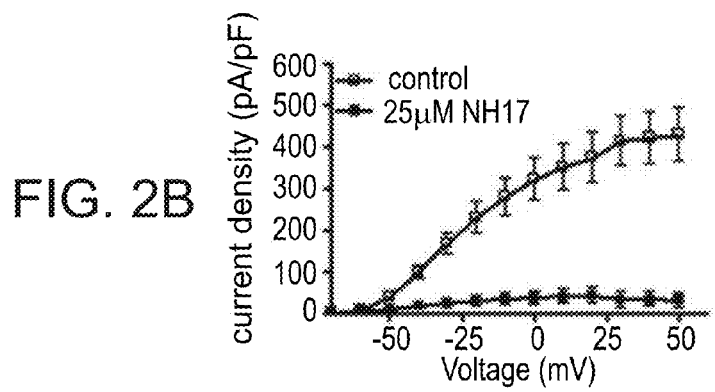
Figure 2C:
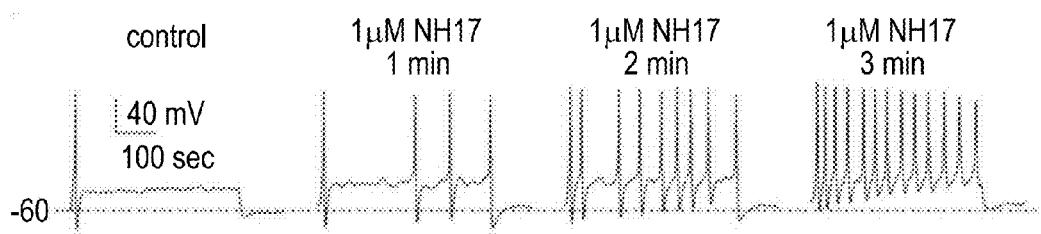
Figure 2D:
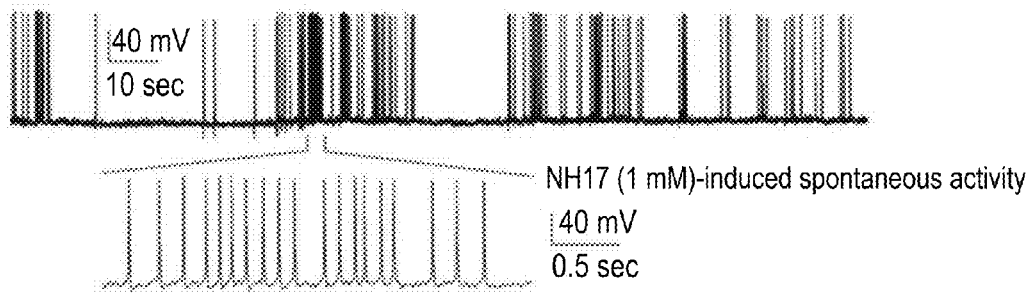
Figure 3A:
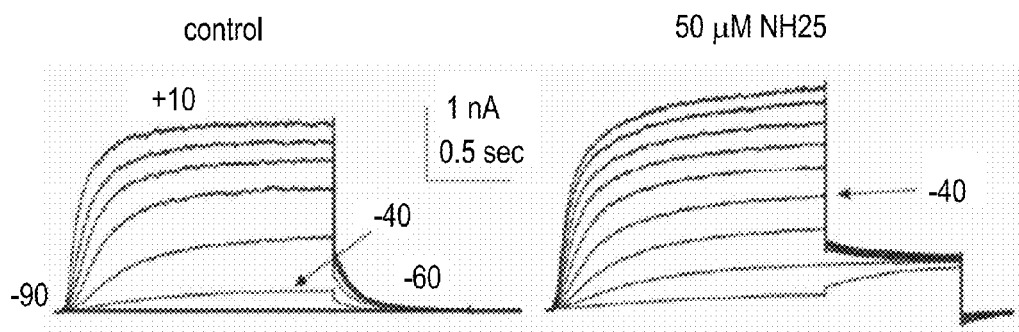
Figure 3B:
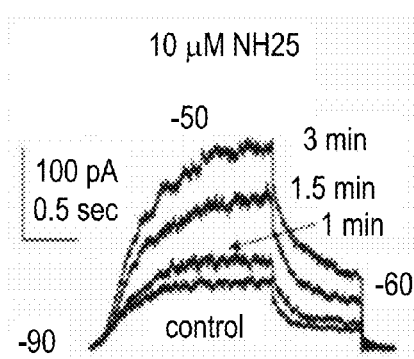
Figure 3C:
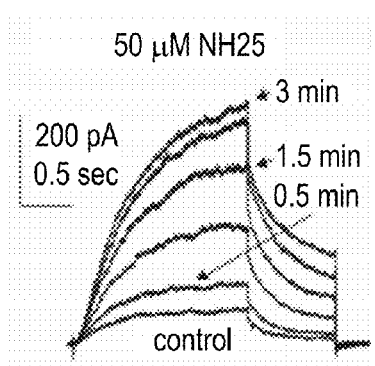
Figure 3D:
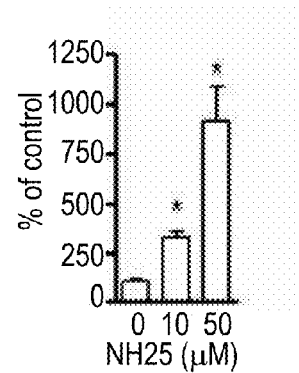
Figure 3E:
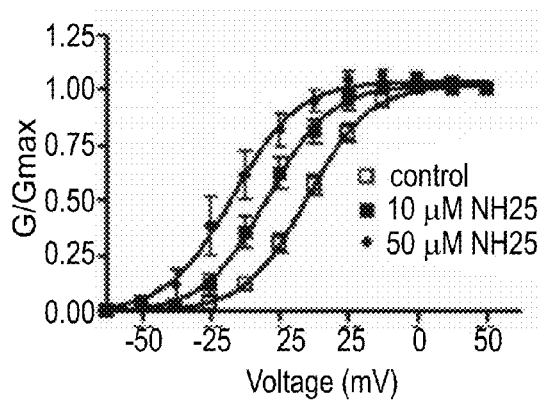
Figure 3F:
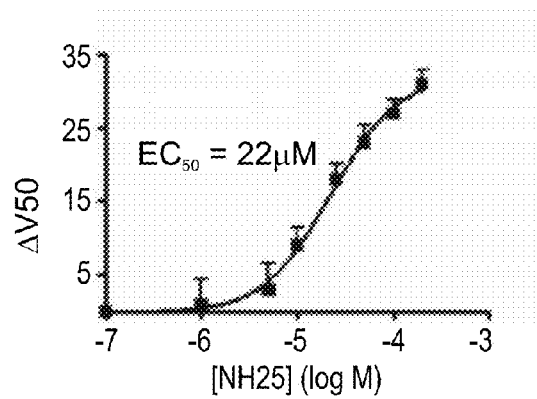
Figures 4A, 4B:
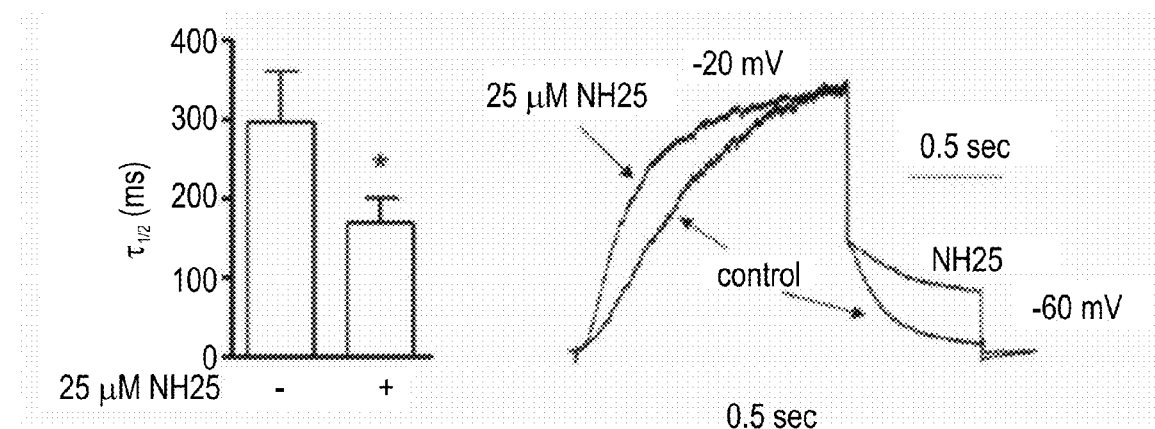
Figures 4C, 4D:
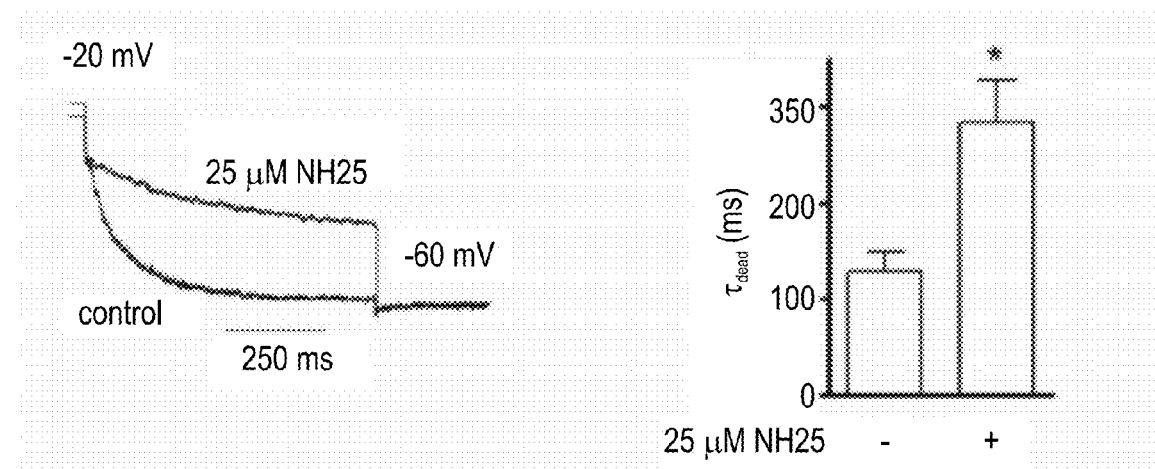
Figure 5A:
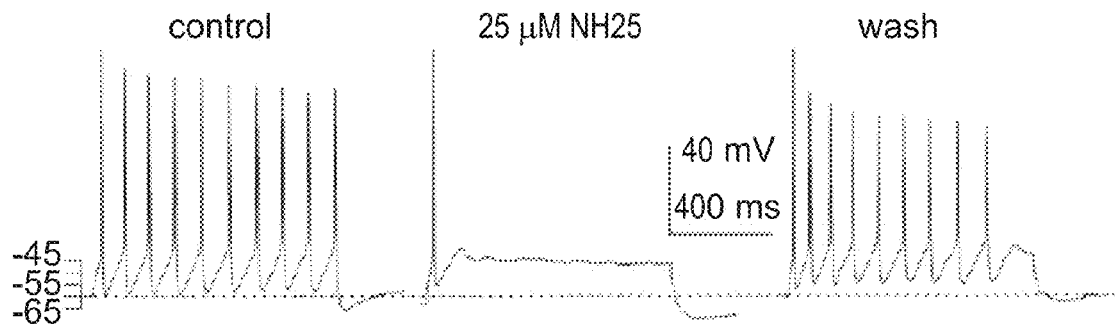
Figures 5B, 5C:
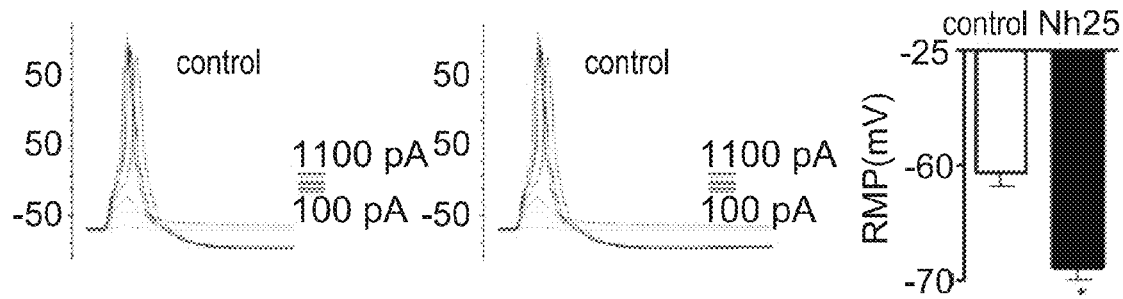
Figure 5D:
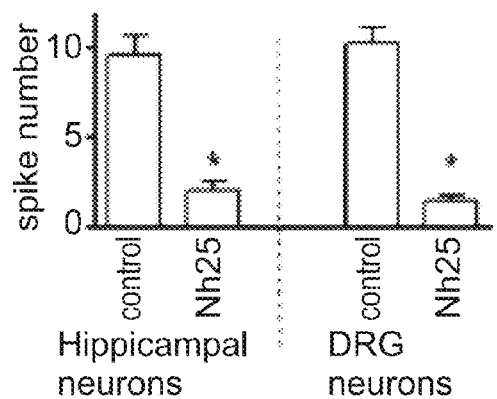
Figure 5E:
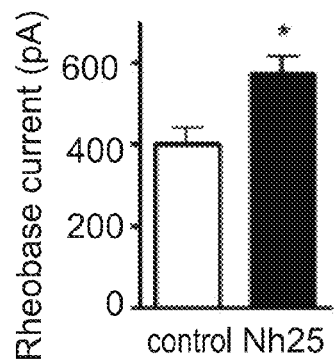
Figure 7A:
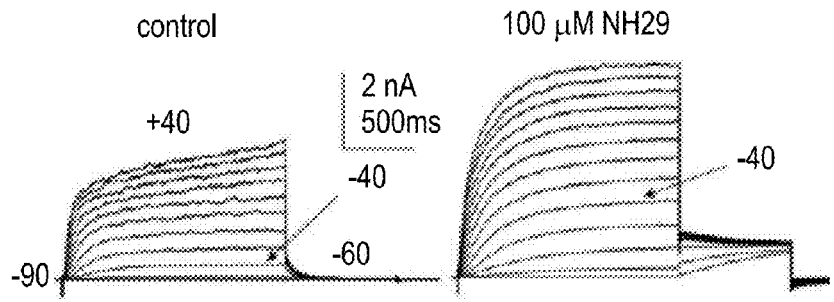
Figure 7B:
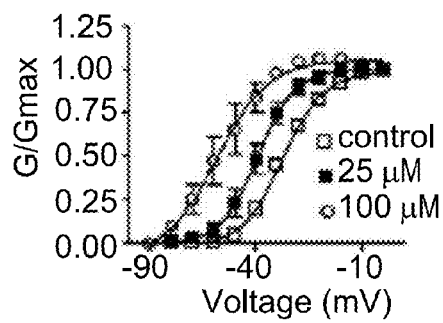
Figure 7C:
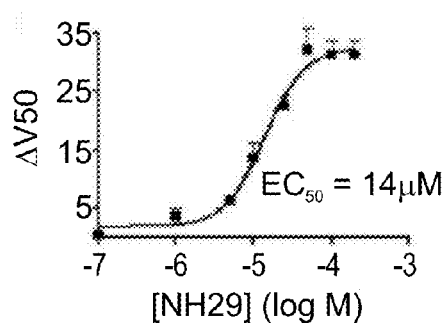
Figure 7D:
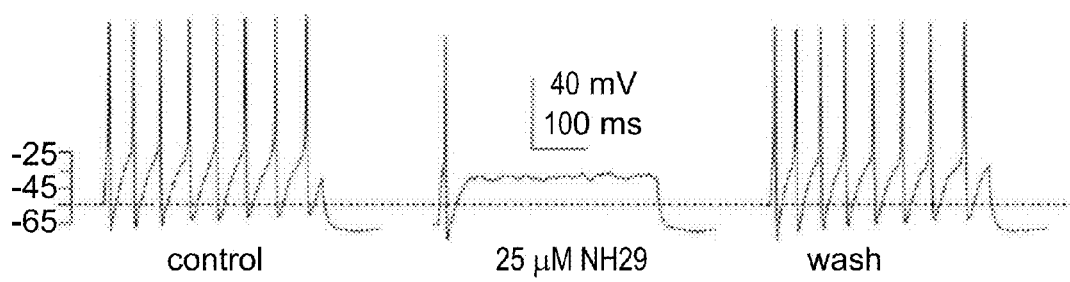
Figure 7E:
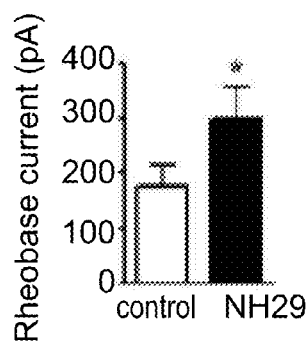
Figure 7F:
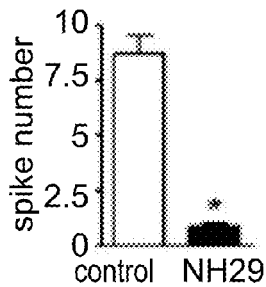
Figure 7G:
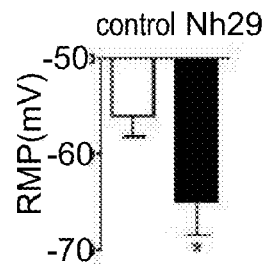
Figure 8:
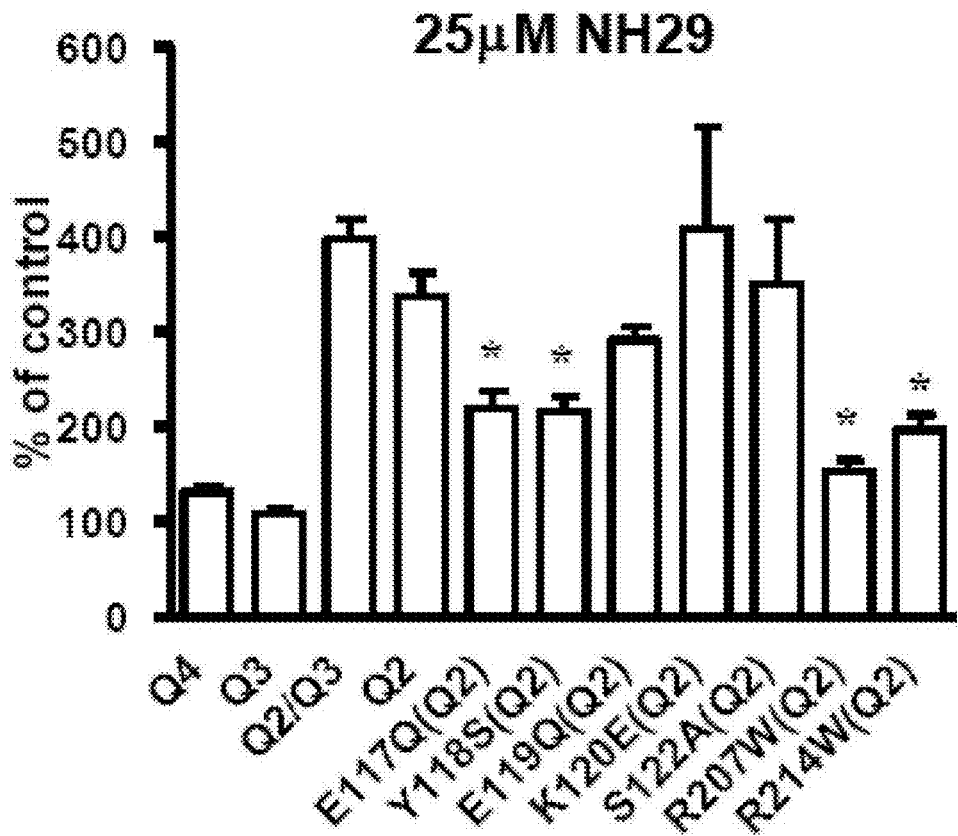
Figure 9:
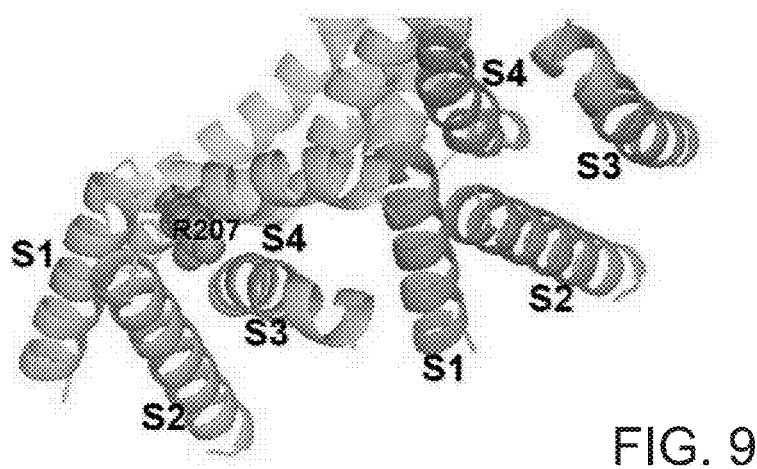
Figure 10A:
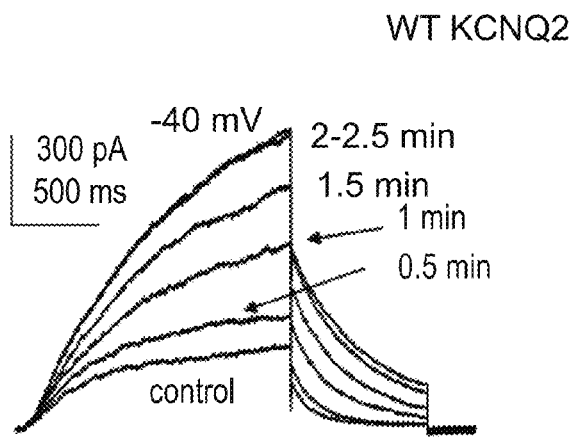
Figure 10B:
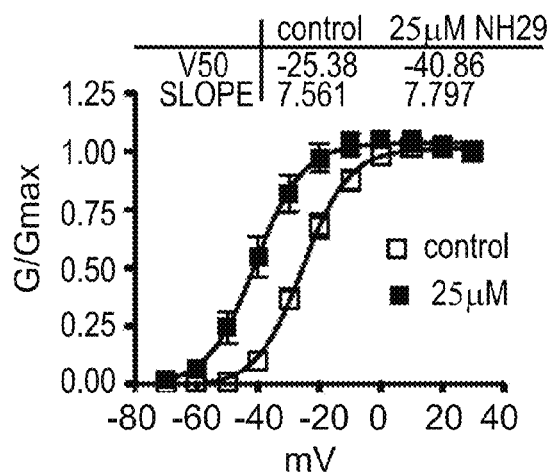
Figure 10C:
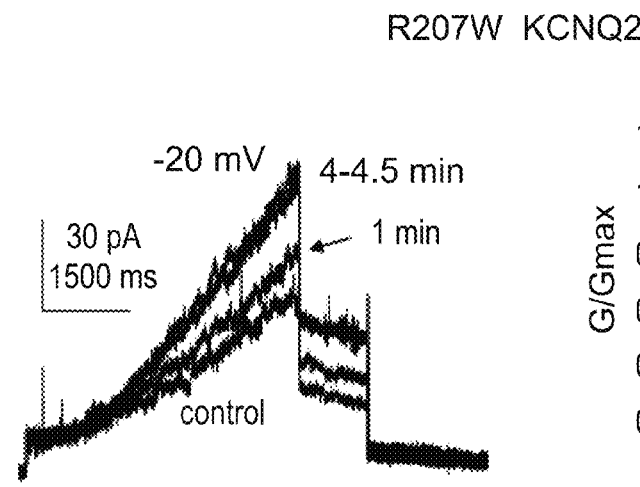
Figure 10D:
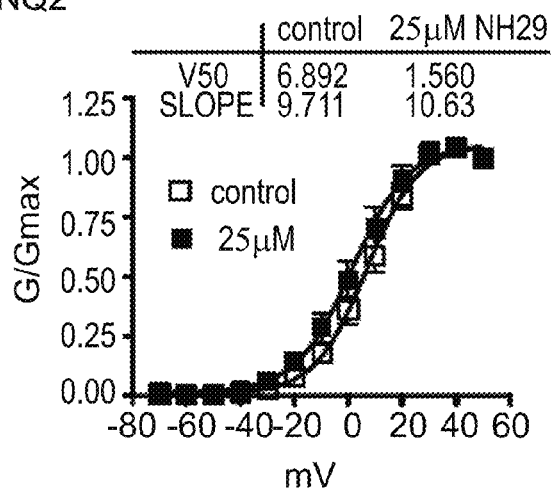

FIG. 1 presents a schematic illustration of the pharmacophoric features of an M-channel binding site, which was deduced from SAR studies of diphenylamine derivatives discussed hereinbelow, showing the chemical features of a diphenylamine-based compound which are relevant to M-channel modulation;

FIGS. 2A-D present the results obtained for compound NH17, an exemplary compound according to embodiments of the present invention, in inhibition assays against the voltage-dependent potassium channel Kv7.2/3, showing that NH17 inhibits currents and enhances firing of peripheral DRG neurons, as reflected in: representative traces recorded from the same CHO cell before (FIG. 2A, left panel) and after (FIG. 2A, right panel) external application 25 µM of NH17, wherein the membrane potential was stepped from −90 mV holding potential to +50 mV for 1.5 second pulse duration in 10 mV increments, followed by a repolarizing step to −60 mV; current density-voltage relations (n=6) in the absence (marked by empty squares in FIG. 2B) and presence (marked by solid squares FIG. 2B) of 25 µM of NH17; representative rat DRG spiking discharge, evoked by a squared depolarizing current pulse (10 pA for 400 msec) before (control), and during exposure to 1 µM of NH17 for 1, 2 and 3 minutes (FIG. 2C); and representative trace of spontaneously spiking DRG neuron previously exposed for 5 minutes to 1 µM of NH17 (FIG. 2D);

FIGS. 3A-F present the results obtained for compound NH25, an exemplary compound according to embodiments of the present invention, in inhibition assays against the voltage-dependent potassium channel Kv7.2/3 expressed in CHO cells, showing the M-channel opener properties of compound NH25, as reflected in: representative traces recorded from the same cell before (FIG. 3A, left panel) and after (FIG. 3A, right panel) external application 50 µM of NH25 wherein the membrane potential was stepped from −90 mV holding potential to +10 mV for 1.5 seconds pulse duration in 10 mV increments, followed by a repolarizing step to −60 mV; cells were stepped from −90 mV to −50 mV every 30 seconds for 1.5 seconds pulse duration, wherein current traces were recorded from the same cell in the absence (control) and presence of 10 µM of NH25 (FIG. 3B) and 50 µM of NH25 (FIG. 3C); the percentage of the current recorded at −50 mV is shown in the presence of 10 µM of NH25 and 50 µM of NH25 and in the absence thereof, the latter being the control of 100% (FIG. 3D, n=10; * p<0.01); the normalized conductance (G/Gmax) plotted as a function of the test voltages measured in treated cells, for control (marked by open squares in FIG. 3E), 10 µM of NH25 (marked by solid squares in FIG. 3E) and 50 µM of NH25 (marked by diamonds in FIG. 3E), wherein the activation curves were fitted using one Boltzmann function (n=5); and the extent of left-shift ($\Delta V_{50}$), plotted as a function of NH25 concentration (n=5) and fitted by a sigmoidal function yielding an $EC_{50}$ value of 22±1 µM (FIG. 3F);

FIGS. 4A-D present the results obtained for compound NH25, an exemplary compound according to embodiments of the present invention, showing the effect of NH25 on activation and deactivation kinetics of Kv7.2/3 potassium channels, as reflected in: the activation kinetics which were evaluated at −20 mV by determining $t_{1/2}$, the time value at which half of the current amplitude developed, in the absence or presence of 25 µM of NH25 (FIG. 4A, n=4; * p<0.02); representative normalized trace of current activation in the absence and presence of 25 µM of NH25 (FIG. 4B); representative normalized trace of current deactivation at −60 mV in the absence and presence of 25 µM of NH25 (FIG. 4C); and at −60 mV, deactivation kinetics were fitted by one exponential function and the time constant was measured in the absence and presence of 25 µM of NH25 (FIG. 4D, n=4; * p<0.02);

FIGS. 5A-E present the results obtained for compound NH25, an exemplary compound according to embodiments of the present invention, showing that NH25 inhibits firing of hippocampal and peripheral DRG neurons, as reflected in: representative rat hippocampal spiking discharge, evoked by a squared depolarizing current pulse (100 pA for 400 msec) before (denoted "control" in FIG. 5A), during exposure to 25 μM NH25 and after washout (denoted "wash" in FIG. 5A); resting membrane potential of DRG neurons before (denoted "control" in FIG. 5B) and following exposure to 25 μM NH25 (n=13; * p<0.01); representative solitary spike evoked in DRG neurons by 2 ms squared depolarizing current pulses (100-1100 pA in 100 pA increments) in the absence (denoted "control" in FIG. 5C) or presence of 25 μM NH25; a number of spikes evoked by injecting squared depolarizing current pulses (75-200 pA for 400 ms) in hippocampal and DRG neurons in the absence and presence of 25 μM NH25 (FIG. 5D, n=8; * p<0.01); and rheobase current necessary to inject (2 ms) into DRG neurons to evoke a solitary spike in the absence and presence of 25 μM NH25 (FIG. 5E, n=12; * p<0.01);

FIGS. 6A-G present the results obtained for compound NH25, an exemplary compound according to embodiments of the present invention, showing the effects of NH25 on spontaneous glutamate and GABA release and on maximal electroshock seizure model in mice, as reflected in: representative traces of spontaneous IPSCs recorded at a holding potential of −70 mV, before (denoted "control" in FIG. 6A), during exposure to 25 μM NH25 and after washout (denoted "wash" in FIG. 6A); representative experiment showing sIP-SCs frequency as a function of time, before, during exposure to 25 μM NH25 and after washout (FIG. 6B); effect of 25 μM NH25 on normalized charge transfer, amplitude and frequency of sIPSCs (FIG. 6C, n=7; * p<0.01), representative traces of spontaneous EPSCs recorded at a holding potential of −70 mV, before (denoted "wash" in FIG. 6D), during exposure to 25 μM NH25 and after washout (denoted "wash" in FIG. 6D); the effect of 25 μM NH25 on normalized burst duration, on frequency and charge transfer within bursts and on total (FIG. 6E) and on the charge transfer of sEPSCs (FIG. 6F, n=6; * p<0.01); and MES generalized epilepsy model in mice (0.2 sec, 50 mA) showing that NH25 protects from epileptic seizures induced by the with $ED_{50}$ of 12 mg/kg (FIG. 6G);

FIGS. 7A-G present the results obtained for compound NH29, an exemplary compound according to embodiments of the present invention, showing that NH29 enhances Kv7.2/3 currents and inhibits firing of peripheral DRG neurons, as reflected in: representative traces recorded from the same CHO cell before (left panel in FIG. 7A) and after (right panel in FIG. 7A) external application 100 μM NH29, wherein the membrane potential was stepped from −90 mV (holding potential) to +40 mV for 1.5 s pulse duration in 10 mV increments, followed by a repolarizing step to −60 mV; the normalized conductance (G/Gmax) curve which was plotted as a function of the test voltages, for control (marked by open squares in FIG. 7B), 25 μM (marked by solid squares in FIG. 7B) and 100 μM (marked by empty circles in FIG. 7B) NH29-treated cells, wherein the activation curves were fitted using one Boltzmann function (n=5); the potency of NH29 was determined by the extent of left-shift ($\Delta V_{50}$), plotted as a function of NH29 concentration and fitted by a sigmoidal function yielding an $EC_{50}$ value of 14±2 μM (FIG. 7C, n=5); representative rat DRG spiking discharge, evoked by a squared depolarizing current pulse (100 pA for 400 msec) before (denoted "control" in FIG. 7D), during exposure to 25 μM NH29 and after washout (denoted "wash" in FIG. 7D); rheobase current necessary to inject (2 ms) into DRG neurons to evoke a solitary spike in the absence and presence of 25 μM NH29 (FIG. 7E, n=8; * p<0.01); the number of spikes evoked by injecting squared depolarizing current pulses (75-200 pA for 400 ms) in DRG neurons in the absence and presence of 25 μM NH29 (FIG. 7F, n=12; * p<0.01); and the resting membrane potential of DRG neurons before (denoted "control" in FIG. 7G) and following exposure to 25 μM NH29 (FIG. 7G, n=7; * p<0.01);

FIG. 8 presents a bar-graph comparing the potentiating effect of 25 μM of Compound NH29 on various KCNQ subunits and mutants, wherein the opener effect is expressed as percent of the control current in the absence of the opener;

FIG. 9 presents a computer generated structural model of two adjacent voltage sensing domains (VSD) in the KCNQ2 channel (S-numbered helices colored in gold and purple) which interact therebetween during channel activation, and showing residue R207 in the S4 helix (colored in salmon) which, when mutated, renders the channel much less sensitive to the opener NH29, and exemplary compound according to the present embodiments, that may dock in the groove formed by the interface between S1, S2 and S4 helices within a VSD;

FIGS. 10A-D present the potentiating effect of NH29, an exemplary channel opener compound according to embodiments of the present invention, on wild type KCNQ2 (FIGS. 10A and 10B) and R207W mutant (FIGS. 10C and 10D) channels, as expressed in activation curve measurements, showing that NH29 left-shifts the activation curve ($\Delta V_{50}$) by −15.5 mV and −5.5 mV in the case of the wild-type and the mutant, respectively, and showing that NH29 enhances the current of wild-type and the mutant by about 3.4-fold (at −40 mV) and 1.5-fold (at −20 mV), respectively.

Figure 11A:
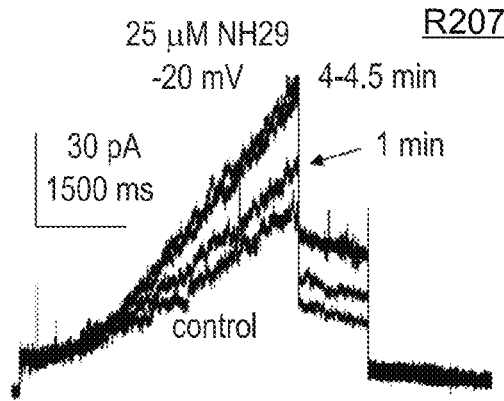
Figure 11B:
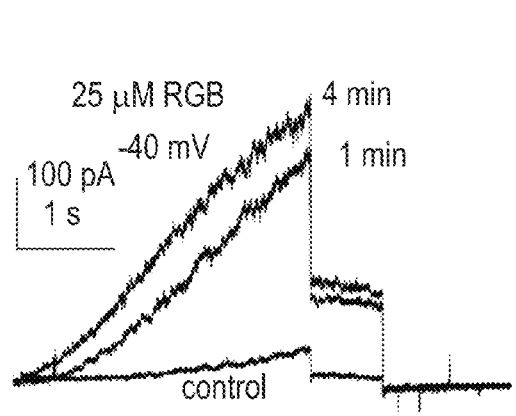
Figure 11C:
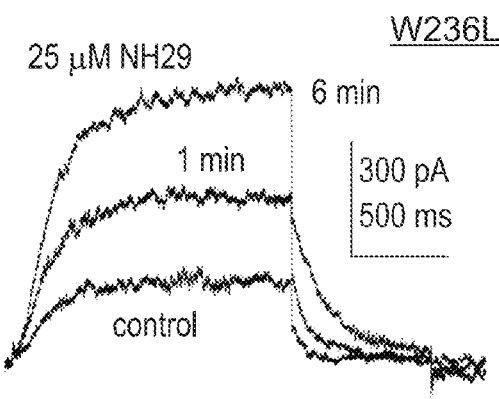
Figure 11D:
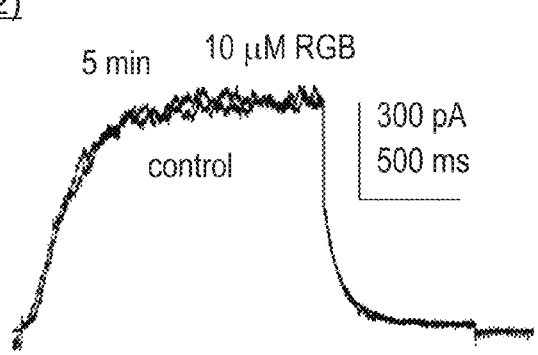
Figure 11E:
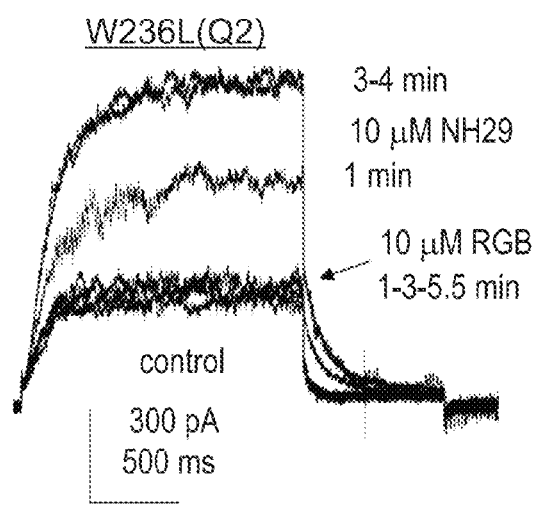
Figure 11F:
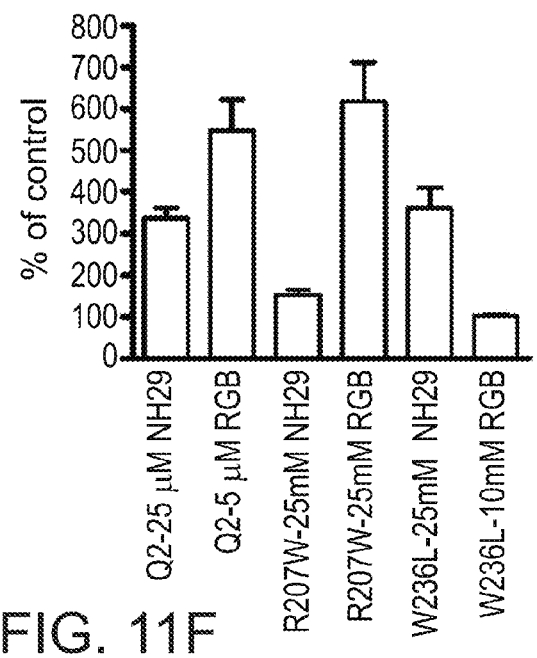

FIGS. 11A-F present the potentiating effect of NH29, an exemplary channel opener compound according to embodiments of the present invention, and Retigabine, on KCNQ2 mutants R207W and W236L mutant. Shown are representative traces recorded from CHO cell transfected with the KCNQ2 mutant R207W 0, 1 and 4-4.5 minutes after external application of 25 μM of NH29 and wherein the membrane potential was stepped from −90 mV holding potential to −20 mV for 1.5 seconds pulse duration (FIG. 11A), or 0, 1 and 4 minutes after external application of 25 μM of Retigabine wherein the membrane potential was stepped from −90 mV holding potential to −40 mV for 1.5 seconds pulse duration (FIG. 11B). FIGS. 11C and 11D show representative traces recorded from CHO cells transfected with the KCNQ2 mutant W236L 0, 1 and 6 minutes after external application of 25 μM of NH29 (FIG. 11C) or 0 and 5 minutes after external application of 10 μM of Retigabine (FIG. 11D) and wherein the membrane potential was stepped from −90 mV holding potential to −40 mV for 1.5 seconds pulse duration. FIG. 11E presents superimposed traces, showing the effects of Retigabine (RTG) and NH29 on the channel activity of KCNQ2 mutant W236L as measured at −40 mV; and FIG. 11F presents a bar diagram comparing the potentiating effect of NH29 and Retigabine on native KCNQ2 and KCNQ2 mutants, wherein the opener effect is expressed as percent of the control current in the absence of the opener. The results show that while the W236L mutant abolishes only the Retigabine-dependent and not the NH29-dependent potentiation of KCNQ2, the R207W mutant abolishes the NH29-dependent but not the retigabine-dependent potentiation of KCNQ2 currents.

FIGS. 12A-F present the potentiating effect of NH29, an exemplary channel opener compound according to embodiments of the present invention, on selected KCNQ2 mutants. Shown are bar diagrams comparing the potentiating effect of NH29 on native KCNQ2 and KCNQ2 mutants, wherein the mutated amino acids are located at the S1-S2 helix region (FIG. 12A) or S4 helix region (FIG. 12D) and wherein the opener effect is expressed as percent of the control current in the absence of the opener. For comparison, marked as a green line, is the observed current increase of native KCNQ2 by NH29. FIGS. 12B 12C, 12E and 12F present representative traces recorded from CHO cell transfected with the KCNQ2 mutant S122A, S121A, L206C and R201A respectively, before and after external application of 25 μM of NH29 and wherein the membrane potential was stepped from −90 mV holding potential to −40 mV for 1.5 seconds pulse duration. The results show that most of the mutation which abolish the NH29 dependent potentiation of KCNQ2, are located in the S4 helix.

Figure 13A:
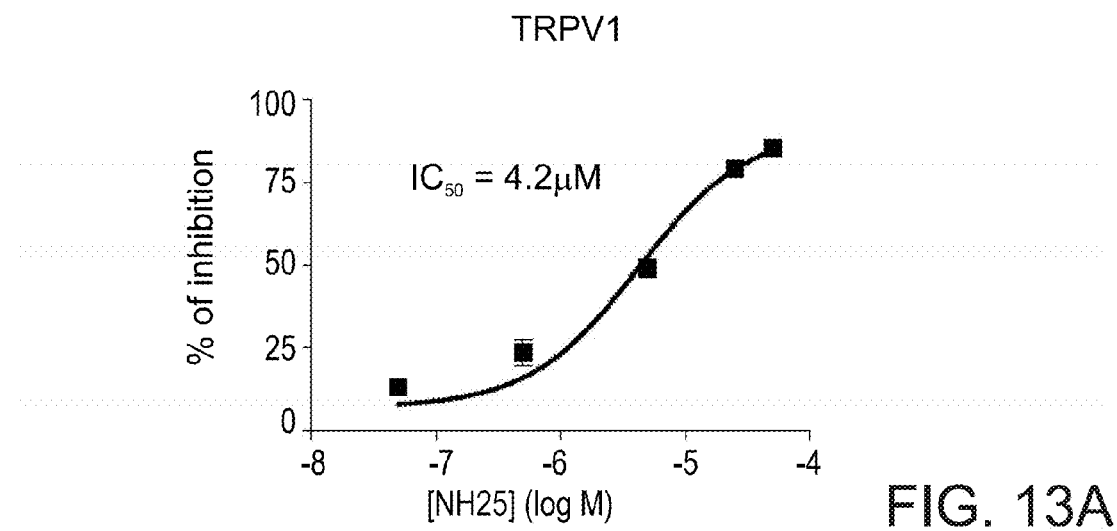
Figure 13B:
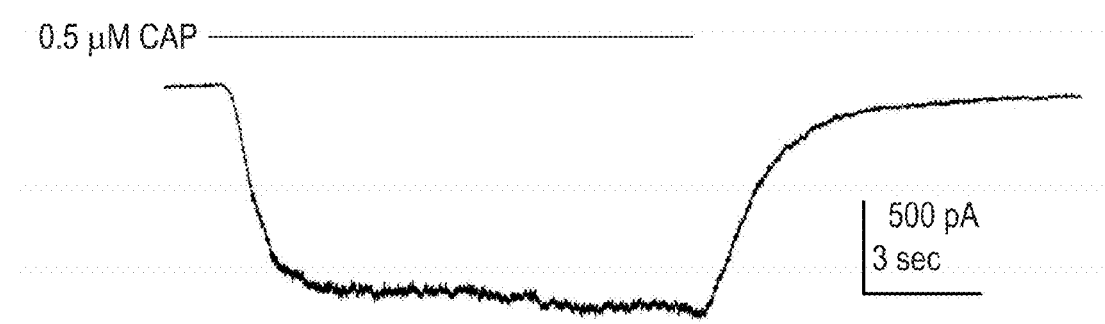
Figure 13C:
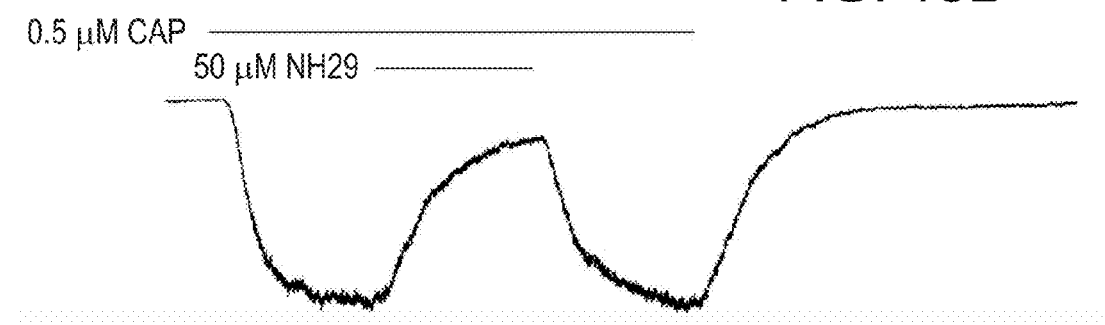

FIGS. 13A-C present the inhibitory effect of NH29, an exemplary compound according to some embodiments of the present invention, on TRPV1 channel. Shown in FIG. 13A is a plot diagram of the percent of TRPV1 channel current inhibition in CHO cells as a function of the concentration of externally applied NH29 wherein the TRPV1 channels were activated with 0.5 μM capsaicin (CAP). Also shown are representative traces recorded from CHO cells transfected with TRPV1 and activated by 0.5 μM capsaicin (FIG. 13B) as compared to a similar cell wherein the external application of 50 μM NH29 inhibited, in a reversible manner, the TRPV1 current almost completely (FIG. 13C).

Figure 14:
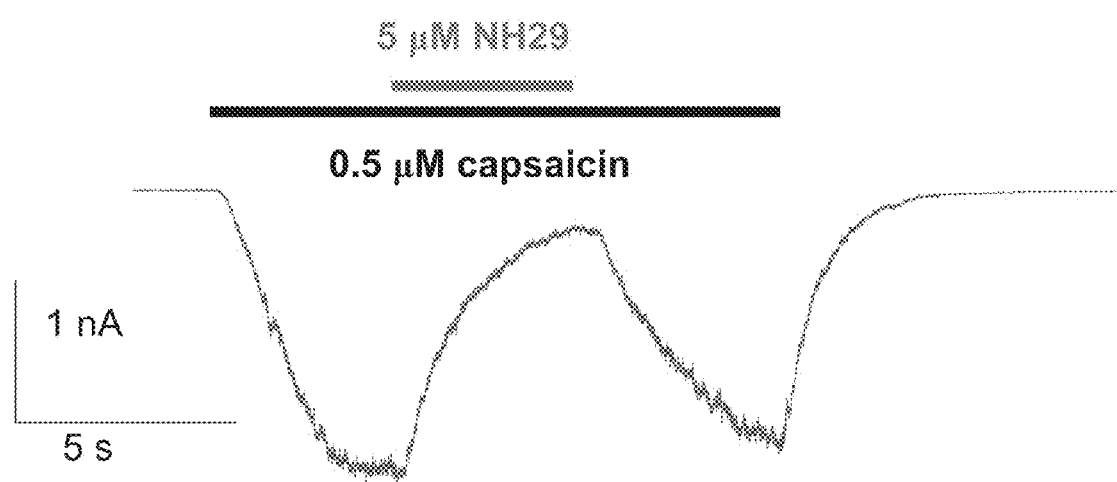

FIG. 14 presents the inhibitory effect of NH29, an exemplary compound according to some embodiments of the present invention, on TRPV1 channels in Dorsal Root Ganglions (DRG). Shown is a representative trace recorded from a DRG neuron upon activation of TRPV1 channels by 0.5 μM capsaicin and external application of 5 μM NH29, which inhibited, in a reversible manner, the TRPV1 current almost completely.

Figure 15A:
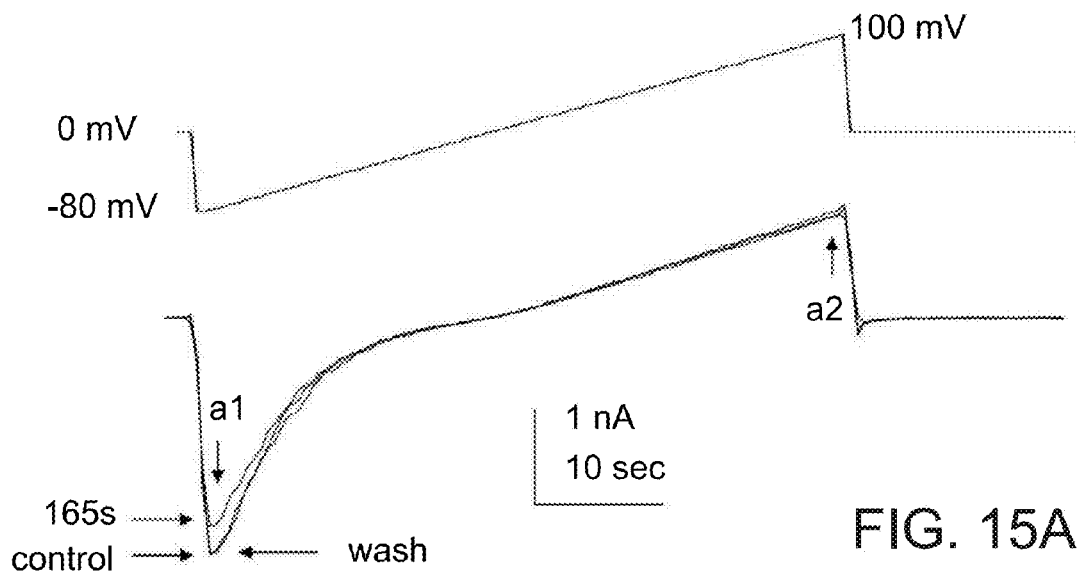
Figure 15B:
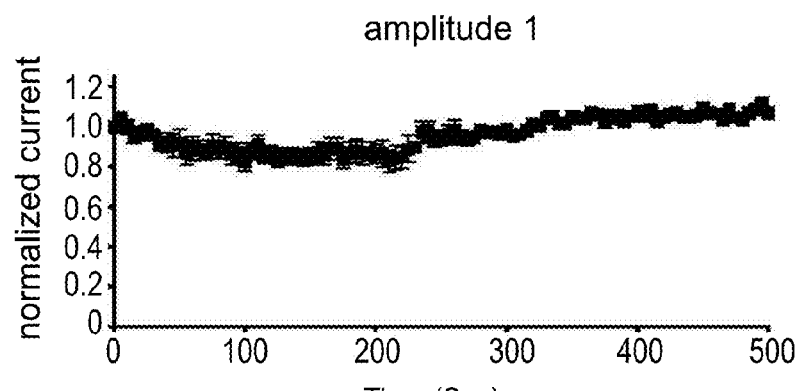
Figure 15C:
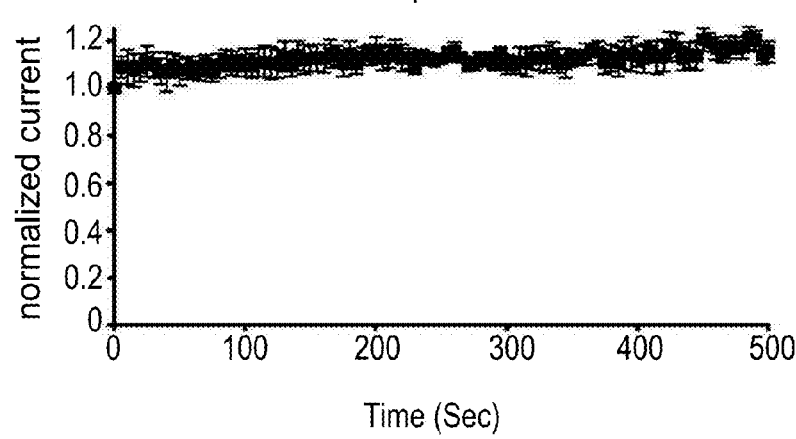

FIGS. 15A-C present the lack of effect of NH29, an exemplary compound according to some embodiments of the present invention, on TRPV6 channel. FIG. 15A presents superimposed representative traces recorded from a CHO cell transfected with TRPV6 before (marked control) during (marked 165s) and after (marked wash) external application of 25 μM NH29, and wherein the membrane potential was stepped from −80 mV to 100 mV for 40 seconds pulse duration (protocol shown in upper panel). The current amplitude was measured at peak current points (marked a 1 at −80 mV and a2 at +100 mV) and plotted as a function of recording time (FIGS. 15B and 15C respectively). The results show that the TRPV6 current is similar before, during and after application of NH29 thus implying lack of modulation of this channel by NH29.

DESCRIPTION OF THE PREFERRED EMBODIMENTS

The present invention is of compounds which can be used to modulate the activity of potassium channels and, more particularly, but not exclusively, to compounds which are based structurally on carboxylic derivatives of diphenylamine, such as 2-(phenylamino)benzoic acid and 2-(2-(phenylamino)phenyl)acetic acid, containing one or more electron-withdrawing substituents on one or both the phenyl rings of the diphenylamine moiety, and to uses thereof as voltage-dependent potassium channels openers. The present invention is further of other compounds which are based structurally on carboxylic derivatives of diphenylamine, and of uses thereof as voltage-dependent potassium channels blockers. The present invention is also of uses of these and other derivatives of diphenylamine in the treatment of medical conditions which are associated with voltage-gated potassium-channel opening or blocking, as well as medical conditions associated with the blocking of the Transient receptor potential vanilloid 1 (TRPV1 channel).

The principles and uses of the present invention may be better understood with reference to the Examples and accompanying descriptions. Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While searching for the binding determinants of potassium channel modulators, SAR studies were conducted, using a number of N-phenylanthranilic acid derivatives having a wide range of chemical and structural variants. N-phenylanthranilic acid is a diphenylamine compound substituted by a carboxylic acid (see illustration below). The phrases N-phenylanthranilic acid derivatives and diphenylamine derivatives are therefore used herein interchangeably. To this end, N-phenylanthranilic acid derivatives having one or more electron-withdrawing substituents on one or both of the phenyl rings, were designed and synthesized.

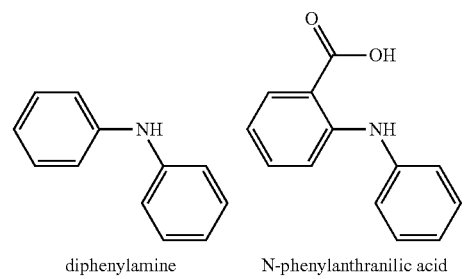

diphenylamine     N-phenylanthranilic acid

As discussed and demonstrated in the Examples section that follows, it was found that electron-withdrawing substituents such as, for example, a nitro group ($NO_2$), increase the channel opener activity of diphenylamine derivatives (see illustration above). It was further found that compounds lacking the secondary amine bridging moiety (between the two phenyl rings) but rather bear another bridging moiety such as, for example, in cases of compounds derived from flurbiprofen, ketoprofen or fenoprofen, do not activate Kv7.2/3 channels. These findings imply that the bridging secondary amine function crucially interacts with an electrophile or is engaged into hydrogen bonding within a hydrophobic pocket site of the M-channel and hence that aromatic ring deactivators such as electron-withdrawing groups strongly affect the channel opening activity of N-phenylanthranilic acid derivatives.

Further, N-phenylanthranilic acid derivatives having various moieties attached to the carboxylic acid groups (represented by the Y group in Formula I hereinbelow) have been designed and synthesized. It was found that the chemical nature of a moiety that is attached to the carboxylic acid group of N-phenylanthranilic acid affects the activity of the compound in terms of opening/blocking a potassium channel. Thus, while an end hydroxy moiety renders the compound an effective opener, other end groups render the compound an effective blocker.

These and other findings served the present inventors in elucidating the pharmacophoric binding sites in a voltage-dependent potassium M-channel. FIG. 1 presents a schematic illustration of the pharmacophoric features of an M-channel binding site, showing the chemical and structural features of a diphenylamine-based compound which are relevant to M-channel modulation. As can be seen in FIG. 1, there are two major "binding pockets" with which the compound interacts, the hydrophobic pocket and the electrophile pocket. Without being bound to any particular theory, it was hypothesized by the present inventors that an electrophile in the hydrophobic pocket interacts with the bridging secondary amine of the compound, and thus electron-withdrawing group(s) on one or both phenyl rings of the compound can accentuate its reactivity and affect its binding. On another side of the compound, a terminal hydroxyl functionality which has two reactive covalent bonds, namely a C—O bond and an O—H bond, which are polarized so that the oxygen acts as an electron rich atom, may react with an electrophile functionality in the protein, while the hydrogen may be involved in hydrogen bonding therewith. It has been shown that when this terminal hydroxyl function is removed, none of the corresponding compounds exhibit M-channel opening activity.

Hence, according to one aspect of the present invention, there is provided a compound having the general Formula I:

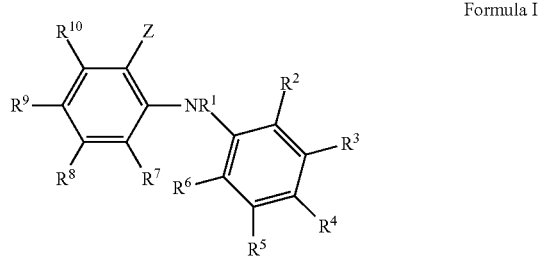

Formula I wherein:

Z is an A-G(=K)—X—Y group;

A is alkyl or absent;

G is selected from the group consisting of C, S and PRa;

K is selected from the group consisting of O and S;

X is selected from the group consisting of O, S and NRb or absent; and

Y is selected from the group consisting of hydrogen, alkyl, hydroxyalkyl, cycloalkyl, aryl and a polyalkylene glycol moiety, $R^1$ is selected from the group consisting of hydrogen, alkyl, cycloalkyl or aryl;

each of $R^2$, $R^3$, $R^4$, $R^5$, $R^6$, $R^7$, $R^8$, $R^9$ and $R^{10}$ is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$, or, alternatively, at least two of $R^2$, $R^3$, $R^4$, $R^5$ and $R^6$, and/or of $R^7$, $R^8$, $R^9$ and $R^{10}$ form a five- or six-membered aromatic, heteroaromatic, alicyclic or heteroalicyclic ring; and each of Ra and Rb, is independently selected from the group consisting of hydrogen, alkyl, cycloalkyl and aryl, provided that at least one of $R^2$, $R^3$, $R^4$, $R^5$, $R^6$, $R^7$, $R^8$, $R^9$ and $R^{10}$ is an electron-withdrawing group.

As used herein, the term "alkyl" describes an aliphatic hydrocarbon including straight chain and branched chain groups. The alkyl group typically has 1 to 20 carbon atoms, and preferably 1-10 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted. When substituted, the substituent can be, for example, an amine, an alkyl, an alkenyl, an alkynyl, a cycloalkyl, an aryl, a heteroaryl, a halo, a hydroxy, a thiohydroxy, an alkoxy, a thioalkoxy and a hydroxyalkyl as these terms are defined hereinbelow. For example, an alkyl substituted with a hydroxyl constitutes a hydroxyalkyl, and an alkyl substituted with one or more halogen atoms constitutes a haloalkyl. The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "alicyclic", used interchangeably with the term "cycloalkyl", describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, an amine, an alkyl, an alkenyl, an alkynyl, a cycloalkyl, an aryl, a heteroaryl, a halo, a hydroxy, a thiohydroxy, an alkoxy, a thioalkoxy and a hydroxyalkyl as these terms are defined herein.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, an amine, an alkyl, an alkenyl, an alkynyl, a cycloalkyl, an aryl, a heteroaryl, a halo, a hydroxy, a thiohydroxy, an alkoxy, a thioalkoxy and a hydroxyalkyl as these terms are defined herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents such as, for example, an amine, an alkyl, an alkenyl, an alkynyl, a cycloalkyl, an aryl, a heteroaryl, a halo, a hydroxy, a thiohydroxy, an alkoxy, a thioalkoxy and a hydroxyalkyl as these terms are defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents such as, for example, an amine, an alkyl, an alkenyl, an alkynyl, a cycloalkyl, an aryl, a heteroaryl, a halo, a hydroxy, a thiohydroxy, an alkoxy, a thioalkoxy and a hydroxyalkyl as these terms are defined herein.

As used herein, the term "halo" (also referred to herein as "halide"), describes an atom of fluorine, chlorine, bromine or iodine, also referred to herein as fluoro, chloro, bromo and iodo, or fluoride, chloride, bromide and iodide.

The term "hydroxy", as used herein, refers to an —OH group.

The term "thiohydroxy", as used herein, refers to an —SH group.

As used herein, the term "amine" or "amino" describes a —NRR' group where each of R and R' is independently hydrogen, alkyl, cycloalkyl, heteroalicyclic, aryl or heteroaryl, as these terms are defined herein.

The term "alkoxy", as used herein, refers to a —O—R group, wherein R is an alkyl.

The term "thioalkoxy", as used herein, refers to a —S—R group, wherein R is as defined hereinabove.

The term "aryloxy", as used herein, refers to a —O—R group, wherein R is aryl.

The term "sulfinyl" or "sulfoxide" refer to a —S(=O)—R' group, where R' is as defined herein.

The term "sulfonyl" or "sulfone" refer to a —S(=O)$_2$—R' group, where R' is as defined herein.

The term "sulfonate" refers to a —S(=O)2-O—R' group, where R' is as defined herein.

The term "cyano" refers to a —C≡N group.

The term "nitro" refers to a —NO$_2$ group

The phrase "carboxy moiety" is used herein to collectively describe chemical moieties which are derivatives or analogues of a carboxylate, as defined herein, and encompasses, for example, amides, thiocarboxylates, dithiocarboxylates, thioamides, imides or N-substituted imides, thioimides and amidines, as these terms are defined herein.

As used herein, the term "derivative" describes the result of chemically altering, modifying or changing a molecule or a portion thereof, such that it maintains its original functionality in at least one respect.

In Formula I, when G is C (carbon) and K and X are both O (oxygen), the A-G(=K)—X—Y group is a carboxylate, as defined herein.

The term "carboxylate", as used herein, refers to a —C(=O)—O—R', where R' is as defined herein.

When G is C (carbon), K is O and X is NRb, the A-G (=K)—X—Y group is an amide, as defined herein.

The term "amide" describes a —C(=O)—NR'R", where R' is as defined herein and R" is as defined for R'.

When G is C, K is O and X is S (sulfur), or when K is S and X is O, the A-G(=K)—X—Y group is a thiocarboxylate, as defined herein.

The term "thiocarboxylate", as used herein, refers to a —C(=O)—S—R', where R' is as defined herein. When R' is an alkyl, the thiocarboxylate is referred to as a thiocarboxylate-S-alkyl ester, and when the group is —C(=S)—O—R', the thiocarboxylate is referred to as a thiocarboxylate-O-alkyl ester.

When G is C and both K and X are S, the A-G(=K)—X—Y group is a dithiocarboxylate, as defined herein.

The term "dithiocarboxylate", as used herein, refers to a —C(=S)—S—R', where R' is as defined herein.

As used herein the term "imide" refers to a —C(=NR')—O—R" group, where R' and R" are as defined herein.

As used herein the term "amidine" refers to a —C(=NR')—NR"R'" group, where R' and R" are as defined herein, and R'" is as defined for R'.

The term "thioamide" describes a —C(=S)—NR'R" group, where R' is as defined herein and R" is as defined for R'.

The term "thioimide" describes a —C(=NR')—SR" group, where R' and R" are as defined herein.

When G is PRa, the A-G(=K)—X—Y group can be a phosphine (a —PRaR' group), a phosphinite (a —PRa-R' group), or a phosphinate (a —PRa(=O)—R' group).

As demonstrated in the Examples section that follows, compounds according to the present embodiments, in which the A-G(=K)—X—Y group is a carboxylate, namely, the Y is attached to the N-phenylanthranilic acid moiety via an ester bond, were found to exhibit an anti-COX activity. In some embodiments, such an anti-COX activity is a tissue-selective anti-COX activity, which allows using these compounds without affecting COX activity in the stomach or kidney, and thus avoiding the adverse side affects associated with inhibiting COX activity in these tissues.

Compounds according to the present embodiments, in which the A-G(=K)—X—Y group is an amide, namely, the Y is attached to the N-phenylanthranilic acid moiety via an amide bond, were found to be devoid of an anti-COX activity.

Polyalkylene glycol is a general name which refers to a family of polyether polymers that share the following general formula: HO—[(CH$_2$)m-O-]n-CH$_2$OH, wherein m represents the number of methylene groups present in each monomer unit, and n represents the number of repeating monomer units, and therefore represents the size of the polymer. For example, when m=2, the polymer is referred to a polyethylene glycol, and when m=3, the polymer is referred to a polypropylene glycol.

As used herein, the term "moiety" describes a part, and typically a major part, of a chemical entity, such as a molecule or a group, which has underwent a chemical reaction and is now covalently linked to another molecular entity.

A phrase "polyalkylene glycol moiety" is a general name of a substituent which is a polyalkylene glycol attached to another molecule, and which is typically terminated by a hydroxy group.

According to some embodiments of the present invention, the polyalkylene glycol moiety has a general Formula II:

$$[(CH_2)m\text{-}O]n\text{-}R^{17} \qquad \text{Formula II}$$

wherein each of m and n is independently an integer of 1-10; and $R^{17}$ is a CH$_2$OH group, hydrogen, alkyl, cycloalkyl or aryl, as these are defined hereinabove.

In some embodiments of the invention, in each of the compounds described in this and in other aspects of the invention, the polyalkylene glycol moiety having Formula II above, does not include an anti-oxidant moiety or a —ONO$_2$ group.

Exemplary polyalkylene glycol moieties, as defined herein, include ethylene glycol moieties such as ethanol-2-yl, 2-ethoxyethanol, 2-(2-(2-ethoxy)ethoxy)ethanol and 2-(2-(2-ethoxyethoxy)ethoxy)ethanol.

The phrase "electron-withdrawing group", as used herein, refers to a chemical group in a molecule, which can draw electrons away from an adjacent part of the molecule. The distance over which the electron-withdrawing group can exert its effect, namely the number of bonds over which the electron-withdrawing effect spans, is extended by conjugated pi-electron systems such as aromatic systems. Non-limiting examples of electron-withdrawing groups include, going from the more electron-withdrawing to the less electron-withdrawing, nitro, ammonium (positively charged amino cations), sulfonate, cyano, trihaloalkyl (such as trifluoromethyl), acyl-halide (a —C(=O)X group wherein X is halide), various carboxy moieties (e.g., carboxylate, amide), carbonyl or aldehyde (a —C(=O)—R' group wherein R' is as defined hereinabove) and halo.

According to some embodiments of the present invention, the electron-withdrawing group is nitro.

The number of electron-withdrawing groups which are present on an aromatic system, such as a phenyl ring, affects the extent of the electron-withdrawing effect. Hence, according to some embodiments, at least two of $R^2$, $R^3$, $R^4$, $R^5$, $R^6$, $R^7$, $R^8$, $R^9$ and $R^{10}$ in Formula I are electron-withdrawing groups. Thus, in some embodiments, 2, 3 or even 4 of $R^2$, $R^3$, $R^4$, $R^5$, $R^6$, $R^7$, $R^8$, $R^9$ and $R^{10}$ in Formula I are electron-withdrawing groups.

As discussed hereinabove, an electron-withdrawing group exerts its electron-withdrawing effect across conjugated pi-electron systems such as aromatic systems. Hence, according to embodiments of the present invention, at least one of the substituents on one or both of the phenyl rings of the diphenylamine moiety of Formula I is an electron-withdrawing group, namely at least one of $R^2$, $R^3$, $R^4$, $R^5$, $R^6$, $R^7$, $R^8$, $R^9$ and $R^{10}$ is an electron-withdrawing group. According to particular embodiments, at least one of $R^7$, $R^8$, $R^9$ and $R^{10}$ is the electron-withdrawing group.

The relative position of an electron-withdrawing group on an aromatic system such as a phenyl ring, namely the meta-, ortho- or para-position, may also affect the extent of the electron-withdrawing effect. Thus, the relative position of the electron-withdrawing group(s) with respect to other substituents on the phenyl rings of the diphenylamine moiety of Formula I may be significant to the effect exhibited thereby.

Hence, according to some particular embodiments, $R^9$, which is at the para-position with respect to the bridging amine in Formula I is an electron-withdrawing group. According to other embodiments, at least one of $R^9$ and $R^7$, the latter is at the ortho-position with respect to the bridging amine, is an electron withdrawing group. According to still other embodiments, at least one $R^9$, $R^7$ and $R^4$, the latter of which is at the para-position with respect to the bridging amine of the compound, is an electron withdrawing group.

As demonstrated in the Examples section which follows, compounds prepared according to embodiments of the present invention and having at least one of the electron-withdrawing group(s) at positions $R^9$, were found to be highly potent. Such exemplary compounds include the compounds referred to hereinbelow as NH24, NH25 and NH30.

According to other embodiments of the present invention, the compound exhibits at least one of the electron-withdrawing group(s) at positions $R^7$, $R^8$, $R^9$ or $R^{10}$, and at least one other electron-withdrawing group at positions $R^2$, $R^3$, $R^4$, $R^5$ or $R^6$, such as in the case of the exemplary compound referred to hereinbelow as NH28, which exhibits a nitro group at each of $R^4$ and $R^9$; and as in the case of the exemplary compounds NH29 and NH31 which both exhibit an electron-withdrawing group at each of $R^9$, $R^7$ and $R^4$.

According to another aspect of the present invention, there is provided a process of preparing the compounds described hereinabove.

Specifically, the process of preparing the compounds presented hereinabove and represented by Formula I is effected by:

reacting a compound having a general Formula I*:

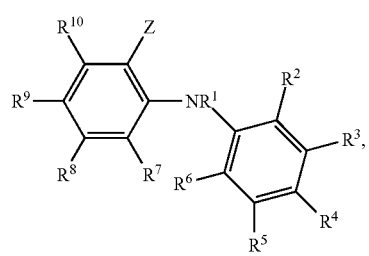

Formula I* wherein:
Z is an A-G(=K)—X—Y group;
A is alkyl or absent;
G is selected from the group consisting of C, S and PRa;
K is selected from the group consisting of O and S;
X is selected from the group consisting of NRb, S or absent; and
Y is selected from the group consisting of hydrogen, alkyl, hydroxyalkyl, cycloalkyl, aryl and a polyalkylene glycol moiety,
$R^1$ is selected from the group consisting of hydrogen, alkyl, cycloalkyl or aryl;
each of $R^2$, $R^3$, $R^4$, $R^5$, $R^6$, $R^7$, $R^8$, $R^9$ and $R^{10}$, is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —NR$^{15}$R$^{16}$, or, alternatively, at least two of $R^2$, $R^3$, $R^4$, $R^5$ and/or $R^6$, of $R^7$, $R^8$, $R^9$ and $R^{10}$ form a five-membered or six-membered aromatic, heteroaromatic, alicyclic or heteroalicyclic ring; and
each of Ra and Rb is independently selected from the group consisting of hydrogen, alkyl, cycloalkyl and aryl;
with an agent capable of substituting one or more of $R^2$, $R^3$, $R^4$, $R^5$, $R^6$, $R^7$, $R^8$, $R^9$ and $R^{10}$ by an electron-withdrawing group, to thereby obtain the compound having the general Formula I.

The phrase "agent capable of substituting", as used in the context of the present embodiments, refers to a chemical reagent which can effectively replace hydrogen or another chemical group on one or more positions in the phenyl ring(s) of the compounds represented by Formula I*, namely replacing one or more of the $R^2$, $R^3$, $R^4$, $R^5$, $R^6$, $R^7$, $R^8$, $R^9$ and $R^{10}$ substituents. The phrase "agent capable of substituting a substituent by an electron-withdrawing group" therefore refers to such reagents which can place an electron-withdrawing group in place of one or more substituent(s).

According to some embodiments of the present invention, the electron-withdrawing group in the compounds presented herein is nitro and the agent capable of substituting one or more positions on one or more of the two phenyl rings of the diphenylamine moiety by an electron-withdrawing group is a nitrating agent.

In the context of the present embodiments, the phrase "nitrating agent" refers to an agent which is capable of substituting a hydrogen atom or another substitutable group with another group by a group having one or more nitro groups.

A non-limiting example of a nitrating agent is nitrated silica gel ($HNO_3/SiO_2$). Other exemplary nitrating agents include organic nitrates such as nitroglycerin, isosorbide dinitrate, isosorbide 5-mononitrate, isobutyl nitrate and isopentyl nitrate, nitronium salts and other inorganic nitrates such as nitronium tetrafluoroborate and dinitrogen tetroxide, alkali metal nitrates such as sodium and potassium nitrate, nitric acid at various concentrations, such as fuming nitric acid and concentrated and other conventional nitrating mixtures such as nitric acid/sulfuric acid, potassium nitrate/sulfuric acid, and nitric acid/sulfuric acid/acetic anhydride.

The present embodiments further encompass any enantiomers, prodrugs, solvates, hydrates, metabolites and/or pharmaceutically acceptable salts of the compounds described herein.

Certain compounds according to embodiments of the present invention may possess asymmetric carbon atoms (optical centers) or double bonds; the racemates, diastereomers, geometric isomers and individual isomers are encompassed within the scope of the present invention.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

Additionally, prodrugs can be converted to the compounds according to embodiments of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

As used herein, the term "metabolite" describes a substance that is typically associated with one or more metabolic processes (various sets of chemical reactions that occur in living cells) that occur in vivo upon administration of the compound, namely a substance produced by a metabolic process, required for a metabolic process and/or participating in a metabolic process.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable salts" is meant to encompass salts of the active compounds which are prepared with relatively nontoxic acids or bases, depending on the particular substituents found on the compounds described herein. When compounds according to embodiments of the present invention contain relatively acidic functionalities, base addition salts can be obtained by contacting the neutral (i.e., non-ionized) form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds according to embodiments of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The compounds according to embodiments of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds presented herein, whether radioactive or not, are intended to be encompassed within the scope of the present invention.

According to embodiments of the present invention, the compounds presented herein have an affinity towards certain voltage-dependent potassium channels, such as, for example, KCNQ2 channels and/or KCNQ3 channels and/or KCNQ2/3 channels.

As demonstrated in the Examples section that follows, the compounds presented herein were tested for opening (activating) a voltage-dependent potassium channel and/or of depressing cortical and/or peripheral neuron activity, and were shown to possess these capacities. In these experiments, the compounds presented herein were found to exert two main effects: shifting of the voltage dependence of KCNQ2/3 channel activation to more hyperpolarized potentials and slowing channel deactivation. Without being bound to any theory in particular, these data suggest that the compounds described herein either destabilize a closed channel conformation or stabilize the KCNQ2/3 channel in an open state.

Further, exposure of channels to some of the compounds described herein also leads to a slowing of deactivation that contributes to the stabilization of the KCNQ2/3 channel in the open state. Without being bound to any theory in particular, it is assumed that these compounds modify the channel gating by shifting the voltage dependence of the voltage sensor S4 movement in the hyperpolarizing direction.

From a functional point of view, the leftward shift in the voltage dependence and the slowing of deactivation, caused by the compounds presented herein, lead to substantial M-current activation at normal resting and sub-threshold potentials. In addition, since the M-current (KCNQ2/3) is non-inactivating, its marked activation by these compounds contributes to a significant steady-state potassium conductance at sub-threshold and threshold potentials, acting as brake for neuronal firing. Indeed, it is also demonstrated that these compounds depress the evoked and spontaneous cortical neurons activity.

From a functional point of view, the leftward shift of the activation curve and the slowing of deactivation, effected by the compounds of the present invention, leads to substantial M-current activation at normal resting and sub-threshold potentials. In addition, since the M-current (KCNQ2/3) is non-inactivating, activation by these compounds is expected to contribute to a significant steady-state potassium conductance at sub-threshold and threshold potentials, acting as a brake for neuronal firing.

The above-described activities render these compounds highly suitable for use as therapeutically active agents for the treatment of medical conditions wherein opening of voltage-dependent potassium channels, and/or depressing cortical and/or peripheral neuron activity, is beneficial.

Thus, according to another aspect of the present invention there is provided a method of opening a voltage-dependent potassium channel and/or of depressing cortical and/or peripheral neuron activity, the method being effected by administering to a subject in need thereof a therapeutically effective amount of a compound having the general Formula I, as detailed herein.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Accordingly, there is provided a use of an effective amount of a compound having the general Formula I in the manufacture of a medicament for treating a condition in a subject in which opening a voltage-dependent potassium channel and/or in depressing cortical and/or peripheral neuron activity is beneficial.

As used herein, the terms "opening" or "activating", for example, can be used interchangeably to refer to the partial or full activation of an ion channel, such as a KCNQ channel and other potassium channels, by a compound, which leads to an increase in ion flux either into or out of a cell in which an ion channel is found. Such a compound may also be referred to as an agonist with respect to the potassium channel.

As used herein, the phrase "therapeutically effective amount" describes an amount of the compound being administered (the active ingredient) needed to achieve the desired outcome, and which will generally relieve to some extent one or more of the symptoms of the condition being treated. Determination of a therapeutically effective amount is within the capability of those skilled in the art, especially in light of the detailed disclosure provided herein.

As used herein, the terms "treating" and "treatment" include abrogating, substantially inhibiting, slowing or reversing the progression of a condition, substantially ameliorating clinical or aesthetical symptoms of a condition or substantially preventing the appearance of clinical or aesthetical symptoms of a condition.

As voltage dependent potassium channels are found in all animal species, the compounds of the present invention are pharmaceutically effective when administered to subjects who are members of all animal species, including humans, monkeys, dogs, cats, mice, rats, farm animals, livestock, fish and most importantly humans.

There is much pathology, conditions and disorders that is associated with defective potassium channel functioning. Just as other potassium channel opening compounds, the compounds described herein are for use within the framework of a treatment for pathologies, conditions and disorders associated with defective potassium channel functioning, so as to treat, ameliorate, prevent, inhibit, or limit the effects of the conditions and pathologies in animals including humans.

Exemplary medical conditions that are beneficially treatable by the potassium channel openers described herein include, but are not limited to, central or peripheral nervous system disorders such as ischemic stroke, migraine, ataxia, Parkinson's disease, bipolar disorders, trigeminal neuralgia, spasticity, mood disorders, brain tumors, psychotic disorders, schizophrenia, myokymia, neurogenic pain, neuropathic pain, seizures, epilepsy, hearing and vision loss, anxiety and motor neuron diseases. The compounds described herein can further be beneficially used as neuroprotective agents (e.g., to prevent stroke and the like). The compounds described herein are also useful in treating disease states such as gastroesophogeal reflux disorder and gastrointestinal hypomotility disorders.

Notably, the voltage range through which compounds of the present embodiments activate KCNQ2/3 channels makes theses compounds exceptionally useful for the treatment of epilepsy, including convulsive states, for example that following grand mal, petit mal, psychomotor epilepsy or focal seizure, ischemic stroke and neuropathic pain.

These compounds can also be used as potent candidates for treating a variety of medical conditions wherein depressing the cortical and/or peripheral neuron activity is beneficial, such as, for example, epilepsy, ischemic stroke, migraine, ataxia, myokymia, neurogenic pain, neuropathic pain, Parkinson's disease, bipolar disorder, trigeminal neuralgia, spasticity, mood disorder, psychotic disorder, schizophrenia, brain tumor, hearing and vision loss, anxiety and a motor neuron disease.

Other pathologies and conditions that compounds which can activate (open) potassium channels according to embodiments of this aspect of the present invention are useful in treating are listed in, for example, U.S. Pat. Nos. 6,348,486; 6,117,900; 6,589,986 and 6,593,349 and U.S. patent applications Ser. Nos. 10/022,579; 10/075,703; 10/075,522; 10/114,148; 10/160,582 and 10/312,123, all of which are hereby incorporated by reference as if fully set forth herein.

As further demonstrated in the Examples section that follows, NH29, an exemplary compound according to embodiments of the present invention, was tested for its ability to depress TRPV1 currents and was indeed shown to exhibit such an activity.

Hence, the compounds presented hereinabove, having general Formula I, as well as other derivatives of N-phenylanthranilic acid, as detailed hereinbelow, are further characterized as capable of blocking TRPV1.

The Transient receptor potential vanilloid 1 (TRPV1) belongs to the transient receptor potential family and is a nonselective ligand-gated cation channel that may be activated by a wide variety of exogenous and endogenous stimuli, including heat typically above 43° C., low pH (typically below 6), anandamide, N-arachidonoyl-dopamine, and capsaicin. TRPV1 receptors are found in the central nervous system and the peripheral nervous system and are involved, inter alia, in the transmission and modulation of pain, as well as the integration of diverse painful stimuli.

TRPV1 has also been found to be involved in the regulation of body temperature, anxiety and mediation of long term depression (LTD) in the hippocampus. TRPV1 channels are also located on sensory afferents which innervate the bladder. Inhibition of TRPV1 has been shown to ameliorate urinary incontinence symptoms.

The inhibitory activity of the compounds presented herein (see, general Formula I) for TRPV1, renders these compounds even more suitable for treating medical conditions such as pain and certain CNS disorders, and further renders these compounds suitable for use in the treatment of other TRPV1 related conditions, as detailed hereinbelow.

As further demonstrated in the Examples section that follows, the compounds presented herein were further tested for their modulation of TRPV6, and were found as not affecting this channel.

TRPV6 is another member of the transient receptor potential family of membrane proteins which is responsible for the first step in calcium absorption in the intestine. As demonstrated in the Examples section that follows, the compounds presented herein, having general Formula I, were found to specifically inhibit TRPV1 but not TRPV6. This feature indicates that utilizing these compounds would not be associated with TRPV6-related adverse effects.

The compounds according to these embodiments of the present invention can be utilized in any of the methods described herein, either per se or as a part of a pharmaceutical composition, which further comprises a pharmaceutically acceptable carrier.

Hence, according to yet another aspect of the present invention there is provided a pharmaceutical composition which includes, as an active ingredient, the compound having the general Formula I and a pharmaceutically acceptable carrier.

In some embodiments, the composition is packaged in a packaging material and identified in print, in or on the packaging material, for use in the treatment of a condition in which opening a voltage-dependent potassium channel and/or in depressing cortical and/or peripheral neuron activity is beneficial.

During the SAR studies described herein, the present inventors have surprisingly found that some particular chemical and structural determinants in the diphenylamine derived compounds bestow channel blocking characteristics to the effect of the compounds on potassium channels, namely the compounds possessing these chemical traits act as potassium channel blockers (see, FIG. 1).

It is noted that compounds having a blocking activity with respect to potassium channels where neither disclosed nor discussed in WO2004/035037 or U.S. Patent Application No. 20050250833.

As used herein, the terms "blocking", "closing", "inhibiting" or "deactivating", for example, can be used interchangeably to refer to the partial or full deactivation of an ion channel, such as a KCNQ channel and other potassium channels, by a compound, which leads to a decrease in ion flux either in or out of a cell in which an ion channel is found. Such a compound may also be referred to as an antagonist with respect to the potassium channel.

The blocking activity presented herein can be harnessed for the treatment of a variety of cognitive conditions or disorders, which are known to be associated with enhancement of neuronal activity. Cognitive enhancement at the neural level can be useful in the treatment of, for a non-limiting example, memory deficits and Alzheimer's disease.

Hence, according to another aspect of the present invention, there is provided a method of blocking a voltage-dependent potassium channel, the method being effected by administering to the subject in need thereof a therapeutically effective amount of a compound having a general Formula III:

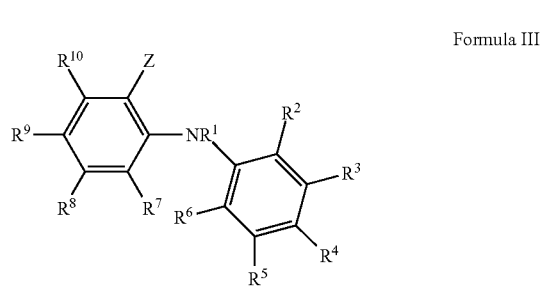

Formula III a pharmaceutically acceptable salt, a prodrug or a metabolite thereof,
wherein:
Z is an A-G(=K)—X—Y group,
A is alkyl or absent;
G is selected from the group consisting of C, S and PRa;
K is selected from the group consisting of O and S;
X is selected from the group consisting of NRb, S or absent; and
Y is selected from the group consisting of alkyl, aryl, cycloalkyl, heteroalicyclic and a positively charged group, with the proviso that Y does not contain a hydroxy group;
$R^1$ is selected from the group consisting of hydrogen, alkyl, cycloalkyl or aryl;
each of $R^2$, $R^3$, $R^4$, $R^5$, $R^6$, $R^7$, $R^8$, $R^9$ and $R^{10}$, is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$ or alternatively, at least two of $R^2$, $R^3$, $R^4$, $R^5$ and/or $R^6$, of $R^7$, $R^8$, $R^9$ and $R^{10}$ form a five- or six-membered aromatic, heteroaromatic, alicyclic or heteroalicyclic ring; and
each of Ra and Rb is independently selected from the group consisting of hydrogen, alkyl, cycloalkyl and aryl.

According to some embodiments, Y is a positively charged group. When stable in physiological pH, this chemical feature adds an advantage to this blocker particularly in cases where the target is the peripheral nervous system as opposed to the central nervous system, such as in treating neuropathic pain, since a charged compound will not penetrate the blood-brain barrier.

The phrase "positively charged group", as used herein, refers to an atom or a group of atoms which forms a part of an organic molecule, and which is characterized by a positive electrostatic charge. Compounds which include one or more positively charged groups are molecular ions oftentimes referred to as molecular cations. A positively charged group of atoms has at least one electron less than the number of protons in these atoms. Positively charged groups include, for a non-limiting example, ammonium and sulfonium groups.

A positively charged group which retains its charge at physiological pH is a group that is not capable of participating in proton-exchange interactions at a pH range which is typical to the physiological environment in the body where the compound is active. Typically, the physiological pH is about 7.4; therefore a positively charged group which retains its charge at physiological pH refers to a positively charged chemical group that stays ionized in a pH range of about 5-8. It is noted that even in the GI, where the pH level is extremely low in terms of physiological pH, the positively charged group according to preferred embodiments remains positively charged, and hence compounds according to the present invention designed for oral administration, are not adversely affected by the GI pH levels.

The positively charged group, according to preferred embodiments of the present invention, is an ammonium group selected from the group consisting of a primary ammonium group (an —$N^+H_3$ group), a secondary ammonium group (an —$N^+H_2R$ group wherein R is as defined hereinabove), a tertiary ammonium group (an —$N^+HRR'$ group wherein R and R' are as defined hereinabove) and a quaternary ammonium group (an —$N^+RR'R''$ group wherein R and R' are as defined hereinabove and R'' is as defined for r and R). Quaternary ammonium groups are known to be positively charged at any pH range, including the physiological pH range.

Sulfonium groups are also known to be positively charged at the physiological pH. The term "sulfonium", as used herein, refers to a —$S+RR'$, wherein R and R' are as defined hereinabove.

According to other embodiments, Y is a heteroalicyclic, and preferably the heteroalicyclic is an epoxide (a cyclic ether with only three ring atoms having a structure which is close to an equilateral triangle), such as, for example, 2,3-epoxypropyl or methyloxirane.

According to embodiments of the present invention, the method of blocking a voltage-dependent potassium channel is useful in the treatment of a cognitive conditions or disorder. Exemplary conditions or disorders include, but are not limited to, Alzheimer's disease, age-related memory loss, a memory deficit, a memory deficit related to brain injury or a post-stroke event and a learning deficiency.

According to another aspect of the present invention, there is provided a pharmaceutical composition that includes, as an active ingredient, a compound having a general Formula III as defined hereinabove. The composition according to embodiments of this aspect of the present invention, is being packaged in a packaging material and identified in print, in or on the packaging material, for use in blocking a voltage-dependent potassium channel.

Accordingly, there is provided a use of a compound having the general Formula III in the preparation of a medicament for treating a condition in which blocking a voltage-dependent potassium channel and/or in enhancing cortical and/or peripheral neuron activity is beneficial.

In the context of any of the methods, uses and pharmaceutical compositions described herein, the voltage-dependent potassium channel includes a KCNQ2 channel and/or a KCNQ3 channel and/or a KCNQ2/3 channel.

As used herein a "pharmaceutical composition" refers to a preparation of one or more of the compounds of the present invention (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising an SRI of the invention formulated in a compatible pharmaceutical carrier may also be prepared, placed in an appropriate container, and labeled for treatment of a particular medical condition, disease or disorder, as is detailed hereinabove.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

As discussed herein, some of the insights gained by the present inventors with respect to the design and development of novel potassium channel effectors and modulators, stemmed from an extensive SAR analysis conducted thereby. Without being bound by any particular theory, these studies raised the importance of some major binding pockets which constitute the ligand binding site of the potassium channel, as illustrated in FIG. 1. These binding pockets include a hydrophobic binding pocket and at least two electrophilic binding pockets. It was hypothesized by the present inventors that effective modulator compounds ought to at least exhibit chemical features which will affect the interaction between the compound and a hydrophobic binding pocket and at least two electrophilic binding sites in the voltage sensitive domain in the potassium channel. It was hypothesized that an effective blocker will be obtained by increasing the interaction of the compound with the hydrophobic pocket while not interacting with at least one of the electrophilic binding sites in the domain. Similarly, it was hypothesized that an effective opener will be obtained by increasing the interaction of the compound with the hydrophobic pocket as well as with at least two of the electrophilic binding sites in the domain.

Hence, according to yet another aspect of the present invention, there is provided a method of blocking a voltage-dependent potassium channel. This method is effected by administering to a subject in need thereof a therapeutically effective amount of a compound capable of interacting with a hydrophobic binding pocket in a voltage sensitive domain of a potassium channel, while not interacting with at least one electrophilic binding site in the voltage sensitive domain.

As further demonstrated in the Examples section that follows, using experimental constraints deduced from mutagenesis studies, docking experiments of the opener NH29, an exemplary compound according to the present embodiments, to its Kv7.2 channel site was performed. The results suggest that Kv7.2 channel modulators of the present invention act as gating-modifiers which may interact with the externally accessible surface of the VSD at the groove formed by the interface between S4 helix and S1-S2. Thus, these gating-modifiers can trap the VSD either in the inward resting conformation (blockers) or the outward activated conformation (openers).

Thus, according to additional features of the present invention the compound is capable of interacting with an externally accessible surface of said voltage sensitive domain at the groove formed by the interface between an S4 helix and S1-S2 in the voltage sensitive domain, and further trapping the voltage sensitive domain in an inward resting conformation thereof.

Accordingly, there is provided a method of opening a voltage-dependent potassium channel, effected by administering to a subject in need thereof a therapeutically effective amount of a compound capable of interacting with a hydrophobic binding pocket and with at least two electrophilic binding sites in a voltage sensitive domain of a potassium channel. Furthermore, according to further embodiments of the present invention, the compound is capable of interacting with an externally accessible surface of said voltage sensitive domain at the groove formed by an interface between a S4 helix and S1-S2 in said voltage sensitive domain, and further of trapping said voltage sensitive domain in an outward activated conformation thereof.

As discussed hereinabove, some the compounds described herein were tested and found to exhibit blocking of Transient receptor potential vanilloid 1 (TRPV1). These compound are derivatives of N-phenylanthranilic acid, which are derived from derivatives of N-phenylanthranilic acid described in WO2004/035037 and U.S. Patent Application No. 20050250833.

Thus, according to another aspect of the present invention there is provided a method of modulating Transient receptor potential vanilloid 1 (TRPV1), the method being effected by administering to a subject in need thereof a therapeutically effective amount of a compound having the general Formula IV:

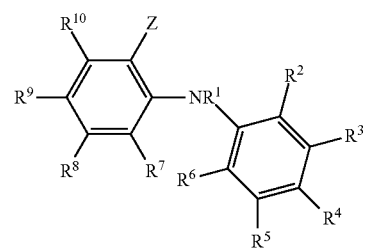

Formula IV wherein:
Z is an A-G(=K)—X—Y group,
and wherein:
A is alkyl or absent;
G is selected from the group consisting of C, S and PRa;
K is selected from the group consisting of O and S;
X is selected from the group consisting of NRb, O, S or absent; and
Y is selected from a group consisting of hydrogen, alkyl, hydroxyalkyl, cycloalkyl, heteroalicyclic, aryl and a polyalkylene glycol moiety;
$R^1$ is selected from the group consisting of hydrogen, alkyl, cycloalkyl or aryl;
each of $R^2$, $R^3$, $R^4$, $R^5$, $R^6$, $R^7$, $R^8$, $R^9$ and $R^{10}$ is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, amino and —$NR^{15}R^{16}$ or, alternatively, at least two of $R^2$, $R^3$, $R^4$, $R^5$ and $R^6$, of $R^7$, $R^8$, $R^9$ and $R^{10}$ form a five- or six-membered aromatic, heteroaromatic, alicyclic or heteroalicyclic ring;
$R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring; and
each of said Ra and Rb is selected from the group consisting of hydrogen, alkyl, cycloalkyl and aryl.

According to yet another aspect of the present invention there is provided a pharmaceutical composition which includes, as an active ingredient, the compound having the general Formula IV and a pharmaceutically acceptable carrier. In some embodiments, the composition is packaged in a packaging material and identified in print, in or on the packaging material, for use in the treatment of a condition in which modulating a TRPV1 channel is beneficial.

Accordingly, according to some embodiments of the present invention there is provided a use of the compound having the general Formula IV in the preparation of a medicament for the treatment of a condition in which modulating a TRPV1 channel is beneficial.

Additional features of the compounds utilized according to these aspects in the present embodiments are as described in WO2004/035037 and U.S. Patent Application No. 20050250833, which are incorporated by reference as if fully set forth herein.

In some embodiments, the compounds utilized in these aspects of the present invention comprise one or more electron-withdrawing substituents, as described herein for compounds having general Formula I.

As further described hereinabove and further in WO2004/035037 and U.S. Patent Application No. 20050250833, some of the compounds having general Formula IV, which are ester derivatives of N-phenylanthranilic acid, exhibit anti-COX activity, while other compounds, which are amide derivatives of N-phenylanthranilic acid, are devoid of COX inhibition activity.

As demonstrated in the Examples section which follows, NH29, an active compounds prepared according to embodiments of the present invention, has been shown to block TRPV1.

Hence according to some embodiments of the present invention the method of blocking TRPV1 in a subject in need thereof, comprises administering to the subject a therapeutically effective amount of NH29.

As discussed hereinabove, the lack of modulation of TRPV6 by the compounds of the present invention assures that administration of the compounds of the present invention to a subject in need thereof will not be accompanied by TRPV6-related adverse effects.

Thus, according to some embodiments of the present invention, the compounds presented herein do not modulate TRPV6.

In some embodiments, modulating TRPV1 activity comprises blocking TRPV1 activity, as defined herein.

There are many pathologies, conditions and disorders that are associated with TRPV1 channel functioning.

Exemplary medical conditions that are beneficially treatable by the TRPV1 blockers described herein (compounds having general Formula IV) include, but are not limited to, epilepsy, pain related conditions such as neurogenic pain, neuropathic pain, allodynia, pain associated with inflammation, bipolar disorder, mood disorder, psychotic disorder, schizophrenia, anxiety and a motor neuron disease, bladder overactivity and urinary incontinence.

As used herein the term "about" refers to ±10%

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Materials and Methods

Abbreviations

NHS: N-hydroxysuccinimide; t-Boc: t-butoxycarbonyl; DCM: dichloromethane; DMAP: dimethylaminopyridine; DMF: dimethyl formamide; DCC: dicyclohexylcarbodiimide; EtOAc: ethylacetate; He: hexanes; and TFA: trifluoroacetic acid.

All reactions requiring anhydrous conditions were performed in oven-dried glassware under an Argon or $N_2$ atmosphere.

Chemicals and solvents were either A.R. grade or purified by standard techniques.

Thin layer chromatography (TLC) was performed using silicagel 60 $F_{254}$ plates or silicagel preparative plates Analtech 1000 microns by Merck, and the compounds were visualized by irradiation with UV light and/or by treatment with a solution of 25 grams phosphomolybdic acid, 10 grams $Ce(SO_4)_2 \cdot H_2O$, 60 ml concentrated $H_2SO_4$ and 940 ml $H_2O$, followed by heating and/or by staining with a solution of 12 grams 2,4-dinitrophenylhydrazine in 60 ml concentrated $H_2SO_4$; 80 ml $H_2O$ and 200 ml 95% EtOH, followed by heating and/or immersing into an iodine bath (30 grams $I_2$, 2 grams KI, in 400 ml $EtOH/H_2O$ 1:1) and warming.

Flash chromatography (FC) was performed using silica gel Merck 60 (partical size 0.040-0.063 mm) by Merck, and eluent given in parentheses.

$^1$H NMR was performed using Bruker AMX 200 or 400. The chemical shifts are expressed in δ relative to TMS (δ=0 ppm) and the coupling constants J in Hz. The spectra were recorded in $CDCl_3$ or $CD_3OD$ as a solvent at room temperature unless stated otherwise.

HR-MS liquid secondary ionization (LSI-MS) was performed using VG ZAB-ZSE with 3-nitrobenzyl-alcohol matrix.

Meclofenamic acid and diclofenac are commercially available and were purchased from Sigma-Aldrich (St. Louis, Mo., USA).

Arachidonic acid and Indomethacin were purchased from Sigma.

Unless noted otherwise, all reagents, including salts and solvents, were purchased from Aldrich (Milwaukee, Minn.).

Chemical Syntheses

Preparation of Diclofenac Esters—General Procedure

The procedure for esterification of diclofenac is demonstrated for NH6, as described in U.S. Patent Application No. 20050250833.

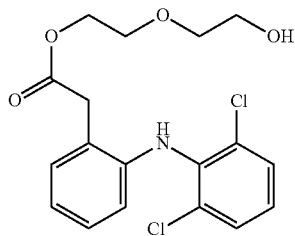

NH6

Diclofenac (50 mg, 0.17 mmol) was dissolved in dry DCM. Catalytic amount of DMAP and diethylene glycol (0.08 ml, 0.85 mmol) were added, and the stirred mixture was cooled to 0° C. Thereafter DCC (52.6 mg, 0.255 mmol) was dissolved in DCM and added dropwise to the reaction mixture. The suspension was then stirred at 0° C. for 30 minutes and monitored by TLC (EtOAc:He, 1:1). The precipitating solid was removed by filtration and washed with DCM. The filtrate was concentrated under reduced pressure and purified by flash chromatography over silica gel to afford the pure ester NH6 (43 mg, 66% yield).

NH6: $^1$H-NMR (200 MHz, $CDCl_3$): δ=7.35 ppm (2H, d, J=8); 7.19-7.06 (2H, m); 6.99 (1H, d, J=8); 6.96 (1H, d, J=8.); 6.56 (1H, d, J=8); 4.35 (2H, m); 3.8 (2H, s); 3.65-3.75 (4H, m); 3.53-3.57 (2H, m). MS (FAB): $[C_{18}H_{19}Cl_2NO_4]$ 383.0.

Preparation of Other Diclofenac Esters

Using the above general procedure, other diclofenac esters were prepared (see, U.S. Patent Application No. 20050250833), as illustrated in Scheme 1 below, and the yields and characterization thereof is listed below.

Scheme 1

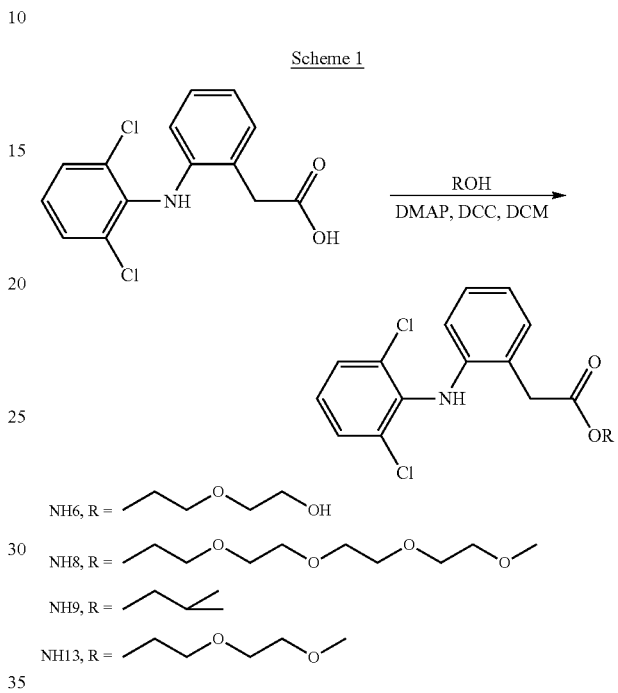

NH8: Yield 75%. $^1$HNMR (200 MHz, $CDCl_3$): δ=7.34 ppm (d, 2H, J=8.2); 7.24 (1H, dd, J=7.4, J=1.6); 7.08-7.16 (1H, dt, J=7.6, J=1.6); 6.91-7.02 (3H, m); 6.54 (1H, d, J=8); 4.3 (2H, m); 3.84 (2H, s); 3.55-3.74 (14H, m); 3.37 (3H, s). MS (FAB): $[C_{23}H_{29}Cl_2NO_6]$ 485.1

NH9: Yield 80%. $^1$HNMR (200 MHz, $CDCl_3$): δ=7.33 ppm (2H, d, J=8); 7.22 (1H, dd, J=7.4, J=1.6); 7.12 (1H, dt, J=7.6, J=1.6); 6.92-6.98 (3H, m); 6.55 (1H, d, J=8); 3.93 (2H, d, J=6.8); 3.82 (2H, s); 2.0 (1H, m); 0.91 (6H, d, J=6.8). MS (FAB): $[C_{18}H_{19}Cl_2NO_2]$ 351.1.

NH13: Yield 53%. $^1$HNMR (200 MHz, $CDCl_3$): δ=7.35 ppm (2H, d, J=8); 7.19-7.06 (2H, m); 6.99 (1H, d, J=8); 6.96 (1H, d, J=8.); 6.56 (1H, d, J=8); 4.34-4.29 (2H, m); 3.85 (2H, s); 3.75-3.70 (2H, m); 3.61-3.59 (2H, m); 3.58-3.50 (2H, m). MS (FAB): $[C_{19}H_{21}Cl_2NO_4]$ 397.0.

Preparation of Diclofenac N-Hydroxysuccinimide and Amide Derivatives—General Procedure The procedure for amidation of diclofenac derivatives is demonstrated for NH5 and NH14, as illustrated in Scheme 2 below and further described in U.S. Patent Application No. 20050250833.

N-Hydroxysuccinimide (0.76 mmol) and DCC (0.76 mmol) are added to a solution of the corresponding diclofenac acid derivative (0.506 mmol) dissolved in 10 ml of dichloromethane. The mixture is stirred for 1 hour and monitored by TLC (EtOAc:He, 1:1). When completion of the reaction is detected, the mixture is filtered and the solvent is evaporated under reduced pressure. The crude product is purified by column chromatography to afford the pure diclofenac amide derivative.

Scheme 2

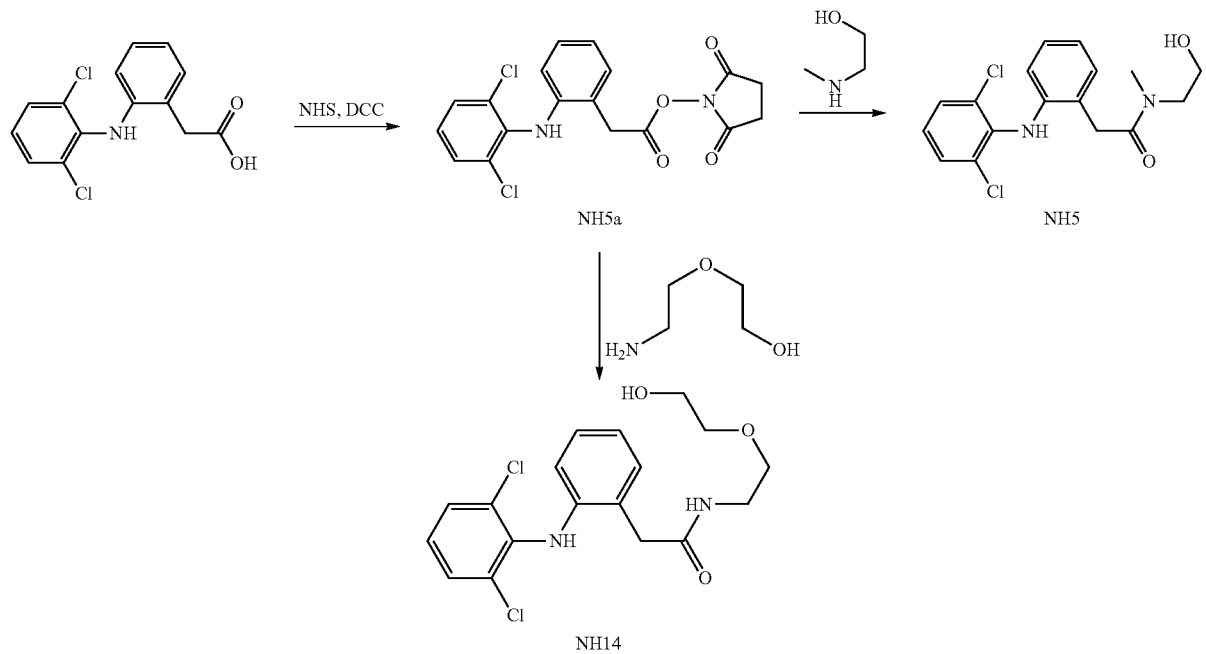

The N-hydroxysuccinimide derivative of the corresponding acid is dissolved in 1 ml of DMF. Diglycolamine (1 equivalent) is added and the mixture is stirred for 30 minutes while monitored by TLC (EtOAc, 100%). After completion of reaction the solvent is removed under reduced pressure and the product is purified by column chromatography to afford the corresponding amide derivative.

Preparation of Other Diclofenac N-Hydroxysuccinimide and Amide Derivatives

Using the above general procedure, other diclofenac N-hydroxysuccinimide and amide derivatives, presented in Scheme 3 below, were prepared as described in U.S. Patent Application No. 20050250833, and the yields and characterization thereof is listed below.

Scheme 3

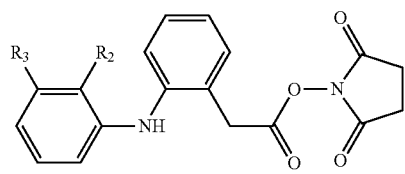

NH15a, $R_3 = R_2 = CH_3$
NH16a, $R_3 = CF_3, R_2 = H$
NH18a, $R_3 = Cl, R_2 = CH_3$

-continued

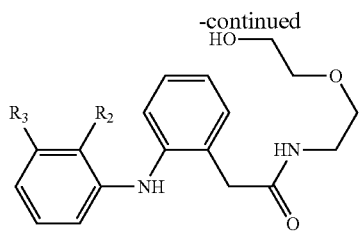

NH15, $R_3 = R_2 = CH_3$
NH16, $R_3 = CF_3, R_2 = H$
NH18, $R_3 = Cl, R_2 = CH_3$

NH5a: Yield 90%. $^1$HNMR (200 MHz, CDCl$_3$): δ=7.35 ppm (3H, d, J=8); 7.18-7.26 (1H, m); 6.93-7.07 (2H, m); 6.6-6.63 (1H, d, J=7.9); 6.2 (1H, s); 4.13 (2H, s); 2.84 (4H, s).

NH5: Yield 63%. $^1$HNMR (200 MHz, CDCl$_3$): δ=7.35 ppm (2H, d, J=8); 7.19-7.06 (2H, m); 6.99 (1H, d, J=8); 6.96 (1H, d, J=8); 6.56 (1H, d, J=8); 3.78-3.74 (2H, m); 3.64-3.57 (2H, m); 3.23 (2H, s); 2.95 (3H, s). MS (FAB): [$C_{17}H_{19}Cl_2N_2O_2$] 353.1.

NH14: Yield 78%. $^1$HNMR (200 MHz, CDCl$_3$) δ=7.35 ppm (2H, d, J=8); 7.19-7.06 (2H, m); 6.99 (1H, d, J=8); 6.96 (1H, d, J=8); 6.56 (1H, d, J=8); 3.69 (2H, s); 3.55-3.49 (4H, m). MS (FAB): [$C_{18}H_{20}N_2O_3Cl_2$+H] 383.1.

NH15a: Yield 99%. $^1$HNMR (200 MHz, CDCl$_3$): δ=8.6 ppm (1H, s); 8.12 (1H, dd, J=1.53, J=7.4); 7.32 (1H, m); 7.06-7.13 (m, 3H); 6.66-6.74 (2H, m); 2.9 (4H, s); 2.32 (3H, s); 2.14 (3H, s).

NH15: Yield 88%. $^1$HNMR (200 MHz, CDCl$_3$): δ=9.19 ppm (1H, s); 7.41-7.45 (1H, dd, J=1.53, J=7.4); 7.14-7.21 (2H, m); 7.02-7.10 (1H, t, J=7.7); 6.93-6.96 (2H, m); 6.65-6.69 (2H, m); 3.6-3.8 (8H, m); 2.32 (3H, s); 2.20 (3H, s). MS (FAB): [$C_{19}H_{24}N_2O_3$] 328.2.

NH16a: Yield 90%. $^1$HNMR (200 MHz, CDCl$_3$): δ=8.91 ppm (1H, s); 8.10-8.15 (1H, dd, J=1.6, J=8.18); 7.33-7.48 (5H, m); 7.24 (1H, d, J=7.8); 6.80-6.88 (1H, dt, J=1.06, J=7.1); 2.9 (4H, s).

NH16: Yield 79%. $^1$HNMR (200 MHz, CDCl$_3$): δ=9.44 ppm (1H, s); 7.46-7.50 (1H, dd, J=0.6, J=8); 7.4 (2H, d, J=9); 7.16-7.32 (5H, m); 7.09 (1H, bs); 6.79-6.84 (1H, dt, J=1.8, J=6.5); 3.54-3.73 (8H, m). MS (FAB): [C$_{18}$H$_{19}$N$_2$O$_3$F$_3$+H] 369.1.

NH18a: Yield 92%. $^1$HNMR (200 MHz, CDCl$_3$): δ=8.69 ppm (1H, s); 8.09-8.14 (1H, dd, J=1.7, J=8.6); 7.32-7.37 (1H, dt, J=1.8, J=8.5); 7.14-7.28 (3H, m); 6.72-6.80 (2H, m); 2.9 (4H, s); 2.29 (3H, s).

NH18: Yield 86%. $^1$HNMR (200 MHz, CDCl$_3$): δ=9.31 ppm (1H, s); 7.45-7.50 (1H, dd, J=0.6, J=8); 6.99-7.22 (5H, m); 6.67-6.94 (1H, dt, J=1.8, J=6.5); 3.54-3.74 (8H, m); 2.33 (3H, s). MS (FAB): [C$_{18}$H$_{21}$N$_2$O$_3$Cl+H] 349.1.

Preparation of NH17

Compound NH17, an exemplary blocker of voltage-dependent potassium channels according to an embodiment of the present invention, was prepared from Compound 1, as illustrated in Scheme 4 below.

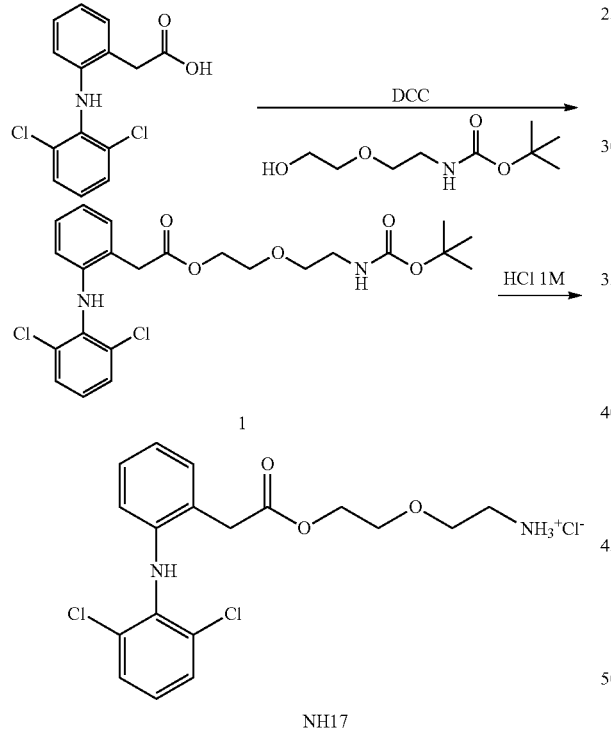

Scheme 4

Diclofenac (100 mg, 0.338 mmol) was dissolved in DCM. Thereafter N-boc-diglycolamine (70 mg, 0.34 mmol) [Kim, Y. S.; Kim, K. M.; Song, R.; Jun, M. J.; Sohn, Y. S., *J. Inorg. Biochem.* 2001, 87(3), 157-163] and DMAP (4 mg, 0.034 mmol) were added. To this mixture DCC (139 mg, 0.68 mmol) DCM was added dropwise. The reaction mixture was stirred at room temperature for 1 hour while monitoring by TLC (EtOAc:He, 1:1). Upon completion of the reaction, the mixture was filtered and the solvent was removed under reduced pressure. The crude product was purified by column chromatography on silica gel (EtOAc:He, 1:3) to afford Compound 1 (148 mg, 90%) in the form of a color less oil.

Compound 1: $^1$HNMR (200 MHz, CDCl$_3$): δ=7.34 ppm (d, J=8 Hz, 2H); 7.28 (dd, J=7.4, 1.5 Hz, 1H); 7.14 (dt, J=7.4, 1.5 Hz, 1H); 7.02-6.93 (m, 2H); 6.87 (s, 1H); 6.57 (d, J=7.9 Hz, 1H); 4.31-4.26 (m, 2H); 3.84 (s, 2H) 3.68-3.63 (m, 2H); 3.47 (t, J=5.0 Hz, 2H); 3.27 (q, J=5.0 Hz, 2H); 1.43 (s, 9H).

Compound 1 (127 mg, 0.26 mmol) was dissolved in 10 ml DCM, and 3 ml of a solution of HCl (1M) in ether was added thereto. The mixture was stirred at room temperature overnight and monitored by TLC (EtOAc:MeOH, 9:1). Upon completion of the reaction, the solvents were removed under reduced pressure to afford NH17 (29 mg, 27% yield) in the form of a white powder which was used without further purification.

NH17: $^1$HNMR (200 MHz, CDCl$_3$): δ=7.32 ppm (d, J=8.0 Hz, 2H); 7.26-7.22 (m, 1H); 7.12 (t, J=8.0 Hz, 1H); 7.0-6.92 (m, 2H); 6.81 (s, 1H); 6.51 (d, J=7.6 Hz, 1H); 4.30 (bs, 2H); 3.84 (s, 2H); 3.76 (bs, 4H); 3.25 (bs, 2H).

Preparation of NH21

Compound NH21, an exemplary blocker of voltage-dependent potassium channels according to an embodiment of the present invention, was prepared as illustrated in Scheme 5 below.

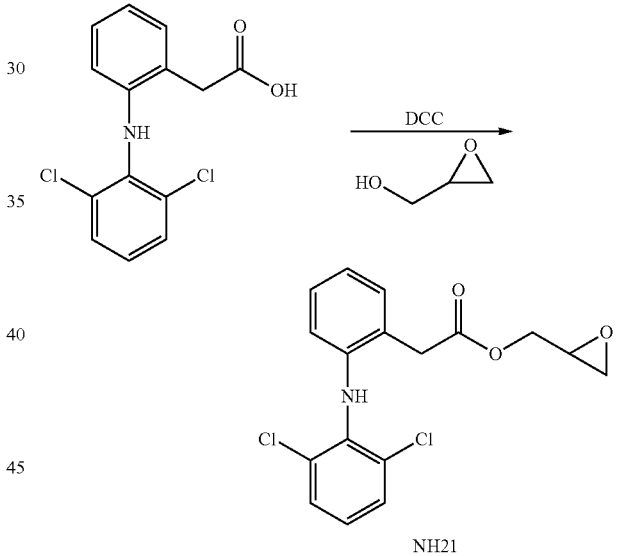

Scheme 5

Diclofenac (200 mg, 0.67 mmol) was dissolved in DCM, and glycidol (60 mg, 0.81 mmol) and DMAP (8 mg, 0.07 mmol) were added thereto. Thereafter DCC (276 mg, 1.34 mmol) dissolved in DCM was added dropwise to the reaction mixture which was stirred at room temperature overnight and monitored by TLC (EtOAc:He, 1:3). Upon completion of the reaction, the mixture was filtered and the solvent was removed under reduced pressure. The crude product was purified by column chromatography on silica gel (EtOAc:He, 1:3) to afford NH21 (138 mg, 60% yield) in the form of a white powder.

NH21: $^1$HNMR (200 MHz, CDCl$_3$): δ=7.34 ppm (d, J=8.0 Hz, 2H); 7.28 (dd, J=7.4, 1.5 Hz, 1H); 7.14 (dt, J=7.4, 1.5 Hz, 1H); 7.02-6.93 (m, 2H); 6.87 (s, 1H); 6.57 (d, J=7.9 Hz, 1H); 4.49 (dd, J=12.0, 3.0 Hz, 1H); 4.01 (dd, J=12.0, 6.0 Hz, 1H); 3.88 (s, 2H); 3.21 (m, 1H); 2.82 (t, J=4.8 Hz, 1H); 2.62 (dd, J=4.8, 2.6 Hz, 1H)

Preparation of NH25

Compound NH25, an exemplary opener of voltage-dependent potassium channels according to an embodiment of the present invention, was prepared from Compound 2, as illustrated in Scheme 6 below.

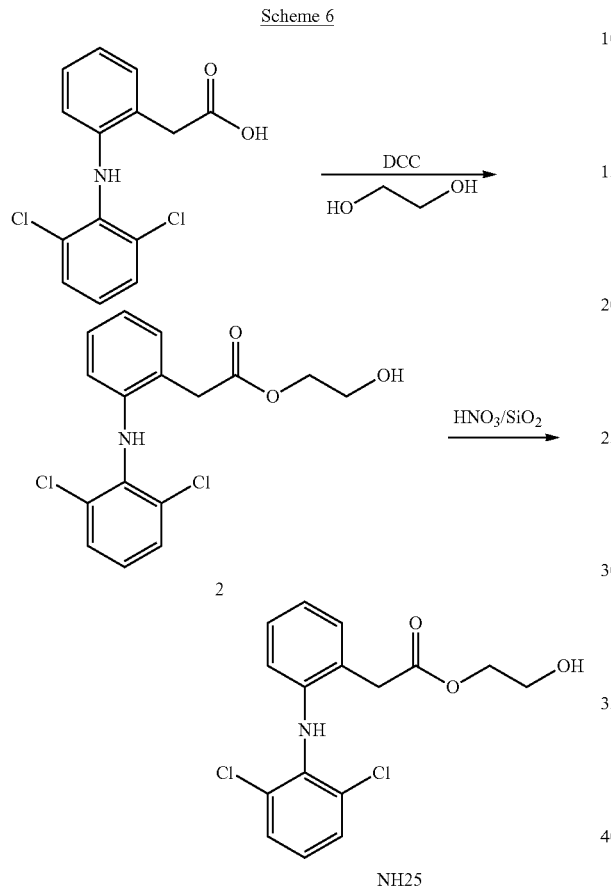

Diclofenac (300 mg, 1 mmol) was dissolved in DCM, and ethylene glycol (300 mg, 5 mmol) and DMAP (8 mg, 0.07 mmol) were added thereto. Thereafter DCC (240 mg, 1.2 mmol) dissolved in DCM was added dropwise to the reaction mixture which was stirred for 10 minutes at room temperature and monitored by TLC (EtOAc:Hex, 1:1). Upon completion of the reaction, the mixture was filtered and the solvent was removed under reduced pressure. The crude product was purified by column chromatography on silica gel (EtOAc:He, 1:3) to afford Compound 2 (270 mg, 80% yield) in the form of white powder.

Compound 2: $^1$HNMR (200 MHz, CD$_3$OD) δ=7.37 (d, J=8.5 Hz, 2H); 7.19 (dd, J=9.0, 2.5 Hz, 1H); 7.09-7.00 (m, 2H); 6.86 (t, J=8.0 Hz, 1H); 6.37 (d, J=9.0 Hz, 1H); 4.18 (t, J=5.0 Hz, 2H); 3.82 (s, 2H); 3.72 (t, J=5.0 Hz, 2H).

Compound 2 (150 mg, 0.45 mmol) was dissolved in DCM, and nitrated silica gel (375 mg, 1 equivalent) was added thereto [Fleming, S. A.; Ridges, M. D.; Jensen, A. W, *J. Label. Compd. Radiopharm.*, 1996, 38(1), 13-18]. The reaction mixture was stirred at room temperature for 10 minutes and monitored by TLC (EtOAc: He, 1:1). Upon completion of the reaction, the silica was filtered and the solvent was removed under reduced pressure. The crude product was purified by column chromatography on silica gel (EtOAc:He, 2:3) to afford compound NH25 (100 mg, 60% yield) in the form of an orange powder.

NH25: $^1$HNMR (200 MHz, CD$_3$OD) δ=8.13 (d, J=2.5 Hz, 1H); 7.93 (dd, J=9.0, 2.5 Hz, 1H); 7.49 (d, J=8.5 Hz, 2H); 7.27 (t, J=8.5 Hz, 1H); 6.23 (d, J=9.0 Hz, 1H); 4.21 (t, J=5.0 Hz, 2H); 3.89 (s, 2H); 3.74 (t, J=5.0 Hz, 2H).

Preparation of NH27

Compound NH27, an exemplary opener of voltage-dependent potassium channels according to an embodiment of the present invention, was prepared as illustrated in Scheme 7 below.

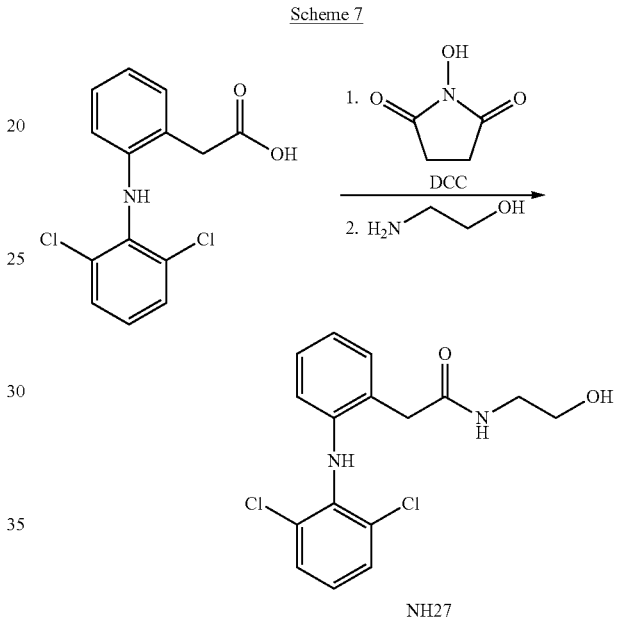

Diclofenac (600 mg, 2 mmol) was dissolved in DCM, and NHS (260 mg, 2.2 mmol) and DMAP (16 mg, 0.14 mmol) were added thereto. Thereafter DCC (500 mg, 2.4 mmol) dissolved in DCM was added dropwise to the reaction mixture which was stirred for 10 minutes at room temperature and monitored by TLC (EtOAc:He, 3:1). Upon completion of the reaction, the reaction mixture was filtered and the solvent was removed under reduced pressure.

The residue was dissolved in DMF, and ethanol amine (135 mg, 2.2 mmol) was added thereto. The mixture was stirred for 10 minutes at room temperature and monitored by TLC (EtOAc:He, 3:1). Upon completion the reaction, the mixture was diluted with EtOAc and washed with saturated solution of ammonium chloride. The organic layer was dried over magnesium sulfate and the solvent was removed under reduced pressure. The crude product was purified by column chromatography on silica gel (EtOAc:He, 3:2) to afford NH27 (570 mg, 84% yield) in the form of white powder.

NH27: $^1$HNMR (400 MHz, CD$_3$OD) δ=7.37 (d, J=8.5 Hz, 2H); 7.19 (dd, J=9.0, 2.5 Hz, 1H); 7.05-6.99 (m, 2H); 6.86 (t, J=8.0 Hz, 1H); 6.37 (d, J=8.0 Hz, 1H); 3.67 (s, 2H); 3.57 (t, J=5.0 Hz, 2H); 3.29 (t, J=5.0 Hz, 2H).

Preparation of NH28, NH29 and NH30

Compounds NH28, NH29 and NH30, exemplary openers of voltage-dependent potassium channels according to embodiments of the present invention, were prepared from Compound NH27, as illustrated in Scheme 8 below.

Scheme 8

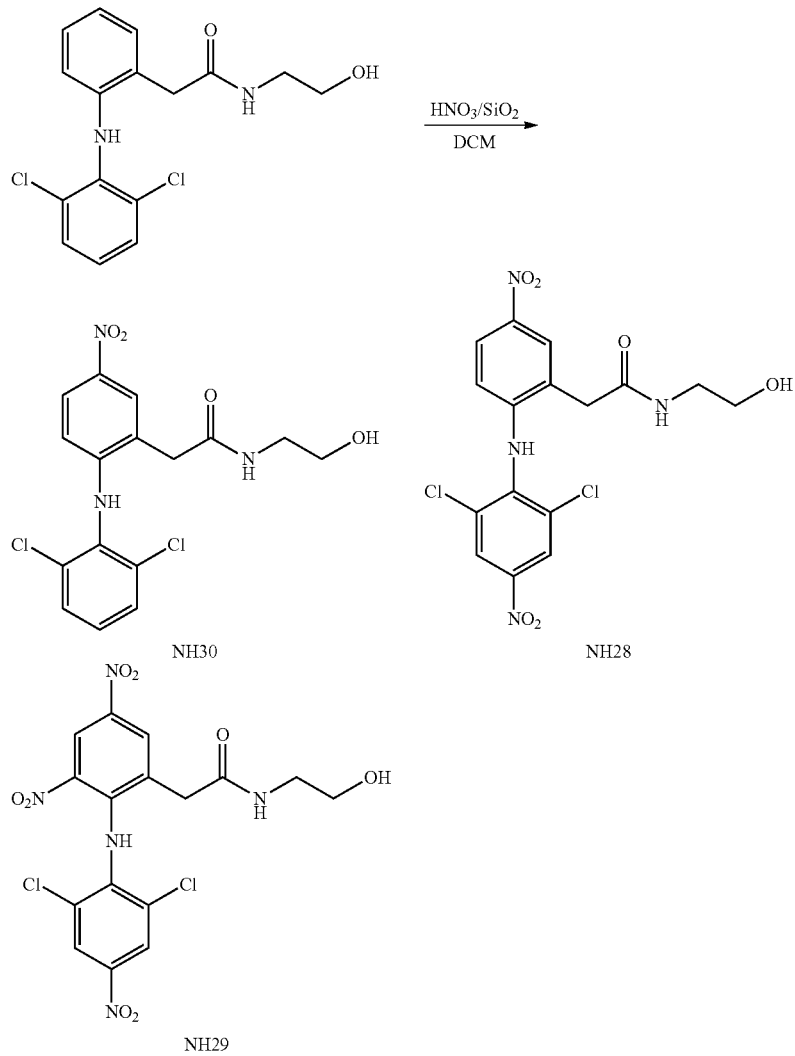

NH28 was prepared from NH27 as follows: NH27 (200 mg, 0.59 mmol), prepared as presented hereinabove, was dissolved in DCM, and nitrated silica gel (900 mg, 2 equivalents) was added thereto. The reaction was stirred at room temperature for 2 hours and monitored by TLC (EtOAc:He, 7:3). Upon completion of the reaction, the silica was filtered and the solvent was removed under reduced pressure. The crude product was purified by column chromatography on silica gel (EtOAc:He, 7:3) to afford NH28 (50 mg, 20% yield) in the form of a yellow powder.

NH28: $^1$HNMR (400 MHz, CD$_3$OD) δ=8.39 (s, 2H); 8.24 (d, J=2.5 Hz, 1H); 8.06 (dd, J=9.0, 2.5 Hz, 1H); 6.71 (d, J=9.0 Hz, 1H); 3.82 (s, 2H); 3.63 (t, J=5.0 Hz, 2H); 3.35 (t, J=5.0 Hz, 2H).

NH29 was prepared from NH27 as follows: NH27 (200 mg, 0.59 mmol) was dissolved in DCM, and nitrated silica gel (1.35 gr, 3 equivalents) was added thereto. The reaction was stirred at room temperature for 2 hours and monitored by TLC (EtOAc:He, 7:3). Upon completion of the reaction, the silica was filtered and the solvent was removed under reduced pressure. The crude product was purified by column chromatography on silica gel (EtOAc:He, 7:3) to give NH29 (80 mg, 30% yield) in the form of a yellow powder.

NH29: $^1$HNMR (200 MHz, CD$_3$OD) δ=8.59 (d, J=2.5 Hz, 1H); 8.44 (d, J=2.5 Hz, 1H); 8.22 (s, 2H); 3.86 (s, 2H); 3.56 (t, J=5.0 Hz, 2H); 3.27 (t, J=5.0 Hz, 2H).

NH30 was prepared from NH27 as follows: NH27 (100 mg, 0.30 mmol), prepared as presented hereinabove, was dissolved in DCM and nitrated silica gel (250 mg, 1 equivalent) was added thereto. The reaction mixture was stirred at room temperature for 2 hours and monitored by TLC (EtOAc: He, 7:3). Upon completion of the reaction, the silica was filtered and the solvent was removed under reduced pressure. The crude product was purified by column chromatography on silica gel (EtOAc:He, 7:3) to afford NH30 (30 mg, 25% yield) in the form of a yellow powder.

NH30: $^1$HNMR (200 MHz, CD$_3$OD) δ=8.15 (d, J=2.5 Hz, 1H); 7.94 (dd, J=9.0, 2.5 Hz, 1H); 7.49 (d, J=8.5 Hz, 2H); 7.23 (t, J=8.5 Hz, 1H); 6.30 (d, J=9.0 Hz, 1H); 3.72 (s, 2H); 3.59 (t, J=5.0 Hz, 2H); 3.30 (t, J=5.0 Hz, 2H).

Table 1 presents some exemplary compounds which were prepared and tested, some of which are in accordance with embodiments of the present invention.

TABLE 1
| Compound | Structure |
|---|---|
| NH5 | 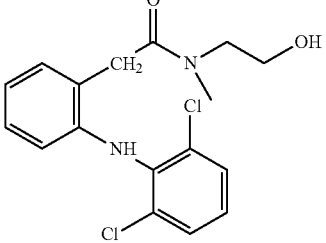 |
| NH6 | 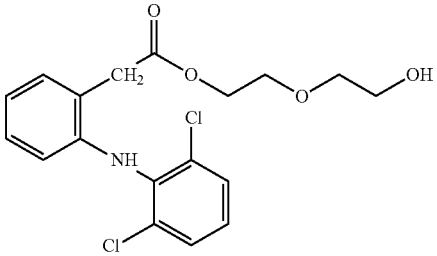 [SMILES: O=C(Cc1ccccc1Nc1c(Cl)cccc1Cl)OCCOCCO] |
| NH7 | 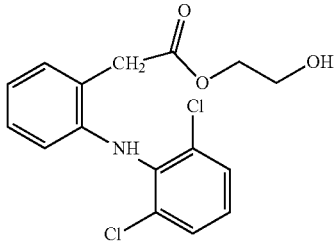 [SMILES: O=C(Cc1ccccc1Nc1c(Cl)cccc1Cl)OCCO] |
| NH8 | 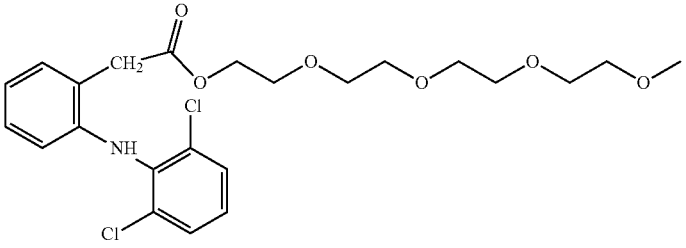 [SMILES: COCCOCCOCCOCCOC(=O)Cc1ccccc1Nc1c(Cl)cccc1Cl] |
| NH9 | 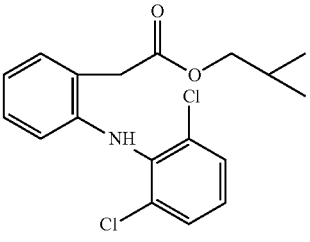 [SMILES: CC(C)COC(=O)Cc1ccccc1Nc1c(Cl)cccc1Cl] |
| NH10 | 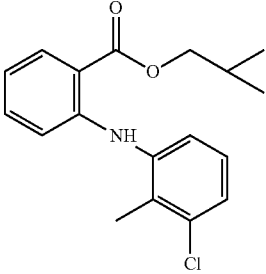 [SMILES: Cc1c(Cl)cccc1Nc1ccccc1C(=O)OCC(C)C] |

TABLE 1-continued
| Compound | Structure |
|---|---|
| NH11 | 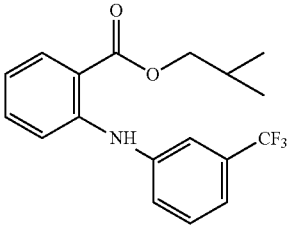 [SMILES: CC(C)COC(=O)c1ccccc1Nc1cccc(C(F)(F)F)c1] |
| NH12 | 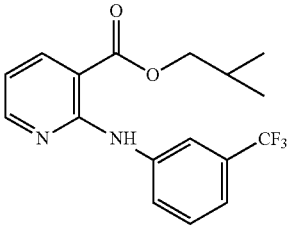 [SMILES: CC(C)COC(=O)c1cccnc1Nc1cccc(C(F)(F)F)c1] |
| NH13 | 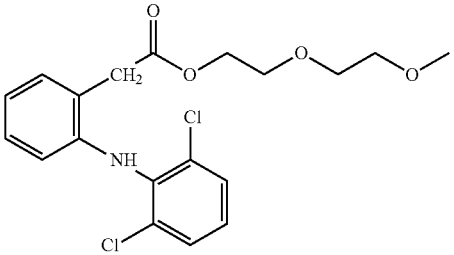 [SMILES: COCCOCCOC(=O)Cc1ccccc1Nc1c(Cl)cccc1Cl] |
| NH14 | 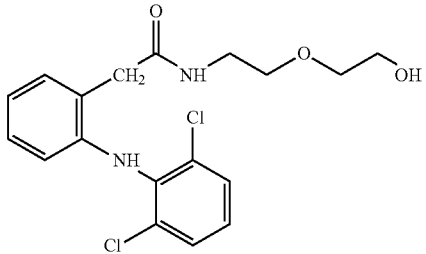 [SMILES: O=C(Cc1ccccc1Nc1c(Cl)cccc1Cl)NCCOCCO] |
| NH15 | 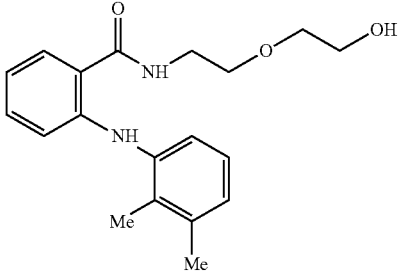 [SMILES: Cc1cccc(Nc2ccccc2C(=O)NCCOCCO)c1C] |
| NH16 | 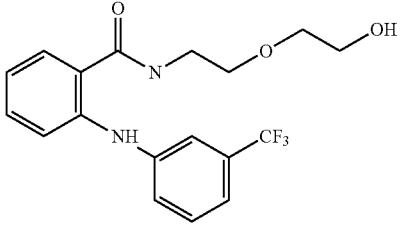 [SMILES: O=C(NCCOCCO)c1ccccc1Nc1cccc(C(F)(F)F)c1] |

TABLE 1-continued

| Compound | Structure |
|---|---|
| NH17 | (structure: 2-[(2,6-dichlorophenyl)amino]phenylacetic acid 2-(2-aminoethoxy)ethyl ester, hydrochloride salt) |
| NH18 | (structure: 2-[(3-chloro-2-methylphenyl)amino]-N-[2-(2-hydroxyethoxy)ethyl]benzamide) |
| NH19 | (structure: 9-oxo-9,10-dihydroacridine-4-carboxylic acid N-[2-(2-hydroxyethoxy)ethyl]amide) |
| NH 20 | (structure: diphenylamine-2,2'-dicarboxamide, each amide N-[2-(2-hydroxyethoxy)ethyl]) |
| NH 21 | (structure: 2-[(2,6-dichlorophenyl)amino]phenylacetic acid glycidyl ester) |

TABLE 1-continued
| Compound | Structure |
|---|---|
| NH 22 | 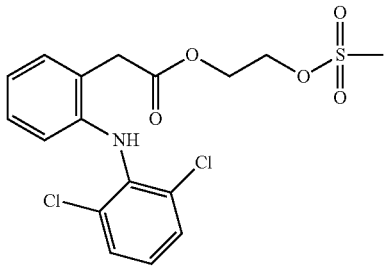 [SMILES: CS(=O)(=O)OCCOC(=O)Cc1ccccc1Nc1c(Cl)cccc1Cl] |
| NH 23 | 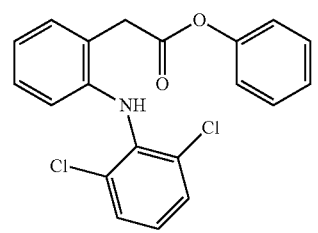 [SMILES: O=C(Cc1ccccc1Nc1c(Cl)cccc1Cl)Oc1ccccc1] |
| NH 24 | 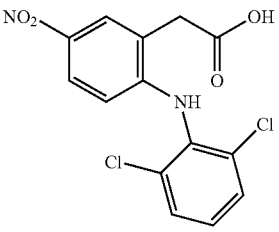 [SMILES: O=C(O)Cc1cc([N+](=O)[O-])ccc1Nc1c(Cl)cccc1Cl] |
| NH 25 | 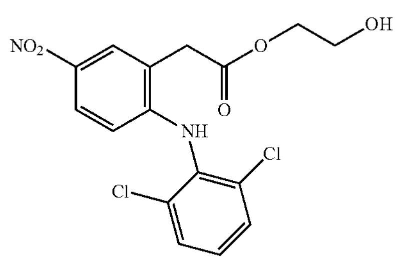 [SMILES: O=C(Cc1cc([N+](=O)[O-])ccc1Nc1c(Cl)cccc1Cl)OCCO] |
| NH 26 | 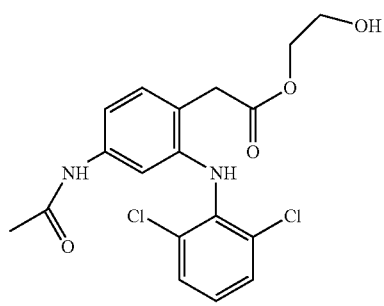 [SMILES: CC(=O)Nc1ccc(CC(=O)OCCO)c(Nc2c(Cl)cccc2Cl)c1] |
| NH 27 | 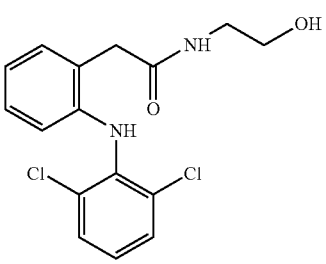 [SMILES: O=C(Cc1ccccc1Nc1c(Cl)cccc1Cl)NCCO] |

TABLE 1-continued

| Compound | Structure |
|---|---|
| NH 28 | (structure: 2-((2,6-dichloro-4-nitrophenyl)amino)-5-nitrophenyl-N-(2-hydroxyethyl)acetamide) |
| NH 29 | (structure: 2-((2,6-dichloro-4-nitrophenyl)amino)-3,5-dinitrophenyl-N-(2-hydroxyethyl)acetamide) |
| NH 30 | (structure: 2-((2,6-dichlorophenyl)amino)-5-nitrophenyl-N-(2-hydroxyethyl)acetamide) |
| NH 31 | (structure: 2-((2,6-dichloro-4-nitrophenyl)amino)-3,5-dinitrophenyl-N-(2-(nitrooxy)ethyl)acetamide) |

Activity Assays

Recombinant Expression of Kv7.2/3, TRPV1 and TRPV6 Channels in CHO Cells

Chinese hamster ovary (CHO) cells were grown in Dulbecco's modified Eagle's medium (DMEM) supplemented with 2 mM glutamine, 10% fetal calf serum and antibiotics. Briefly, 40,000 cells seeded on poly-D-lysine-coated glass coverslips (13 mm diameter) in a 24-multiwell plate were transfected with pIRES-CD8 (0.5 μg) as a marker for transfection, and with Kv7.2 (0.5 μg) and Kv7.3 (0.5 μg) or TRPV1 (1 g) or TRPV6 (1 g).

For electrophysiology, transfected cells were visualized approximately 40 hours following transfection, using anti-CD8 antibody-coated beads. Transfection was performed using Fugene 6 (Roche, Indianapolis Ind., USA) according to the manufacturer's protocol.

Dorsal Root Ganglion and Neuronal Hippocampal Primary Cultures:

Recent work suggested that M-currents play a key role in controlling the excitability of sensory dorsal root ganglion (DRG) neurons and may therefore represent a therapeutic target for the treatment of pain [4]. Hence, measuring the effects of novel M-channel modulators on DRG neuronal excitability is of important value, considering their potential impact on nociceptive signaling pathways.

For dorsal root ganglion (DRG) neuronal cultures, ganglia were dissected from 2-5 day-old Sprague-Dawley rats killed by decapitation. DRGs were placed in Hank's balanced saline solution (HBSS) and prepared by enzymatic dissociation. Briefly, after 30 minutes incubation in 5 mg/ml dispase, 2 mg/ml collagenase type 1A and 0.1 mg/ml DNase (Invitrogen/Gibco, Carlsbad, Calif.) in $Ca^{2+}$ and $Mg^{2+}$-free HBSS, the ganglia were mechanically triturated with a fire-polished glass Pasteur pipette. The ganglia were then centrifuged for 5 minutes at 80×g and resuspended in DMEM supplemented with 2 mM L-glutamine, 16.5 mM $NaHCO_3$, 6 g/l glucose, 5 ml penicillin/streptomycin and 10% fetal calf serum.

For electrophysiological recording, dissociated neurons were plated on 13 mm glass coverslips, previously coated with poly-D-lysine (1 mg/ml) and laminin (10 µg/ml) and used at 1-2 days in culture.

For hippocampal neuronal cultures, Sprague-Dawley rat embryos (E18) were removed by caesarian section and their hippocampi were dissected out. The tissue was digested with papain for 20 min, triturated to a single-cell suspension, and plated at a density of 40,000 cells per ml on a substrate of bovine collagen type IV and 100 µg/ml poly-L-lysine in 13 mm diameter glass coverslips of a 24-multiwell plate. The culture medium consisted of Modified Eagle's Medium containing 5% horse serum (Biological Industries, Beit HaEmek, Israel), B-27 neuronal supplement (Invitrogen, Carlsbad, Calif.), 100 U/ml penicillin, 100 µg/ml streptomycin, and 2 mM glutamine. D-glucose was supplemented to a final concentration of 6 g/l. Cytosine-1-D-arabinofuranoside (5 µM) was added after 5 days to arrest glial cell proliferation.

For electrophysiological recordings hippocampal neurons were used at 10-14 days in culture. All cultures were maintained at 37° C. in humidified air containing 5% $CO_2$.

Maximal Electroshock Seizure Test:

The anti-convulsant effect was measured by the maximal electroshock seizure model (MES) in ICR mice as previously described [1]. The procedures followed for experimentation and maintenance of the animals were approved by the animal research ethics committee of Tel Aviv University and in accordance with the Guide for the Care and Use of Laboratory Animals (1996, National Academy of Sciences, Washington D.C.). Briefly, maximal electroshock was induced in adult mice by means of two transcorneal electrodes delivering an alternative current of 50 mA at 60 Hz for 0.2 sec using rodent shocker (Hugo Sachs Electronik, type 221). This was shown to cause tonic convulsions in 100% of the animals tested. The compounds, dissolved in 0.9% saline, were administered intraperitoneally 30 minutes before the electroshock was performed. Animals failing to show tonic hind limb extension were scored as protected and were expressed in percentage.

Electrophysiology:

Voltage-clamp recordings in CHO cells were performed, using the whole-cell configuration of the patch-clamp technique. Signals were amplified using an Axopatch 200B patch-clamp amplifier (Molecular Devices, Sunnyvale, Calif.), sampled at 2 kHz and filtered at 800 Hz via a 4-pole Bessel low pass filter. Data were acquired using pClamp 9.2 software (Molecular Devices) and an IBM compatible Pentium IV computer in conjunction with a DigiData 1322A interface (Molecular Devices). The patch pipettes were pulled from borosilicate glass (Warner Instrument Corp, USA) with a resistance of 2-5 MΩ. For $K^+$ current recordings in CHO cells, the intracellular pipette solution contained (in mM): 130 KCl, 1 $MgCl_2$, 5 $K_2ATP$, 5 EGTA, 10 HEPES, adjusted with KOH to pH 7.4 (290 mOsm). The extracellular solution contained (in mM): 140 NaCl, 4 KCl, 1.8 $CaCl_2$, 1.2 $MgCl_2$, 11 glucose, 5.5 HEPES, adjusted with NaOH to pH 7.4 (310 mOsm). Series resistances (3-13 MΩ) were compensated (75-90%) and periodically monitored.

For current-clamp recordings in primary cultured neurons, the patch pipettes were filled with (in mM): 135 KCl, 1 $K_2ATP$, 1 $MgATP$, 2 EGTA, 1.1 $CaCl_2$, 5 glucose, 10 HEPES, adjusted with KOH at pH 7.4 (315 mOsm). The external solution contained (in mM): 150 NaCl, 2.5 KCl, 2 $CaCl_2$, 2 $MgCl_2$, 15 glucose, 10 HEPES, adjusted with NaOH at pH 7.4 (325 mOsm). Recordings were sampled at 5 kHz and filtered at 2 KHz via a 4-pole Bessel low pass filter. A liquid junction potential of about −15.6 mV was measured between the intracellular and saline solutions and corrected on-line.

For evoking spike discharges, 75-200 pA square depolarizing current pulses were injected into neurons for 400 ms. For rheobase current measurements, 100-1100 pA square depolarizing current pulses were injected into neurons for 2 ms.

Spontaneous excitatory postsynaptic currents (EPSCs) were recorded in the voltage-clamp configuration of the whole-cell patch-clamp technique at a holding potential of −70 mV as previously described [5]; the extracellular solution contained (in mM) 160 NaCl, 2.5 KCl, 10 HEPES, 10 glucose, 2 $CaCl_2$; pH 7.3 (325 mOsm), to which 30 µM picrotoxin and 10 µM bicuculline methyl iodide were added. The intracellular solution consisted (in mM) of 130 K-gluconate, 10 KCl, 1.1 EGTA, 10 HEPES, 1 $MgCl_2$, 2 $Na_2ATP$, 0.1 $CaCl_2$ and 5 QX314Br to block $Na^+$ currents; pH 7.2 (315 mOsm).

Spontaneous inhibitory postsynaptic currents (IPSCs) were recorded at a holding potential of −70 mV; the extracellular solution contained (in mM) 160 NaCl, 2.5 KCl, 10 HEPES, 10 glucose, 2 $CaCl_2$; pH 7.3 (325 mOsm), to which 10 µM NBQX and 10 µM AP-5 were added. The intracellular solution consisted (in mM) of 144 CsCl, 10 HEPES, 1.1 EGTA, 0.1 $CaCl_2$, 5 $MgCl_2$, 2 $Na_2ATP$, 5 QX314 Br; pH 7.3 (315 mOsm).

Voltage-clamp measurements in *Xenopus* oocytes were performed as previously described [1].

Cyclooxygenase Inhibition Assay in Cell Culture:

Mouse colon adenocarcinoma CT26 and mouse lewis lung carcinoma D122 cells were grown in DMEM (D122) or RPMI (CT26) supplemented with 10% fetal calf serum, 4% glutamine, 1% penicillin-streptomycin-nystatin and 3% non essential amino acids (D122) and were kept in a humidified 37° C. incubator with 5% $CO_2$. For the COX activity assays, cells were grown onto 24 multi-well plates.

Before the assay, cells were washed with serum-free medium; then the tested compounds were added to the medium and incubated for 30 minutes at 37° C. after which 30 µM arachidonic acid were added and incubated for additional 20 minutes. At the end of the incubation period, 10 µM Indomethacin were added to stop the reaction and medium was transferred to another 24 multi-well plate for measuring PGE2 production by radioimmunoassay (DuPont-NEN; Boston Mass.) according to manufacturer protocol. Protein determination was assayed on scraped cells using the Bradford method (1976) [Bradford M. M. 1976. *Anal. Biochem.* 72:248-254], with BSA as a standard and was used to normalize the amount of PGE2 production.

99Data Analyses:

Data analysis was performed using the Clampfit program (pClamp 9.2, Molecular Devices), Microsoft Excel (Microsoft) and Prism 4.0 (GraphPad). Chord conductance (G) was calculated by using the following equation:

$$G = I/(V - V\text{rev})$$

where I corresponds to the current amplitude measured at the end of the pulse and Vrev, the calculated reversal potential. G was estimated at various test voltages V and then, normalized to a maximal conductance value, Gmax. Activation curves were fitted by one Boltzmann distribution:

$$G/G\text{max} = 1/\{1 + \exp[(V_{50} - V)/s]\}$$

where $V_{50}$ is the voltage at which the current is half-activated and s is the slope factor. All data were expressed as mean±SEM. Statistically significant differences were assessed by Student's t-test. Analysis of sEPSCs and sIPSCs was done using the Clampfit program (pClamp 9.2, Molecular Devices) and included evaluation of the individual events as well as the average event amplitude and the integral of the event (total charge transfer).

Channel Modulation Activity Assays Results and Analysis

SAR Studies:

Considering the M-channel modulation activity, several important features could be deduced from the structure-activity relation (SAR) study. The results of this study are summarized in Table 2 below and are depicted in FIG. 1.

Table 2 presents a summary of the results of SAR studies conducted for exemplary compounds according to embodiments of the present invention, showing the functionality of several structural features on the M-channel modulation activity for each compound. In these studies, the impact of the compounds on M-channel activity was measured by the heterologous coexpression of Kv7.2 and Kv7.3 subunits in CHO cells. The $EC_{50}$ values in μM represent the average values of opener potency as determined by the concentration-dependent left-shift in the half-activation potential $\Delta V_{50}$ (mV) and fitted by a sigmoidal function (n=3-5).

diclofenac, and meclofenamate), an ester group (see, for example, NH6, NH7 or NH25) as well as an amide function (see, for example, NH14, NH29, NH30 or NH15). The opener activity was also displayed by derivatives bearing either ether or alkyl chains (see, for example, NH14, NH7, NH6, NH27, NH28, NH29 and NH30).

Since the main opener effect of the various compounds is to cause a hyperpolarizing shift of the activation curve of Kv7.2/3 channels, the extent of the left-shift ($\Delta V_{50}$) is considered a true to the source measure of the opener potency. As can also be seen in Table 2, this SAR study has shown that substituting the aromatic rings with potent electron-withdrawing groups, such as nitro ($NO_2$), increased the left-shift in activation significantly. In the ester series, compound NH7 is a much weaker opener ($\Delta V_{50}$=−4.1 mV) than compound NH25 which bears one $NO_2$ group ($\Delta V_{50}$=−31.0 mV). Similarly, in the amide series, compound NH29 possessing three $NO_2$ is a stronger opener ($\Delta V_{50}$=−31.3 mV) than compound NH30 which bears only one $NO_2$ group ($\Delta V_{50}$=−12.2 mV).

The diphenylamine moiety itself appears to be important for activating the M-channels. It was found that the NSAID compounds lacking this group but still bearing a carboxylate function like ibuprofen, flurbiprofen, ketoprofen, fenoprofen or naproxen, do not activate Kv7.2/3 channels, while those bearing both functionalities (diphenylamine and carboxylate)

TABLE 2

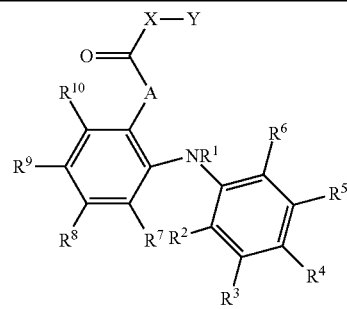

| Compound | A | X | Y | $R_2$ | $R_6$ | $R_3$ | $R_9$ | $R_7$ | $R_4$ | Activity | $EC_{50}$ (μM) | $\Delta V_{50}$ (mV) |
|---|---|---|---|---|---|---|---|---|---|---|---|---|
| Diclofenac | $CH_2$ | O | H | Cl | Cl | H | H | H | H | Opener | 2.6 | −14.5 |
| NH5 | $CH_2$ | $NCH_3$ | $(CH_2)_2OH$ | Cl | Cl | H | H | H | H | Opener | — | — |
| NH14 | $CH_2$ | NH | $((CH_2)_2O)_2H$ | Cl | Cl | H | H | H | H | Opener | 7 | −12.6 |
| NH24 | $CH_2$ | O | H | Cl | Cl | H | $NO_2$ | H | H | Opener | — | — |
| NH27 | $CH_2$ | NH | $(CH_2)_2OH$ | Cl | Cl | H | H | H | H | Opener | — | — |
| NH28 | $CH_2$ | NH | $(CH_2)_2OH$ | Cl | Cl | H | $NO_2$ | H | $NO_2$ | Opener | — | — |
| NH29 | $CH_2$ | NH | $(CH_2)_2OH$ | Cl | Cl | H | $NO_2$ | $NO_2$ | $NO_2$ | Opener | 14 | −31.3 |
| NH30 | $CH_2$ | NH | $(CH_2)_2OH$ | Cl | Cl | H | $NO_2$ | H | H | Opener | 17 | −12.2 |
| NH6 | $CH_2$ | O | $((CH_2)_2O)_2H$ | Cl | Cl | H | H | H | H | Opener | 18 | −18.7 |
| NH7 | $CH_2$ | O | $(CH_2)_2OH$ | Cl | Cl | H | H | H | H | Opener | — | −4.1 |
| NH8 | $CH_2$ | O | $((CH_2)_2O)_4CH_3$ | Cl | Cl | H | H | H | H | Inactive | — | — |
| NH9 | $CH_2$ | O | isobutyl | Cl | Cl | H | H | H | H | Blocker | 50 | — |
| NH13 | $CH_2$ | O | $((CH_2)_2O)_2CH_3$ | Cl | Cl | H | H | H | H | Inactive | — | — |
| NH17 | $CH_2$ | O | $(CH_2)_2O(CH_2)_2NH_3^+Cl^-$ | Cl | Cl | H | H | H | H | Blocker | 11 | — |
| NH21 | $CH_2$ | O | methyloxirane | Cl | Cl | H | H | H | H | Blocker | 100 | — |
| NH25 | $CH_2$ | O | $(CH_2)_2OH$ | Cl | Cl | H | $NO_2$ | H | H | Opener | 22 | −31 |
| Meclofenamic | — | O | H | Cl | Cl | $CH_3$ | H | H | H | Opener | 25 | −22.7 |
| NH15 | — | NH | $((CH_2)_2O)_2H$ | $CH_3$ | H | $CH_3$ | H | H | H | Opener | 3 | −8.4 |
| NH16 | — | NH | $((CH_2)_2O)_2H$ | H | H | $CF_3$ | H | H | H | Opener | 9 | −5.5 |
| NH18 | — | NH | $((CH_2)_2O)_2H$ | $CH_3$ | H | Cl | H | H | H | Opener | 6 | −3.7 |
| NH10 | — | O | isobutyl | $CH_3$ | H | Cl | H | H | H | Inactive | — | — |
| NH11 | — | O | isobutyl | H | H | $CF_3$ | H | H | H | Inactive | — | — |

As can be seen in Table 2, the active M-channel openers can accommodate carboxylate, ester and amide functionalities. As can further be seen in Table 2, the active opener compounds bear a carboxylate (see, for example, NH24, such as N-phenylanthranilic acid drugs (mefenamate, tolfenamate, or flufenamate) are all potent M-channel openers.

The results presented herein also indicate that a terminal hydroxyl group in the ether or alkyl chain has a notable impact on the activity of the compounds as M-channel openers. For example, NH8, NH13, NH10 and NH11 whose terminal hydroxyl function has been replaced by methyl or isobutyl groups are totally inactive with respect to Kv7.2/3 channels. Remarkably, potent M-channel blockers are obtained in the case of NH9, NH17 and NH21 where the terminal hydroxyl has been replaced by isobutyl, ethylamine and 2,3-epoxypropyl groups, respectively.

Another insight which is gained from the results presented in Table 2 above is the notable effect of a positive or protonatable group in the Y variable. An ammonium group in this position makes a blocker which is about ten times more effecting than a blocker with an epoxide in the same position, and 5 time more effective than a blocker with an isobutyl group.

It was further observed that when the group denoted A in Formulae III is a methylene group and not absent, the resulting compound is rendered inactive, as seen for NH10 and NH11 as opposed to the active blocker NH9, all of which share the same isobutyl moiety in the Y variable (see, Table 2 hereinabove).

Inhibition of Kv7.2/7.3 Currents in CHO Cells and Hyperexcitabilty of DRG Neurons by M-Channel Blockers:

FIG. 2 presents the results obtained for compound NH17. NH17 was studied in inhibition assays against the voltage-dependent potassium channel Kv7.2/3, showing that NH17 inhibits currents and enhances firing of peripheral DRG neurons, in representative traces recorded from the same CHO cell before (FIG. 2A, left panel) and after (FIG. 2A, right panel) external application 25 μM of NH17, wherein the membrane potential was stepped from −90 mV holding potential to +50 mV for 1.5 second pulse duration in 10 mV increments, followed by a repolarizing step to −60 mV. NH17 was further assayed in current density-voltage relations (n=6) in the absence (marked by empty squares in FIG. 2B,) and presence of 25 μM of NH17 (marked by solid squares FIG. 2B).

As can be seen in FIG. 2A and FIG. 2B, when tested on recombinant Kv7.2/3 channels that were heterologously expressed in CHO cells, NH17 produced a blockade of the K$^+$ currents (IC$_{50}$=11 μM) both potently and dose-dependently. At a concentration of 25 μM, NH17 produced more than 90% inhibition of the Kv7.2/3 current at a wide range of membrane potentials (from −60 to +50 mV).

As discussed hereinabove, M-currents may represent a therapeutic target for the treatment of pain [4]. Therefore, exemplary compounds were examined in the current-clamp configuration for the effect thereof on spike activity of cultured rat DRG neurons.

FIG. 2C and FIG. 2D present the results of these studies as conducted for NH17, which was assayed in representative rat DRG spiking discharge, evoked by a squared depolarizing current pulse (10 pA for 400 msec) before (control), and during exposure to 1 μM of NH17 for 1, 2 and 3 minutes (FIG. 2C), and also in representative trace of spontaneously spiking DRG neuron previously exposed for 5 minutes to 1 μM of NH17 (FIG. 2D).

As can be seen in FIG. 2C and FIG. 2D, a single spike discharge pattern was evoked by injecting a minimal depolarizing current pulse (about 10 pA, 400 ms). Within 2 minutes, external application of 1 μM NH17 depolarized the DRG membrane potential (ΔV=+7±1 mV) and potently increased the number of evoked spikes (about 10-20 pA for 400 ms, from 1±0 to 12±2; n=5, p<0.01) (FIG. 2C). The hyperexcitability profile of NH17 (1 μM) on spike generation was reflected by a decrease in rheobase current of about 300 pA that is needed to generate a single spike (for a 2 ms injection, from 650±71 pA to 347±44 pA, n=6; p<0.01). The hyperexcitability discharge pattern induced by the M-channel blocker NH17 was so strong that in some cases, it could lead the DRG neurons to fire spontaneously, with no need of injecting depolarizing current (FIG. 2D). These results indicate that NH17 is a potent M-channel blocker and lead to neuronal hyperexcitability.

Enhancement of Kv7.2/7.3 Currents in CHO Cells and Hyperexcitabilty of Hippocampal and DRG Neurons by Nitro-Containing Derivatives of N-Phenylanthranilic Acid:

FIG. 3 presents the results obtained for compound NH25, an exemplary ester derivative according to embodiments of the present invention, which possess one electron-withdrawing nitro group at position R$^9$ on the ester-bearing phenyl ring, and a hydroxy group at the end of the ester moiety denoted Y in Formula I.

The left panel of FIG. 3A shows representative traces of Kv7.2/3 channels expressed in CHO cells as measured for NH25. The right panel of FIG. 3A shows that external application of NH25 enhanced Kv7.2/3 currents at nearly all voltages.

Like other compounds described herein which displayed opener activity, the effects of NH25 were voltage-dependent. As the test potentials were more positive (above −10 mV), the effects of NH25 became weaker on current amplitude. As can be seen in FIG. 3B and FIG. 2D, when membrane potential was stepped every 30 seconds from −90 to −50 mV, application of 10 μM and 50 μM of NH25 produced 3.2-fold and 9.1-fold increase in current amplitude, respectively (n=10). The channel modulator action had a fast onset as within one minute of superfusion of NH25, the current increased significantly. As can be seen in FIG. 3E and FIG. 3F, analysis of the conductance/voltage relationships clearly shows that the activating effect of NH25 mainly arises from a left-shift in the Kv7.2/3 activation curve. For example, 10 μM, 50 μM and 200 μM of NH25 produced left-shifts of −11 mV, −21 mV and −31 mV respectively compared to control, with no change in the Boltzmann slopes ($V_{50}$=−32.1±8.9 mV, n=19; $V_{50}$=−43.6±9.0 mV, n=5; $V_{50}$=−53.5±9.3 mV, n=5 and $V_{50}$=−63.1±2.0 mV, n=5, respectively).

FIGS. 4A-D present the results of other assays which characterized the opener activity of NH25 as concentration-dependent, quantified by the extent of the left-shift ($\Delta V_{50}$), yielding an EC$_{50}$ of 22 μM. As can be seen in FIG. 4A and FIG. 4B, NH25 (50 μM) also affected Kv7.2/3 gating by accelerating the activation kinetics (from $t_{1/2}$=296±63 ms to $t_{1/2}$=171±29 ms, n=6; p<0.05). As can be seen in FIG. 4C and FIG. 4D, comparison of the tail currents at −60 mV revealed that NH25 markedly slowed down the deactivation kinetics of Kv7.2/3 channels (from $\tau_{deact}$=129±22 ms to $\tau_{deact}$=284±43 ms; n=5, p<0.01).

FIG. 5 presents the results of other experiments conducted for the exemplary compound NH25, characterizing it with respect to its effect on central and peripheral neurons, using the current-clamp mode of the whole-cell patch-clamp technique in rat primary cultures of hippocampal and DRG neurons. As can be seen in FIG. 5A and FIG. 5D, repetitive spike discharges were evoked by depolarizing current injections. External application of 25 μM of NH25 depressed the number of evoked action potentials robustly and reversibly in both hippocampal and DRG neurons (from 9.6±1.0 to 2.1±0.5, n=8 and from 10.4±0.8 to 0.8±0.3, n=8 respectively; 75-200 pA for 400 ms; p<0.01). As can further be seen in FIG. 5B, exposure to 25 μM NH25 hyperpolarized the resting membrane potential of DRG neurons by −8.3±0.2 mV (from −60.6±0.3 mV to −69.0±0.3 mV, n=13; p<0.01). A similar hyperpolarization was also obtained in hippocampal neurons exposed to NH25 (−8.5 mV). As can be seen in FIG. 5C and FIG. 5E, reflecting the dampening action of NH25 on spike generation, the rheobase current needed to be injected into DRG neurons to generate a single spike, was increased upon exposure to the drug (for a 2 ms injection, from 400±41 pA to 577±38 pA, n=12; p<0.01).

Because of their slow activation and their lack of inactivation, M-channels could modulate neuronal activity during repetitive spike discharge and tune neurotransmitter release. FIG. 6 illustrates the effect of NH25 on synaptic transmission and transmitter release. Spontaneous excitatory and inhibitory post-synaptic currents (sEPSCs and sIPSCs) were recorded from dense cultures of primary hippocampal neurons, using the voltage-clamp configuration of the whole-cell patch-clamp technique. The sIPSCs were recorded at a holding potential of −70 mV and were pharmacologically isolated by blocking NMDA and AMPA receptor-mediated excitatory postsynaptic currents (with 10 μM AP-5 and 10 μM NBQX); sIPSCs were exclusively mediated by the activation of $GABA_A$ Cl⁻ channels as they could be completely blocked with 30 μM picrotoxin and 10 μM bicuculline (data not shown). Hence, sIPSCs reflect the synaptic release of GABA.

As can be seen in FIGS. 6A-C, NH25 (25 μM) inhibited sIPSCs powerfully and reversibly, mainly by depressing their frequency of spontaneous occurrence (more than 98% inhibition). NH25 did not significantly affect the amplitude and the kinetics of the currents. Spontaneous EPSCs were recorded at −70 mV and were pharmacologically isolated by blocking $GABA_A$ receptor-mediated inhibitory post-synaptic currents (with 10 μM bicuculline and 30 μM picrotoxin). The sEPSCs were solely mediated by the activation of AMPA receptors and to a lesser extent of NMDA receptors, as they were blocked by 10 μM NBQX (an AMPA receptor antagonist) and 10 μM AP-5 (a selective NMDA receptor antagonist). Thus, sEPSCs reflect the synaptic release of glutamate. Under control conditions, sEPSCs appeared as repetitive bursts whose frequency was variable, ranging from 0.3 to 2 Hz and increasing with the density of the hippocampal culture. As can be seen in FIGS. 6D-F, application of NH25 markedly reduced the burst duration of sEPSCs without a significant effect on the amplitude. Consequently, as can further be seen in FIGS. 6D-F, NH25 reduced by about 50% the total charge transfer as well as the charge transfer within the bursts. Interestingly, activation of M-channels by NH25 did not affect the amplitude and the kinetics of miniature EPSCs and IPSCs (data not shown).

Given its dampening action on neuronal spiking discharges, a possible anti-convulsant effect of NH25 in the maximal electroshock seizure (MES) model in mice was tested. This test is generally thought to be a model of generalized tonic-clonic seizure in human [6]. MES produced hind limb extension in all mice that received intraperitoneal injection of vehicle solution.

As can be seen in FIG. 6G, intraperitoneal injection of NH25 30 minutes before the electroshock, dose-dependently (1-40 mg/kg) protected the animals against the tonic extension caused by MES, with an $ED_{50}$ of 12 mg/kg. For comparison, intraperitoneal injection of phenyloin and sodium valproate 30 minutes before the electroshock fully prevented hind limb extension at doses of 20 mg/kg and 500 mg/kg, respectively (data not shown).

FIG. 7 presents the results obtained for compound NH29, an exemplary amide derivative according to embodiments of the present invention, which possesses three electron-withdrawing nitro groups at positions $R^4$, $R^7$ and $R^9$, and a hydroxy group at the end of the amide moiety, denoted Y in Formula I. The channel modulation activity of the exemplary amide NH29 on recombinant Kv7.2/3 channels expressed in CHO cells and its properties on primary cultured neurons were tested.

Superfusion of NH29 enhanced Kv7.2/3 currents at all voltages. As can be seen in FIG. 7A, like NH25, the activating effects of NH29 became weaker when membrane voltage was stepped to more positive potentials. At −50 mV, a physiologically relevant subthreshold potential, 25 μM of NH29 increased Kv7.2/3 current amplitude by 9.4±1.2 fold (n=5). The activating effect of NH29 mostly originated from a left-shift of the Kv7.2/3 activation curve. For example, as can further be seen in FIG. 7B and FIG. 7C, 10 μM and 100 μM of NH29 produced left-shifts of −13 mV and −31 mV, respectively, compared to control. As can be seen in FIG. 7C, NH29 dose-dependently activated Kv7.2/3 channels, a feature quantified by the concentration dependent left-shift ($\Delta V_{50}$), yielding an $EC_{50}$ of 14 μM.

As can be seen in FIG. 7D and FIG. 7F, superfusion of 25 μM of NH29 reduced the number of evoked action potentials in DRG neurons powerfully and reversibly (from 8.7±0.8 to 0.9±0.1, n=12; 75-250 pA for 400 ms; p<0.001). As an be seen in FIG. 7G, exposure to 25 μM NH29 hyperpolarized the resting membrane potential of DRG neurons by −9.0±1.9 mV (from −56.0±2.2 mV to −65.0±3.4 mV, n=7; p<0.01). As can be seen in FIG. 7E, the rheobase current needed to generate a single spike in DRG neurons was increased upon exposure to NH29 (for a 2 ms injection, from 178±36 pA to 300±55 pA, n=8; p<0.005).

The selectivity of NH29 on other relevant Kv channels expressed in *Xenopus* oocytes was also studied, and the results are summarized in Table 3 below. The specificity of NH29 at 25 μM and 50 μM towards various Kv channels was tested in *Xenopus* oocytes, except for Kv1.2 which was checked in transfected CHO cells. The current amplitude of the various Kv channels was tested at the indicated voltages and the effect of the drugs was expressed as fold of the control amplitude measured under the same conditions in the absence of the drug. The data in Table 3 are expressed as mean±SEM of 5-7 separate experiments.

TABLE 3

| | Fold current amplitude | |
|---|---|---|
| K⁺ channel subtype | 25 μM of NH29 | 50 μM of NH29 |
| Kv11.1 or Herg (−10 mV) | 1.1 ± 0.02 | 0.9 ± 0.08 |
| Kv1.2 (0 mV) | 0.9 ± 0.01 | 0.66 ± 0.03* |
| Kv 2.1 (+30 mV) | 1.2 ± 0.09 | 1.2 ± 0.11 |
| Kv 4.3 (+30 mV) | 1.1 ± 0.04 | 1.0 ± 0.07 |
| Kv7.2 (−40 mV) | 3.5 ± 0.4* | 6.8 ± 0.7* |
| Kv 7.4 (−30 mV) | 1.0 ± 0.12 | 0.9 ± 0.04 |
| Kv 7.1 (+30 mV) | 0.93 ± 0.02 | 0.72 ± 0.02* |
| $I_{KS}$ (+30 mV) | 1.02 ± 0.04 | 0.97 ± 0.04 |

*significance p < 0.01

As can be seen in Table 3, except for a moderate inhibition of Kv1.2 and Kv7.1 currents (34% and 23%, respectively), 50 μM of NH29 did not affect the current amplitude of Kv11.1 (Herg), Kv2.1 and Kv4.3. Among the Kv7 channel family, NH29 appeared to act as an opener of Kv7.2 but not of Kv7.1 and Kv7.4. NH29 could also activate Kv7.3 when tested on the Kv7.3 mutant A315T [7]. Notably, NH29 (25 μM) did not affect the amplitude of miniature excitatory and inhibitory post-synaptic currents (mEPSCs and mIPSCs) in cultured hippocampal neurons, suggesting that it does not interact with AMPA/NMDA and $GABA_A$ channels (data not shown). The remarkable selective opener activity of NH29 for M-channels versus other Kv channels, including the cardiac Kv11.1

(Herg) and $I_{KS}$ and other neuronal K$^+$ currents, is promising, and more so when considering that NH29 is selective for Kv7.2/3 channels and does not activate Kv7.4, which is a distinctive feature compared to that of the well known channel opener retigabine [8].

Modulation of TRPV1 Currents in CHO Following the Application of Nitro-Containing Amide Derivatives of N-Phenylanthranilic Acid:

The ability of the exemplary compound NH29 to modulate the activity of Transient receptor potential vanilloid 1 (TRPV1) was also examined. TRPV1 is a nonselective ligand-gated cation channel that may be activated by a wide variety of exogenous and endogenous stimuli, including heat (at temperature higher than 43° C., pH (lower than 6), and chemical interactions with anandamide, N-arachidonoyl-dopamine, or capsaicin. TRPV1 is a member of the Transient receptor potential family of membrane proteins and is found in the central nervous system and the peripheral nervous system. TRPV1 channels are involved, inter alia, in the transmission and modulation of pain, as well as the integration of diverse painful stimuli.

By a reciprocal analogy with tarantula toxins (VaTx1), whose target site appears to be the voltage sensing domains (VSD) and which are blockers of Kv2.1 potassium channels and openers of TRPV1 channels, it was hypothesized that Kv7.2 opener such as the exemplary opener compound NH29 would modulate TRPV1 channels activity by blocking their activity.

Thus, the binding of NH29 to TRPV1 channels was tested. CHO cells were transfected with TRPV1 channels and the channels were activated with 0.5 μM capsaicin (CAP) followed by external application of NH29 at a concentration range of 5-50 M. The results are presented in FIG. 13A and show that NH29 potently inhibited TRPV1 channels. Similar inhibition was seen also in DRG sensory neurons (see, FIG. 14). The channel inhibition was reversible, as can be deduced from the regained activity of the channel once the NH29 compound was washed out (see, FIG. 13B). The calculated $IC_{50}$ for TRPV1 inhibition by NH29 was 4.2 M.

The specificity of NH29 inhibition activity towards TRPV1 was tested by comparing the data obtained for TRPV1 and TRPV6 (the latter being another member of the Transient receptor potential family of membrane proteins).

As can be seen in FIGS. 13A and 13B, it was found that NH29 specifically inhibits TRPV1 since no similar inhibition of TRPV6 was observed (see, FIG. 15 A-C). TRPV6 is a membrane calcium channel which is responsible for the first step in calcium absorption in the intestine. Thus, the lack of modulation of TRPV6 by NH29 assures normal absorption of calcium, through this channel, in the intestine of a patient treated with NH29.

In conclusion, the obtained data show that the compounds described herein exhibit inhibition (blocking) of TRPV1 channels. The involvement of TRPV1 in the transduction of nociceptive pain signals is well known and thus inhibition of these channels subsequently leads to reduction of pain.

Anti-COX Activities of NH 25, NH29 and NH30 in Cell Culture:

The anti-COX activity of NH25, NH29 and NH30 was examined in Mouse colon adenocarcinoma CT26 and mouse lewis lung carcinoma D122 cell lines. Cells were incubated with each of the tested compounds and the level of the COX-dependent synthesis of $PGE_2$ was quantified using radioimmunoassay techniques. The results are presented in Table 4 and show that the amidic derivatives NH29 and NH30 did not exhibit anti-COX activity, while the esteric derivative NH25 exhibited anti-COX activity comparable to that of Diclofenac.

TABLE 4

| compound | COX inhibition (IC50) CT26 cells | COX inhibition (IC50) D122 cells |
|---|---|---|
| Diclofenac | 0.003 | 0.1 |
| NH25 | 0.048 | 0.229 |
| NH29 | >50 | >50 |
| NH30 | >50 | >50 |

Mapping of the Channel Pharmacophore

In an attempt to deduce more intricate details of the channel pharmacophore, the present inventors have tested one of the more potent channel openers, Compound NH29, for activity against various KCNQ subunits and mutants.

FIG. 8 presents a bar-graph comparing the potentiating effect of 25 μM of Compound NH29 on various KCNQ subunits and mutants, wherein the opener effect is expressed as percent of the control current in the absence of the opener.

As can be seen in FIG. 8, the exemplary opener Compound NH29 is acting specifically on KCNQ2 subunits and not on homomeric KCNQ1 and KCNQ4 channels, and no opening activity was detected with homomeric KCNQ3 channels. However, this lack of detectable effect is possibly due to the very small currents that are flowing through homomeric KCNQ3. Nevertheless, the opening activity of the channel activating compounds presented herein is highly notable on heteromeric KCNQ2/KCNQ3 channels.

Among the four membrane-spanning segments forming the voltage sensing domain (VSD), the charged S4 helix is relatively more conserved in sequence within voltage-gated ion channels, than the other segments S1-S3 and their connecting linkers which are rather divergent. It is expected that small ligand interactions with the VSD occur via a docking surface and "a transduction site".

It is postulated that the docking site should involve the relatively conserved charged S4 helix, while the "transduction site" that confers specificity of the VSD-ligand interface and is necessary for the channel conformational change, should comprise more divergent regions of the VSD such as for example the external S1-S2 and S3-S4 linkers. FIG. 9 presents a computer generated structural model of two adjacent voltage sensing domains (VSD) in the KCNQ2 channel (S-numbered helices colored in gold and purple) which interact therebetween during channel activation, and residue R207 in the S4 helix (colored in salmon) which when mutated renders the channel much less sensitive to the opener NH29, an exemplary compound according to the present embodiments (see, FIG. 10), that may dock in the groove formed by the interface between S1, S2 and S4 helices within a VSD.

FIGS. 10A-D present the effect of NH29 on wild type KCNQ2 (FIGS. 10A and 10B) and R207W mutant (FIGS. 10C and 10D) channels, as expressed in activation curve measurements, and show that NH29 left-shifts the activation curve as well as enhances the current amplitude of the WT KCNQ2 to a significantly larger extent as compared to the mutant, thus suggesting that R207 is located in the NH29 binding site.

The Kv7.2 channel modulators described herein are gating modifiers which could interact with the externally accessible surface of the VSD at the groove formed by the interface between S4 helix and S1-S2, thereby stabilizing the VSD in the activated conformation. Thus, like scorpion toxins on voltage-gated Na$^+$ channels or tarantula toxins on voltage-gated K$^+$ channels, these ligands may act by trapping the VSD either in the inward resting conformation (blockers) or the outward activated conformation (openers).

Recent studies (Schenzer et al. 2005; Wuttke et al. 2005) suggested that retigabine binds to a hydrophobic pocket formed upon channel opening between the cytoplasmic parts of S5 and S6 (see, FIG. 9). The present results show that the various openers presented herein do not interact with the binding site of retigabine.

FIGS. 11A-E present representative traces, showing the effects of retigabine (RTG) and NH29 on the channel activity of KCNQ2 mutants W236L and R207W.

As can be seen in FIG. 11, the point mutation R207W in S4 completely abolished the opener effect of 25 µM NH29 (FIG. 11A) but not that of 25 µM retigabine (RTG, FIG. 11B). In contrast, the point mutation W236L in S5 completely abolished the opener effect of 10 µM retigabine (RTG) but not that of 10 µM or 25 µM NH29 (FIGS. 11D and 11E, respectively). The results are summarized in FIG. 11F and suggest that NH29 binding site is different than that of retigabine.

The results presented herein therefore show that the binding site of the opener compounds presented herein maps the voltage sensor domain (VSD) of the KCNQ2 subunit at residues which are located at the interface of the S1-S2 and S4 α helices (see, FIG. 9).

While further exploring the binding domains of the compounds in the VSD, additional results of mutation studies (see, FIGS. 12A-F) showed that mutation of amino acids located at the S4 helix (FIG. 12D-12F) rather than the S1-S2 helix (FIG. 12A-C) lead to loss of activity of NH29.

Notably, it was found that the S4 mutant residues L197G, R198A, R201A, R207W, I209L and to a lesser extent R214W are significantly less sensitive to the activating effect of the opener NH29, compared to wild-type Kv7.2 channels. While 25 M NH29 enhances WT Kv7.2 currents by 3.5-fold, it increases the current of L197G, R198A, R201A, R207W by only 1.5-, 1.6-, 1.2- and 1.5-fold, respectively (p<0.01; FIG. 12D and). An example of a trace recorded from a CHO cell transfected with one of the only three S4 mutations in which the NH29 activity was preserved (L206C) is presented in FIG. 12E and an example of a trace recorded from a CHO cell transfected with an S4 mutation which abolished NH29 activity (R201A) is presented in FIG. 12F.

In contrast, all these S4 mutants are still strongly sensitive to the opener action of Retigabine (RTG) which acts on the channel gate. For example, RTG increases the current amplitude of mutant R207W by more than 6-fold (FIG. 11B) and that of mutant R198A by 4.4-fold. In addition, the recently characterized Kv7 opener, Zinc pyrithione, was also shown to activate very potently the S4 mutant R207W.

Figure 12A:
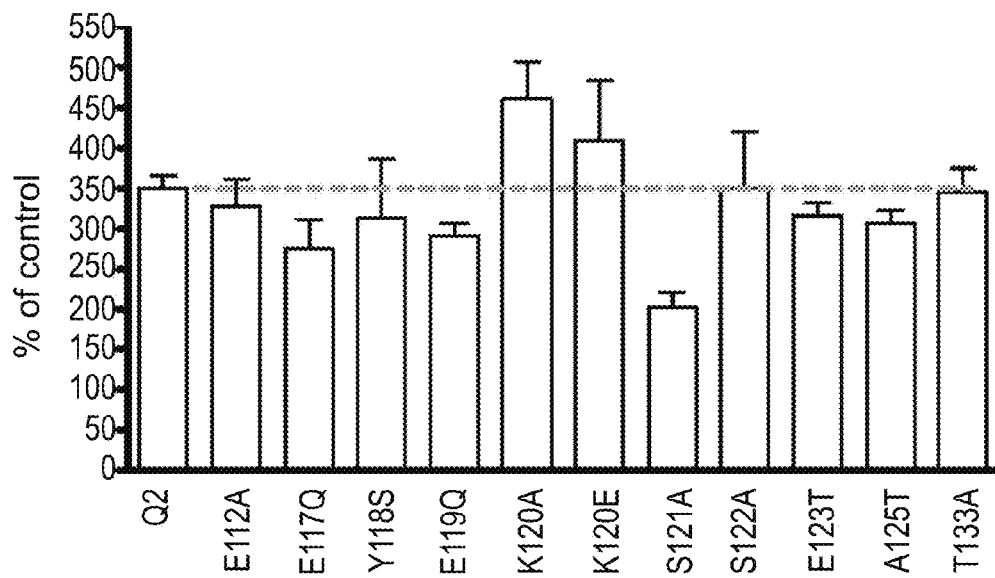
Figures 12B, 12C:
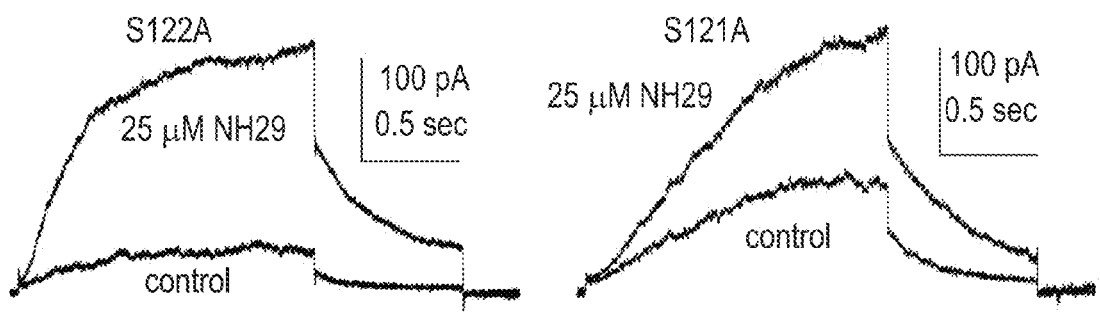

For comparison, FIG. 12A presents a bar diagram showing the potentiating activity of NH29 on KCNQ2 S1-S2 mutants. The activity of NH29 was preserved in almost all S1-S2 mutants. Interestingly, the only S1-S2 mutant which reduced the observed NH29 activity was S121A. S121A was significantly less activated (2-fold) by NH29 as compared to WT Kv7.2 channels (p<0.01; FIGS. 12A and 12C), while it is potently activated by RTG (more than 5-fold increase). Also shown is an example trace recorded from a CHO cell transfected with an S1-S2 mutation in which the NH29 activity was preserved (FIG. 12B) and a trace recorded from a CHO cell transfected with the S1-S2 S121A mutant in which case NH29 activity was significantly reduced.

FIGS. 11a-d present the potentiating effect of NH29, an exemplary channel opener compound according to embodiments of the present invention, on wild type KCNQ2 (FIGS. 11a and 11b) and R207W mutant (FIGS. 11c and 11d) channels, as expressed in activation curve measurements, showing that NH29 left-shifts the activation curve ($\Delta V_{50}$) by −15.5 mV and −5.5 mV in the case of the wild-type and the mutant, respectively, and showing that NH29 enhances the current of wild-type and the mutant by about 3.4-fold (at −40 mV) and 1.5-fold (at −20 mV), respectively.

As can be seen in FIG. 11, while 25 µM of NH29 activated the wild-type by 3.4-fold, it potentiates the current of the mutants R207W and Y118S by 1.5-fold and 2.1-fold, respectively (see also FIG. 8).

It is postulated that electrostatic and hydrogen bonding networks play a crucial role in docking the ligand to the VSD via interactions between a nucleophile/H-bonding acceptor connected to the phenyl rings of the molecule (see, FIG. 1) (e.g., nitro functionality in the exemplary compound NH29) and the guanidinium group/H-bonding donor from arginine residues in the S4 helix.

In addition, the terminal chain functionality of the molecule (FIG. 1) may interact with the "transduction site" at the S1-S2 or S3-S4 linkers, thereby providing the specificity of the drug action. In addition, the terminal chain hydroxyl function may be involved in hydrogen bonding with serine residue S121 in the S1-S2 linker (see FIG. 1).

Using the experimental constraints deduced from the mutagenesis studies, docking experiments of the opener NH29, an exemplary compound according to the present embodiments, to its Kv7.2 channel site were performed.

The results suggest that like scorpion toxins on voltage-gated Na$^+$ channels or tarantula toxins on voltage-gated K$^+$ channels, the Kv7.2 channel modulators of the present invention act as gating-modifiers which may interact with the externally accessible surface of the VSD at the groove formed by the interface between S4 helix and S1-S2. Thus, these gating-modifiers can trap the VSD either in the inward resting conformation (blockers) or the outward activated conformation (openers).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES CITED BY NUMERALS

Other References are Cited in the Text

1. Peretz, A., et al., *Meclofenamic acid and diclofenac, novel templates of KCNQ2/Q3 potassium channel openers, depress cortical neuron activity and exhibit anticonvulsant properties*. Molecular Pharmacology, 2005. 67(4): p. 1053-66.

2. Conte Camerino, D., D. Tricarico, and J. F. Desaphy, *Ion channel pharmacology*. Neurotherapeutics, 2007. 4(2): p. 184-98.
3. Robbins, J., *KCNQ potassium channels: physiology, pathophysiology, and pharmacology*. Pharmacol Ther, 2001. 90(1): p. 1-19.
4. Passmore, G. M., et al., *KCNQ/M currents in sensory neurons: significance for pain therapy*. J Neurosci, 2003. 23: p. 7227-7236.
5. Peretz, A., et al., *Pre-and postsynaptic activation of M-channels by a novel opener dampens neuronal firing and transmitter release*. J Neurophysiol, 2007. 97(1): p. 283-95.
6. Macdonald, R. L. and K. M. Kelly, *Antiepileptic drug mechanisms of action*. epilepsia, 1995. 36 (suppl 2): p. S2-S12.
7. Etxeberria, A., et al., *Three mechanisms underlie KCNQ2/3 heteromeric potassium M-channel potentiation*. J Neurosci, 2004. 24(41): p. 9146-52.
8. Tatulian, L., et al., *Activation of expressed KCNQ potassium currents and native neuronal M-type potassium currents by the anti-convulsant drug retigabine*. J Neurosci, 2001. 21(15): p. 5535-5545.

What is claimed is:

1. A method of blocking a transient receptor potential vanilloid 1 (TRPV1) in a subject in need thereof, the method comprising administering to the subject a therapeutically effective amount of a compound represented by Formula IV:

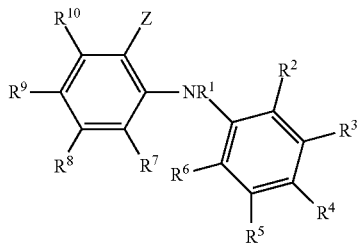

Formula IV wherein:
Z is an A-G(=K)—X—Y group,
and wherein:
A is alkyl or absent;
G is selected from the group consisting of C, S and PRa;
K is selected from the group consisting of O and S;
X is selected from the group consisting of NRb, O, S or absent; and
Y is selected from the group consisting of hydrogen, alkyl, hydroxyalkyl, cycloalkyl, heteroalicyclic, aryl and a polyalkylene glycol residue,
$R^1$ is selected from the group consisting of hydrogen, alkyl, cycloalkyl or aryl;
each of $R^2$, $R^3$, $R^4$, $R^5$, $R^6$, $R^7$, $R^8$, $R^9$ and $R^{10}$ is independently selected from the group consisting of hydrogen, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, an electron-withdrawing group, amino and —$NR^{15}R^{16}$, or, alternatively, at least two of $R^2$, $R^3$, $R^4$, $R^5$ and $R^6$, of $R^7$, $R^8$, $R^9$ and $R^{10}$ form a five- or six-membered aromatic, heteroaromatic, alicyclic or heteroalicyclic ring;
$R^{15}$ and $R^{16}$ are each independently selected from the group consisting of hydrogen, alkyl, cycloalkyl, aryl, carbonyl and sulfonyl, or, alternatively $R^{15}$ and $R^{16}$ form a five- or six-member heteroalicyclic ring; and
each of said Ra and Rb is selected from the group consisting of hydrogen, alkyl, cycloalkyl and aryl,
wherein said electron-withdrawing group is selected from the group consisting of nitro, ammonium, cyano, halo, trihaloalkyl, sulfonate, a —C(=O)X group wherein X is halide, a carboxy moiety, and a —C(=O)—R' group wherein R' is hydrogen, alkyl, cycloalkyl and aryl, said carboxy group being selected from carboxylate, amide, thiocarboxylate, dithiocarboxylate, thioamide, imide, N-substituted imide, thioimide and amidine.

2. The method of claim 1, wherein Y is selected from the group consisting of hydroxyalkyl and a polyalkylene glycol moiety.

3. The method of claim 1, wherein:
G is C;
K is O;
each of $R^2$, $R^3$, $R^4$, $R^5$ and $R^6$ is independently selected from the group consisting of hydrogen, alkyl, halo and trihaloalkyl; and
each of $R^7$, $R^8$, $R^9$ and $R^{10}$ is hydrogen.

4. The method of claim 1, wherein at least one of said $R^2$, $R^3$, $R^4$, $R^5$, $R^6$, $R^7$, $R^8$, $R^9$ and $R^{10}$ is said electron-withdrawing group.

5. The method of claim 4, wherein at least one of $R^7$, $R^8$, $R^9$ and $R^{10}$ is said electron-withdrawing group.

6. The method of claim 5, wherein at least one of $R^7$, $R^8$, $R^9$ and $R^{10}$ is said electron-withdrawing group and at least one of $R^2$, $R^3$, $R^4$, $R^5$ and $R^6$ is said electron withdrawing group.

7. The method of claim 4, wherein $R^9$ is said electron-withdrawing group.

8. The method of claim 1, wherein said compound is

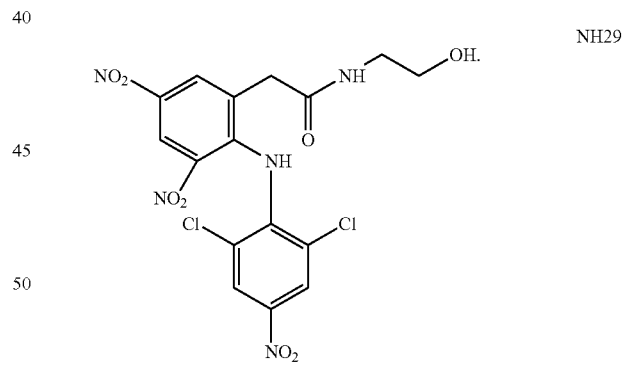

NH29

9. The method of claim 1, wherein said compound does not modulate TRPV6.

10. The method of claim 1, wherein blocking said TRPV1 is for reducing pain.

11. The method of claim 8, being for reducing pain in a subject in need thereof.

* * * * *